(12) United States Patent
Braunstein

(10) Patent No.: US 10,325,074 B2
(45) Date of Patent: Jun. 18, 2019

(54) QUALITY OF PRESCRIPTION MEDICATIONS AND QUALITY OF CUSTOMER SERVICES AT PHARMACIES USING ADAPTABLE AUTOMATIC DISTRIBUTED VENDING SYSTEM

(71) Applicant: Zachary Leonid Braunstein, San Marcos, CA (US)

(72) Inventor: Zachary Leonid Braunstein, San Marcos, CA (US)

( * ) Notice: Subject to any disclaimer, the term of this patent is extended or adjusted under 35 U.S.C. 154(b) by 179 days.

(21) Appl. No.: 15/135,549

(22) Filed: Apr. 21, 2016

(65) Prior Publication Data

US 2016/0314272 A1    Oct. 27, 2016

Related U.S. Application Data

(63) Continuation of application No. 62/152,262, filed on Apr. 24, 2015.

(51) Int. Cl.
| | |
|---|---|
| *G06F 19/00* | (2018.01) |
| *G05B 13/04* | (2006.01) |
| *B65G 17/18* | (2006.01) |
| *B65G 35/08* | (2006.01) |
| *B65G 65/23* | (2006.01) |

(52) U.S. Cl.
CPC .............................. *G06F 19/3456* (2013.01)

(58) Field of Classification Search
CPC ..... G06F 19/3456; B65G 35/08; B65G 65/23; B65G 17/18; G05B 13/041

USPC .................................................. 700/231–244
See application file for complete search history.

(56) References Cited

U.S. PATENT DOCUMENTS

| | | | |
|---|---|---|---|
| 7,036,679 B2* | 5/2006 | Baranowski | B65B 1/04 209/592 |
| 2001/0048027 A1* | 12/2001 | Walsh | A61N 5/1048 235/385 |
| 2004/0007584 A1* | 1/2004 | Baranowski | B65B 1/04 221/200 |
| 2004/0016799 A1* | 1/2004 | Walsh | A61N 5/1048 235/380 |
| 2008/0071421 A1* | 3/2008 | Silverbrook | G06Q 10/087 700/231 |

\* cited by examiner

*Primary Examiner* — Michael Collins

(57) ABSTRACT

Apparatus adapting to ambient environment and internal self-diagnostics operating within acceptance criteria, sustaining prescription medications within specifications, which in addition to conventional quality parameters include apparatus specific parameters, such as: combined weight of medication inside a container, and length of container. A control algorithm executed by apparatus sustaining operation within acceptance criteria. Apparatus including conveyor transport system configurable for vertical distribution of prescription medications between pharmacy and authorized user. Vertical configuration provides support for pharmacy to serve multi-story facility, such as a hospital. Automatic dispensing ensures high productivity and quality as only verified specification medications are dispensed to authorized customers.

21 Claims, 41 Drawing Sheets

Figure 1:
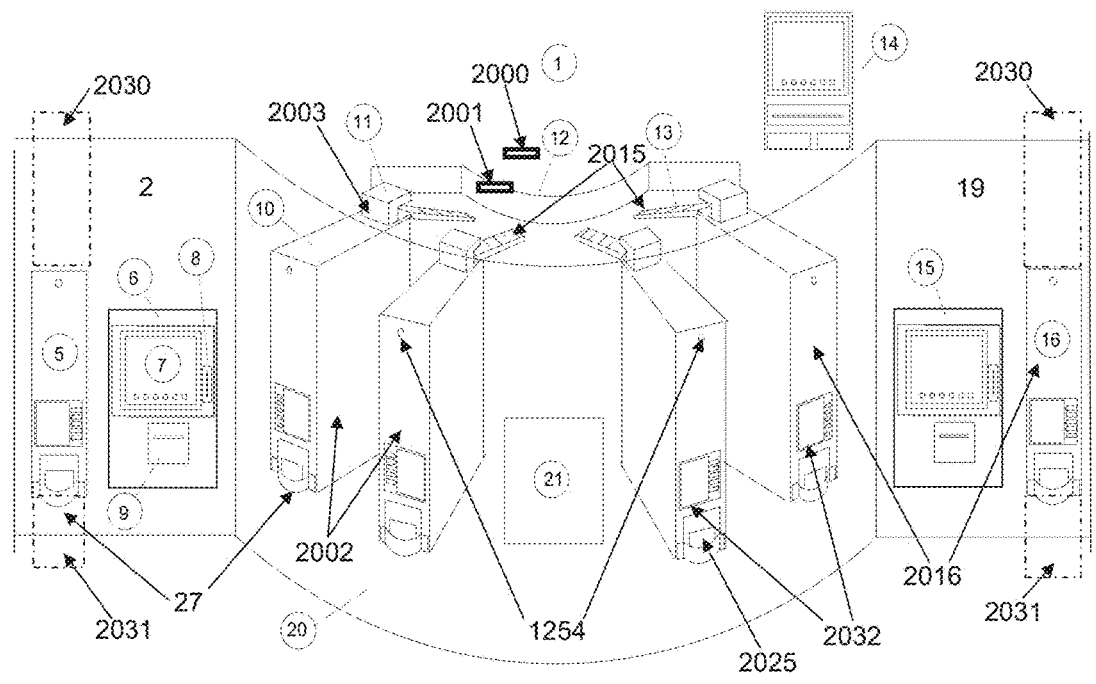

STEP #6 - Onsite dispensing, ADVS control ALGORITHM quality steps, including:

1) Calculate minimum required size of a CONTAINER to store required MEDICATION

2) Analyze inventory of MEDICATIONS on-site, including: weight and size of CONTAINERS with MEDICATION; weight and size of CONTAINERS with MEDICATION at specific ADVS Vending Modules; empty CARRIERS inside ADVS Vending Modules on-site; other MEDICATIONS ready for pick-up by the same CUSTOMER.

3) Select ADVS Vending Modules for potentially dispensing the MEDICATION, under CRITERIA:

3.1) CUSTOMER has another MEDICATION within the Module, and/or 3.2) Module has empty CARRIER to accept ADVS projected size of the CONTAINER with MEDICATION NOTE: ADVS will analyze the HISTORY of previous prescriptions for CUSTOMERS, and attempt to maintain 5-10% amount of empty CARRIERS within Modules to allow multi-MEDICATIONS to be dispensed to authorized CUSTOMER from one Module. As needed, ADVS will offer to PROVIDER options to re-locate some of the MEDICATIONS between Modules, in order to achieve the most efficient CUSTOMER service, including dispensing of several MEDCIATIONS from one Module.

4) Select empty CONTAINER (shape, size, weight) under CRITERIA:

4.1) Available from inventory, and the extra space after MEDICATION is loaded into CONTAINER, should not exceed the ADVS selected amount.

NOTE: ADVS will optimize use of CONTAINERS, by minimizing the variety of CONTAINERS, and minimizing the overall weight of CONTAINERS with MEDICATION 4.2) Within the selected Module:

- No duplicate weight (with MEDICATION), and duplicate size, or

- Minimum amount of MEDICATIONS with duplicate weight and/or duplicate size

5) Instruct PROVIDER to use selected CONTAINER (4) within the assigned ADVS Vending Module (3)

6) PROVIDER will be instructed, using ADVS devices, to verify the weight and size of the CONTAINER with MEDICATION inside, to comply with respective parameters calculated by ADVS ALGORITHM

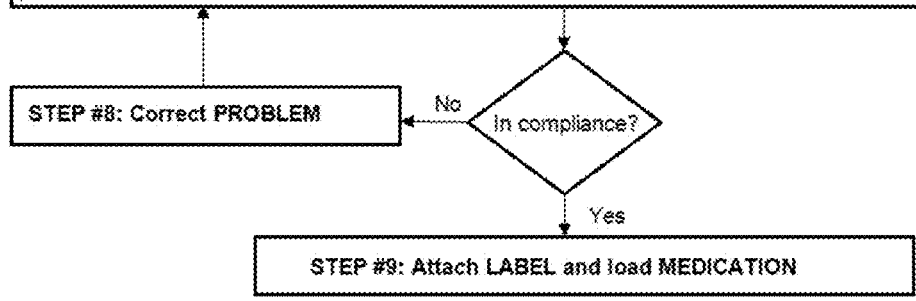

STEP #8: Correct PROBLEM ← No — In compliance?

Yes ↓

STEP #9: Attach LABEL and load MEDICATION

FIG. 52

STEP #7 - Offsite dispensing, ADVS control ALGORITHM quality steps, including:

1) Calculate minimum required size of a CONTAINER to store required MEDICATION

2) Analyze inventory of MEDICATIONS inside Portable Vending Cartridges (PVC) on-site, which are intended to be delivered to the same destination as the MEDICATION. In respect to these PVC's, the analysis will include weight and size of CONTAINERS with MEDICATION inside each PVC, empty CARRIERS inside PVC; other MEDICATIONS inside PVC intended for pick-up by the same CUSTOMER at the same location.

3) Select ADVS PVC for transporting the MEDICATION to destination location under CRITERIA:

3.1) Prefer CUSTOMER not to have another MEDICATION within the PVC, and/or 3.2) PVC has empty CARRIER to accept ADVS projected size of the CONTAINER with MEDICATION, and/or 3.3) PVC schedule for delivery to destination location is within MEDICATION requested date by CUSTOMER 4) Select empty CONTAINER (shape, size, weight) under CRITERIA:

4.1) Available from inventory, and the extra space inside the CONTAINER after MEDICATION is loaded into CONTAINER, should not exceed the ADVS selected amount.

NOTE: ADVS will optimize use of CONTAINERS, by minimizing the variety of CONTAINERS, and minimizing the overall weight of CONTAINERS with MEDICATION 4.2) Within the selected PVC:
- No duplicate weight (with MEDICATION), and duplicate size, or
- Minimum amount of MEDICATIONS with duplicate weight and/or duplicate size 5) Instruct PROVIDER to use selected PVC 6) PROVIDER will be instructed, using ADVS devices, to verify the weight and size of the CONTAINER with MEDICATION inside, to comply with respective parameters calculated by ADVS ALGORITHM

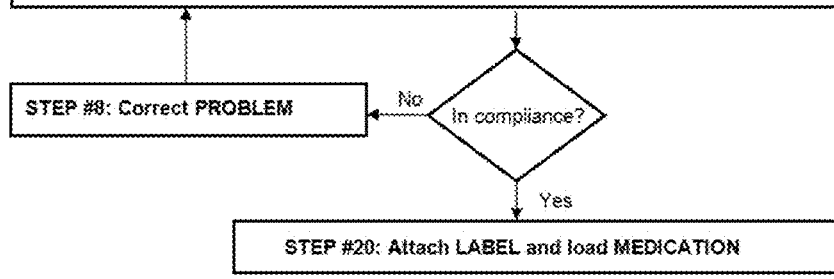

FIG. 53

STEP #20 - Attach LABEL and load MEDICATION, including:

1) PROVIDER per respective regulations will prepare the MEDICATION LABEL. For simplicity, a barcode label will be added to the LABEL, which will be used for automatic tracking of the MEDICATION, including within ADVS SYSTEM. ADVS will recommend PROVIDER to add information to the LABEL, which will help to improve QUALITY controls. The additional information, which is "linked" to the BARCODE label, can include:

- Origination: Date/Time/Place
   - MEDICATION weight and size (within ADVS estimated tolerances)
   - Acceptable ambient: temperature range, humidity range
   - Due date, expiration date 2) PROVIDER will attach the LABEL to the CONTAINER with MEDICATION, and scan the BARCODE label into the SYSTEM, allowing ADVS to obtain required information in respect to MEDICATION 3) ADVS will review status of the selected PVC, and when the PVC is available, will advance the ADVS conveyor to align the selected empty CARRIER for loading the MEDICATION 4) ADVS will inform PROVIDER (via Controller USER interface) to proceed and load the MEDICATION into the aligned CARRIER of the selected PVC 5) ADVS will perform incoming QUALITY control to verify if the following information is in compliance.
5.1) BARCODE label attached to MEDICATION
5.2) Proper identification of the selected PVC (if not—correction by PROVIDER is required)
5.3) MEDICATION weight and size (if not in compliance—correction by PROVIDER is required)

6) ADVS will attach the additional "location" related parameters: PVC ID, and CARRIER ID—into the ADVS data base, which is stored under the BARCODE for the MEDICATION

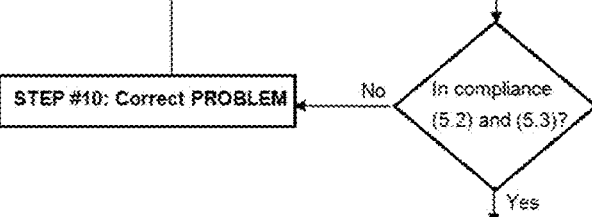

STEP #21: ADVS transport PVC to destination location

NOTE: In general, the respective steps in respect to CENTRALIZED processing of prescription MEDICATIONS using PVC, followed by distribution of MEDCIATIONS inside PVC to destination location, where the PVC will be installed into designated ADVS Vending Module—is described in details in my patent No. US 8,954,190. In respect to this application, additional PROCESS control steps, logically similar to the onside dispensing, will be introduced by ADVS QUALITY control ALGORITHM to further improve QUALITY of prescription MEDICATIONS and improve QUALITY of CUSTOMER services.

The NEXT STEP #22: At destination location—ADVS load PVC into ADVS Vending Module

FIG. 55

STEP #21 - At destination location—ADVS load PVC into ADVS Vending Module, including:

1) PROVIDER using ADVS devices will verify and confirm QUALITY compliance of each PVC with MEDICATIONS delivered to the destination location, including:

• PVC barcode ID

• PVC total weight vs. estimated weight calculated by ADVS QUALITY control ALFORITHM based on the weight of the empty PVC, plus the weight of MEDICATIONS loaded inside the PVC

• History of ambient environment, based on respective ADVS sensors, the PVC was exposed to from the point of being loaded with MEDICATIONS to the point of delivery 2) PROVIDER using ADVS devices will verify and confirm SECURITY compliance of each PVC delivered to the destination location, including: non-volatile records of authorized and non-authorized access to the interior of each PVC, as reported by the respective ADVS sensors and registered by respective ADVS controllers 3) PROVIDER per ADVS recommendations will load PVC's with MEDICATIONS into respective ADVS Vending Modules, based on criteria, including:

• Available space within compatible in size to PVC— ADVS Vending Modules

• Preferably, PVC will be loaded into the ADVS Vending Module where there is (if any) another PVC already installed, and the loaded PVC contains at least one MEDICATION allocated for a CUSTOMER which has another MEDICATION allocated in the PVC to be installed. This requirement will allow ADVS to execute practically simultaneous dispensing of at least two MEDICATIONS allocated to the same authorized CUSTOMER.

4) Once the PVC is loaded by PROVIDER into ADVS Vending Module, the ADVS will perform verifications, including: barcode label of the PVC to match the barcode label of the Vending Module; and expected increase in weight of the Vending Module by the weight of the loaded PVC.

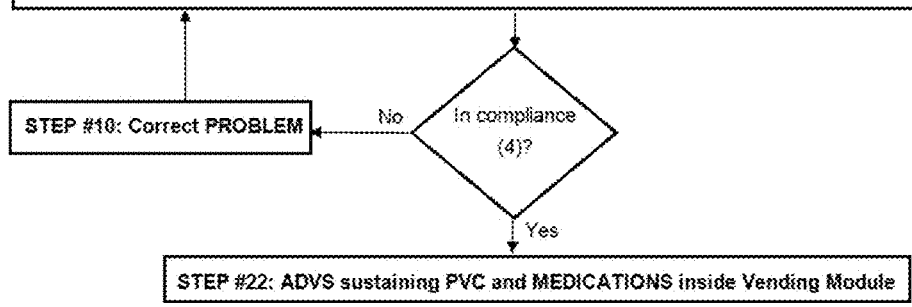

FIG. 56

STEP #11: ADVS sustaining MEDICATION, including:

1) ADVS sustaining MEDICATION inside the ADVS SYSTEM in full compliance to MEDICATION specifications, and executing in-process QUALITY controls at designated locations inside the ADVS Vending Module, including verification of parameters associated with the BARCODE label attached to the MEDICATION, which is identified by the ADVS barcode reading devices:

- MEDICATION location inside the Vending Module—via reading barcode label of the CARRIER, using ADVS barcode reading devices
- MEDICATION weight—using ADVS scales
- MEDICATION size- reading dimension barcode label of the CARRIER, using ADVS barcode reading devices
- MEDICATION ambient environment
- MEDICATION expiration date 2) ADVS will notify the PROVIDER of any rejected MEDICATION is detected and confirmed. The ADVS QUALITY control ALGORITHM criteria for rejection can be configured to issue a rejection status as result of the MEDICATION failing at least one of QUALITY verification steps, and then auto-dispense the rejected MEDICATION back to PROVIDER 3) ADVS in real-time will monitor and maintain the AMBIENT environment within specification requirements for MEDICATIONS stored within ADVS. ADVS Vending Modules will be configured to include required thermal insulations, and the ADVS conveyor systems will minimize vibrations, with practically no impact on MEDICATIONS being advanced by the conveyor.

STEP #12: Correct PROBLEM

1) Inform the PROVIDER

2) Dispense the rejected MEDICATION back to PROVIDER

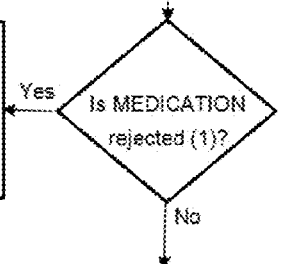

Is MEDICATION rejected (1)?

STEP #13: ADVS dispense requested MEDICATION(s) to authorized CUSTOMER

FIG. 58

STEP #13 - ADVS dispense requested MEDICATION(s) to authorized CUSTOMER, including:

1) ADVS inform the CUSTOMER when MEDICATION is ready for pick-up. The method of informing the CUSTOMER can be configured to allow the CUSTOMER to select any combination of: by phone call and/or text message, by email, etc.

2) Upon CUSTOMER arrival to pick-up MEDICATION(s), ADVS will verify CUSTOMER identity, and then allow the CUSTOMER to select the MEDICATION(s) ready for pick-up.

3) ADVS will verify the CUSTOMER prepaid for selected MEDICATION(s) and direct the CUSTOMER to ADVS Vending Module to pick-up the MEDICATION(s). When respective ADVS Vending Module is available (not busy), the first selected MEDICATION will be advanced by the ADVS conveyor toward the location for final QUALITY inspection 4) ADVS will perform final QUALITY inspection including verification of parameters associated with the BARCODE label attached to the MEDICATION, which is identified by the ADVS barcode reading devices:

- MEDICATION location inside the Vending Module—via reading barcode label of the CARRIER, using ADVS barcode reading devices
- MEDICATION weight—using ADVS scales
- MEDICATION size- reading dimension barcode label of the CARRIER, using ADVS barcode reading devices
- MEDICATION ambient environment
- MEDICATION expiration date 5) ADVS will dispense to authorized CUSTOMER only requested by the CUSTOMER MEDICATION(s) which is(are) in full compliance to QUALITY. If any MEDICATION failed the final QUALITY inspection, the PROVIDER will be notified, and the PROVIDER will be responsible to resolve the problem, including use of available ADVS resources as needed.

STEP #14: Correct PROBLEM
1) Inform the PROVIDER
2) Dispense the rejected MEDICATION back to PROVIDER

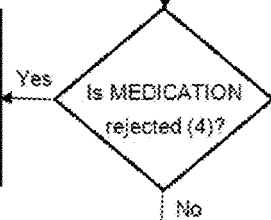

Is MEDICATION rejected (4)?

STEP #15: ADVS dispense requested MEDICATION(s) to authorized CUSTOMER

FIG. 59

STEP #23 - ADVS dispense requested MEDICATION(s) to authorized CUSTOMER, including:

1) ADVS inform the CUSTOMER when MEDICATION is ready for pick-up. The method of informing the CUSTOMER can be configured to allow the CUSTOMER to select any combination of: by phone call and/or text message, by email, etc.

2) Upon CUSTOMER arrival to pick-up MEDICATION(s), ADVS will verify CUSTOMER identity, and then allow the CUSTOMER to select the MEDICATION(s) ready for pick-up.

3) ADVS will verify the CUSTOMER prepaid for selected MEDICATION(s) and direct the CUSTOMER to ADVS Vending Module to pick-up the MEDICATION(s). When respective ADVS Vending Module is available (not busy), the first selected MEDICATION will be advanced by the ADVS PVC conveyor toward the location for final QUALITY inspection. If there is additional MEDICATION to be dispensed to the same CUSTOMER, the MEDICATION would be expected either next to the first MEDICATION inside the same PVC, or located inside another PVC within the same ADVS Vending Module. Since ADVS conveyor inside each PVC can be advanced independently of conveyors inside other PVC's within the same Vending Module, it will allow the ADVS QUALITY control ALGORITHM to advance the requested MEDCIATIONS in-parallel toward FINAL inspection, and upon full compliance, execute practically simultaneous dispensing of both MEDICATIONS to the CUSTOMER. This principal applied when more then 2 MEDICATIONS need to be dispensed to the same CUSTOMER, resulting in significantly more efficient and expediting services for the CUSTOMER. This is unique feature when using ADVS PVC.

4) ADVS will perform final QUALITY inspection including verification of parameters associated with the BARCODE label attached to the MEDICATION, which is identified by the ADVS barcode reading devices:

- MEDICATION location inside the Vending Module—via reading barcode label of the CARRIER, using ADVS barcode reading devices
   - MEDICATION weight—using ADVS scales, including scales measuring the weight of each PVC
   - MEDICATION ambient environment
   - MEDICATION expiration date 5) ADVS will dispense to authorized CUSTOMER only requested by the CUSTOMER MEDICATION(s) which is(are) in full compliance to QUALITY and SECURITY. If any MEDICATION failed the final QUALITY inspection, the PROVIDER will be notified, and the PROVIDER will be responsible to resolve the problem, including use of available ADVS resources as needed.

STEP #14: Correct PROBLEM
1) Inform the PROVIDER
2) Dispense the rejected MEDICATION back to PROVIDER

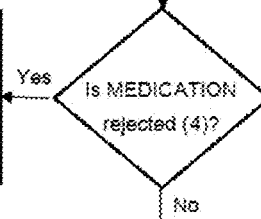

Is MEDICATION rejected (4)? — Yes → STEP #14; No ↓

STEP #15: ADVS dispense requested MEDICATION(s) to authorized CUSTOMER

FIG. 60

QUALITY OF PRESCRIPTION MEDICATIONS AND QUALITY OF CUSTOMER SERVICES AT PHARMACIES USING ADAPTABLE AUTOMATIC DISTRIBUTED VENDING SYSTEM

CROSS-REFERENCE TO RELATED APPLICATIONS

I claim the benefits of my provisional application No. U.S. 62/152,262 "Improving Quality of Prescription Medications and Quality of Customer Services at Pharmacies Using Adaptable Automatic Distributed Vending System" filed on Apr. 24, 2015.

STATEMENT REGARDING FEDERALLY SPONSORED RESEARCH OR DEVELOPMENT

Not applicable.

REFERENCE TO SEQUENCE LISTING, A TABLE, OR A COMPUTER PROGRAM LISTING COMPACT DISK APPENDIX

Not applicable.

BACKGROUND OF THE INVENTION

In general terms, the QUALITY Control ALGORITHM described in this application, once configured and integrated into a process control system will achieve the objective of Improving quality of the product produced by the process control system. The integration of the QUALITY Control ALGORITHM can require modifications of the process control system. In practical terms, there is no "perfect process", and there is no "perfect product". However, there are respectively acceptable statistical quality standards the processes and the products, under normal operating conditions, should comply with. Example of acceptable quality; under normal operating conditions the process control system should produce quality products at the minimum of 99.999%, meaning there can be maximum of one reject per 10,000 products produced. In respect to process control systems providing prescription medications—high rating of the product quality and the quality of customer service, are essential. In all practical terms, the process control system must ensure the quality of prescription medications delivered to a customer is in full compliance with the requirements of the medication listed in the medication specifications. The QUALITY Control ALGORITHM improves quality of a process control system, including operating environment of the system, enabling the system to statistically extend the quality range. As example, the process rated at 99.99999% quality, meaning there can be maximum of one reject per 1000,000 products produced. Not all existing processes are in compliance of providing required quality products. Unfortunately, this is also true for the existing process methods related to producing and delivery of prescription medications. Existing pharmacies do not meet requirements in respect to: quality of medication, quality of services, safety of raw materials and medications, security of customer's sensitive data, etc. The existing process control systems responsible for processing prescription medications, based on medication specification parameters, maintain respective data in computerized data bases, and also create a medication label to be attached to a container intended for storing the medication. The label will have the prescription medication unique identification, such as; a barcode label, patients name, medication name, etc. In majority of the existing systems, from the point of origination, the prescription medication location is tracked by respective electronic devices by its single identification—barcode label. The potential problems with the existing systems include:

1) Inadequate environment, including: process control technology, quality verification technology and general support for providers to avoid stress related mistakes in particular during high demand seasons, such as flu season, etc. The proper process environment is required to ensure best quality is attained at all time, including: proper selection of raw materials, determining if the correct dosage is deposited into the storage container, etc. Potential ERROR: wrong label attached to a container with medication.
2) Inadequate support for product identification in terms of quality process related of real time tracking and inventory management of the completed prescription within the system. Potential ERROR: sensor miss-reading a barcode label of a prescription medication, which accidently links the completed medication to another medication within the system, and the wrong medication being delivered without the system recognizing the ERROR (presence of the "other" medication within the system) prior to delivery.
3) Lack of monitoring ambient requirements listed in the product specifications, including: temperature, humidity, vibrations, exposure to radiation, etc. Potential ERROR: delivering prescription medications without analyzing the actual environmental conditions to which the medications were exposed to, and as result, potential changes in medication quality, including changes which can impact adversely the patient's health. As example, delivering medications by mall, is one of the most vulnerable process steps in terms of providing verifiable required ambient environment, and also introducing risks of errors related to "mail delivery", such as: wrong medications, wrong address, etc., which additionally factor in impacting in a negative way the quality of services, and quality of medications.

BRIEF SUMMARY OF THE INVENTION

The patent application describes processes improving quality of prescription medications, and improving quality of customer services using Automatic Distributed Vending System (AADVS). A QUALITY Control ALGORITHM (QUALITY ALGORITHM) is described, including the QUALITY ALGORITHM configurations and utilization in general applications, and in more specifics—configurations and application of the QUALITY ALGORITHM for improving quality of prescription medications, and improving quality of customer services using Automatic Distributed Vending System. In general, each product (PRODUCT) is produced by a technological process control system (PROCESS), with the PROCESS being configured to deliver quality PRODUCTS in compliance to PRODUCT specifications. The PROCESS itself can need to also comply with specification requirements outlined by the provider and/or respective agency, example: control of emissions produced by the PROCESS, etc. The QUALITY ALGORITHM objective is to identify key steps within a PROCESS of producing a specific PRODUCT, and introduce in-PROCESS specific quality verification steps which will not only improve the quality of the PROCESS, but also improve the quality of PRODUCTS produced by the PROCESS, with an ultimate objective to ensure only PRODUCTS in full compliance to specification requirements are delivered to customers. The QUALITY ALGORITHM can be configured for integration into a variety of new and existing PROCESSES. The criteria for QUALITY ALGORITHM configuration include: PRODUCT quality objectives, PROCESS quality objectives, COST of integration, PRODUCT cost. It is important to underline, the PRODUCT quality objectives can include required level of safety and security of handling the PRODUCTS by the PROCESS, as well as level of security and safety of selected PROCESSES producing the PRODUCT. The QUALITY ALGORITHM is based on performing analysis over the initial specification requirements for a PRODUCT, i.e. PRODUCT quality objectives. The QUALITY ALGORITHM will then analyze the requirements for a respective new or existing PROCESS, to ensure it is compliant to respective PROCESS quality objectives, and which is capable of producing the PRODUCT in compliance to respective PRODUCT quality objectives. As a result, the application specific configuration of the QUALITY ALGORITHM will establish required PROCESS quality verification steps and PRODUCT quality verification steps to achieve the required objectives. During initial evaluation of the existing PROCESSES producing a PRODUCT, the QUALITY ALGORITHM will identify potential voids in quality controls of PROCESS itself, and voids in quality verification of the PRODUCT being produced by the PROCESS. Based on this initial evaluation, the QUALITY ALGORITHM will identify in-PROCESS quality verification steps, required to be implemented into the PROCESS in order to achieve required results, including: improving quality of the PROCESS to deliver PRODUCTS in compliance to specification requirements, while meeting business objectives in terms of PRODUCT costs, etc. The integration of the QUALITY ALGORITHM into existing PROCESS can require modifications of the PROCESS. As result, the application describes the QUALITY ALGORITHM and the respective modifications of a PROCESS for integrating the QUALITY ALGORITHM in order to achieve quality and business objectives. In business terms, the QUALITY ALGORITHM objectives include:

a) Improving quality of PRODUCTS
b) Increasing efficiency and quality of customer services
c) Contributing to community and environmental safety
d) Expanding markets for business and improving business profit margins The recommended in-PROCESS quality steps identified by the QUALITY ALGORITHM are either implemented at the time the PROCESS is introduced (new PROCESS), or integrated into an existing PROCESS. The integration of the in-PROCESS quality steps can require modifications to the PROCESS. The in-PROCESS quality steps are also referenced as in-PROCESS quality parameters, and for simplicity will be referenced as PARAMETERS. The QUALITY ALGORITHM can achieve quality objectives by enhancing an existing PROCESS. The most effective and efficient utilization of the QUALITY ALGORITHM would be implementation of the QUALITY ALGORITHM during the initial design of the PROCESS, meaning the PROCESS itself is designed to effectively and efficiently support the requirements identified by the QUALITY ALGORITHM. For illustration purposes, the PROCESSES described in my AADVS PATENTS are used for illustrating the integration of the QUALITY ALGORITHM, and in combination—delivering the ultimate solution in achieving the objectives, including: providing quality prescription MEDICATIONS and quality CUSTOMER services. The PROCESSES described in my AADVS PATENTS were designed with an objective to provide configurable efficient and effective intelligent technological solutions for all kind and types of pharmacies, and the PROCESS capable of delivering quality MEDICATIONS and quality services to authorized customers. The PROCESSES in my PATENTS also describe quality related logistics, supporting the QUALITY ALGORITHM described in this application. The AADVS configurations described in this application are integrated with the respective configuration of the QUALITY control ALGORITHM, and include:

1) AADVS configuration for distribution/dispensing of MEDICATIONS and/or accessories for a PATIENT-specific environment, such as a stand-alone PHARMACY, abbreviated as AADVS-Ps. The main features of AADVS-Ps include:
   a) Each MEDICATION, including prescription medication, and/or accessories, is/are for a single PATIENT or CUSTOMER, and is housed in an individual CONTAINER, selected by PROVIDER at the time of completing the prescription per recommendations of the QUALITY Control ALGORITHM criteria, including CONTAINER's weight and/or size.
   b) Each CONTAINER is loaded by authorized PROVIDER into AADVS CARRIER.
   c) AADVS CARRIERS are configured to store/transport CONTAINER(s), with each CONTAINER allocated for a single PATIENT or CUSTOMER.
   d) Loading configurations of CONTAINERS with MEDICATIONS by authorized PROVIDER into AADVS CARRIERS include: automatic, semi-automatic and manual methods.
   e) Dispensing configurations of requested CONTAINERS with MEDICATIONS to authorized CUSTOMER include: automatic, semi-automatic and manual methods.
   f) Dispensing configurations of CONTAINERS with MEDICATIONS, either requested and/or rejected by AADVS QUALITY Control ALGORITHM, to authorized PROVIDERS include: automatic, semi-automatic, and manual methods.

2) AADVS distribution/dispensing of CONTAINERS with MEDICATIONS and/or accessories for a GROUP/FLOOR-specific environment, abbreviated as AADVS-Gs. AADVS-Gs configurations include configuration where a PHARMACY is located on a dedicated floor within a HOSPITAL, and then distribution/dispensing of CONTAINERS with MEDICATIONS from the PHARMACY floor to respective floors of the HOSPITAL for which the CONTAINERS with MEDICATIONS are intended for. The main features of the AADVS-Gs include:
   a) Each MEDICATION, including prescription medication, and/or accessories, is/are for a single PATIENT or CUSTOMER, and is housed in an individual CONTAINER, selected by PROVIDER at the time of completing the prescription per recommendations of the QUALITY Control ALGORITHM criteria, including CONTAINER's weight and/or size.
   b) Each CONTAINER is loaded by authorized PROVIDER into a section of the AADVS portable BASKET.
   c) AADVS portable BASKETS include adjustable configurations for housing a number of CONTAINERS, including CONTAINERS for a single CUSTOMER or CONTAINERS for a number of CUSTOMERS. The criteria of loading a BASKET with CONTAINERS for multiple CUSTOMERS includes location of the CUSTOMERS, such as a common floor at a hospital.

d) AADVS CARRIERS are configured to store/transport portable BASKETS, with each CARRIER configured for transporting either one or multiple BASKETS.

e) Loading configurations of BASKETS by authorized PROVIDER into AADVS CARRIERS include: automatic, semi-automatic and manual methods.

f) Dispensing configurations of requested BASKETS from AADVS CARRIERS to authorized PROVIDER includes: automatic, semi-automatic and manual methods.

g) Dispensing configurations of BASKETS, either requested and/or rejected by AADVS QUALITY Control ALGORITHM, to authorized PROVIDERS include: automatic, semi-automatic, and manual methods.

BRIEF DESCRIPTION

Drawing Content and Listing

List of all figures is presented in the Table 1, below.

TABLE 1

| FIG. | Description |
|---|---|
| 1 | 3-D view layout of AADVS-Ps pharmacy with integrated process QUALITY control ALGORITHM, with optional extensions up and/or down, in support of AADVS-Gs configurations |
| 2 | Z-Y view layout of AADVS-Ps pharmacy with integrated process QUALITY control ALGORITHM, with optional extension up in support of AADVS-Gs configuration |
| 3 | Z-Y view - Automatic Vending Module with integrated process QUALITY control ALGORITHM |
| 4 | Z-X view - AADVS Module with scales for measuring weight of selected sections of the Module |
| 5 | Z-X view - AADVS Module with common scales to measure combined weight of the Module |
| 6 | 3-D view - Dual pocket carrier |
| 7 | X-Y view - Dual pocket carrier |
| 8 | Carrier configuration details-1 |
| 9 | Carrier configuration details-2 |
| 10 | Example: even bar spaced barcode label for measuring length |
| 11 | 3-D view of Carrier Support configuration components |
| 12 | 3-D view of Carrier Support configuration assembly |
| 13 | Z-X view AADVS with Unloading Tunnel, default position |
| 14 | Z-X view AADVS with Unloading Tunnel dispensing items from all aligned carriers |
| 15 | Z-X view AADVS with Unloading Tunnel dispensing items from selected carriers |
| 16 | Z-X view configurable multi-item BASKET housing for transporting medications, accessories |
| 17 | X-Y view configurable multi-item BASKET for transporting medications, accessories |
| 18 | Views BASKET front/back WALL insertable plates |
| 19 | Views BASKET DIVIDER plates |
| 20 | Views BASKET main FRAME |
| 21 | X-Y view BASKET main FRAME |
| 22 | Views CARRIER for housing and transporting multi-item BASKET |
| 23 | Z-X view BASKET inside CARRIER |
| 24 | X-Y view BASKET inside CARRIER |
| 25 | Z-Y view AADVS conveyor transporting CARRIERS loaded with multi-item BASKET |
| 26 | Z-Y view AADVS conveyor transporting CARRIERS loaded with single ITEM |
| 27 | Z-X view AADVS-Gs (3000) 5 floors layout, one side open FLOOR services |
| 28 | Z-Y views AADVS-Gs (3000) configurations, single or dual AADVS conveyor systems |
| 29 | Views AADVS-Gs (3000) 5 floors layout with single AADVS conveyor for open FLOOR services |

TABLE 1-continued

| FIG. | Description |
|---|---|
| 30 | Z-X view AADVS-Gs (3300) 5 floors layout, one side FLOOR ROOMS services |
| 31 | Z-Y view AADVS-Gs (3300) configurations for FLOOR ROOMS services |
| 32 | Z-X view AADVS-Gs (3100) 5 floors layout, dual side FLOOR services |
| 33 | Z-Y views configurations of AADVS-Gs (3100) |
| 34 | Z-X view AADVS-Gs (3200) 9 floors layout, dual side FLOOR services |
| 35 | Z-Y view AADVS-Gs (3200) 9 floors layout, configurations with PHARMACY on 5-th FLOOR |
| 36 | 3-D view AADVS section (3501) configuration for a pharmacy floor |
| 37 | 3-D view AADVS section (3501) configuration for a service floor |
| 38 | 3-D view AADVS section (3521) configuration for two service floors, single or dual side services |
| 39 | 3-D view AADVS section (3551) configuration for two service floors, multi-side services |
| 40 | 3-D view AADVS section (3551) configuration for PHARMACY and one service floor |
| 41 | 3-D view AADVS section configuration for PHARMACY and two service floors |
| 42 | Z-Y view AADVS conveyor section single track, dual belt with verification of CARRIER weight |
| 43 | Views of AADVS CARRIER support component details |
| 44 | Z-Y view of AADVS CARRIER support details |
| 45 | Z-Y view AADVS conveyor verification of empty CARRIER weight |
| 46 | Z-Y view AADVS conveyor verification of loaded CARRIER weight |
| 47 | 3-D view AADVS conveyor belt with removable bearings |
| 48 | 3-D view construction details AADVS conveyor belt with insertable bearings |
| 49 | 3-D view construction details AADVS conveyor belt with molded bearings |
| 50 | 3-D view AADVS item feeding conveyor with incoming QUALITY verifications of the ITEMS |
| 51 | Flowchart - AADVS QUALITY control ALGORITHM process STEPS 1 through 7 |
| 52 | Flowchart - AADVS QUALITY control ALGORITHM process STEPS 6 through 9 |
| 53 | Flowchart - AADVS QUALITY control ALGORITHM process STEPS 7, 8, 20 |
| 54 | Flowchart - AADVS QUALITY control ALGORITHM process STEPS 9 through 11 |
| 55 | Flowchart - AADVS QUALITY control ALGORITHM process STEPS 10, 20, 21 |
| 56 | Flowchart - AADVS QUALITY control ALGORITHM process STEPS 10, 21, 22 |
| 57 | Flowchart - AADVS QUALITY control ALGORITHM process STEPS 12, 22, 23 |
| 58 | Flowchart - AADVS QUALITY control ALGORITHM process STEPS 11 through 13 |
| 59 | Flowchart - AADVS QUALITY control ALGORITHM process STEPS 13 through 15 |
| 60 | Flowchart - AADVS QUALITY control ALGORITHM process STEPS 14, 15, 23 |
| 61 | Z-X view AADVS conveyor VERTICAL index, ITEM auto-unloading to CUSTOMER |
| 62 | Z-X view AADVS conveyor VERTICAL index, ITEM auto-unloading to PROVIDER |
| 63 | Z-X view AADVS conveyor VERTICAL index, ITEM unloading details |
| 64 | Z-X view AADVS conveyor VERTICAL index, unloaded ITEM QUALITY verification details |
| 65 | Block-Diagram of the Apparatus |
| 66 | 3D view of the Item Carrier |
| 67 | 3D view of the Vertical Conveyor Transport System |
| 68 | 3D detailed view of the Vertical Conveyor Transport System |

DRAWING CONVENTION AND FORMAT

Drawings with this application are not to scale and are referenced to "X-Y-Z" coordinate system, which is consistent throughout all Drawings, where shown. Layout of the apparatus, including variety of the apparatus configurations, and location of the components within the apparatus—is for illustration purposes, in support of application specifications and claims.

DEFINITIONS

My application contains definitions of specific components or processes described in this application, and related definitions described in my PATENTS. Definitions are used and expanded in greater details in later paragraphs of this application, as needed.

AADVS
  Adaptable Automatic Distributing Vending System, which based on monitored ambient environment and monitored self-diagnostics executes in real-time controls to sustain operation of the system within predefined ACCEPTANCE CRITERIA.

AADVS-Ps
  AADVS configurations with integrated AADVS QUALITY control ALGORITHM for distribution and dispensing of MEDICATIONS and/or accessories for a PATIENT-specific environment, including configurations for: single and multi-floor stand-alone PHARMACIES; single and multi-floor hospitals. The AADVS configurations including AADVS providing services from AADVS supported PHARMACY directly to PATIENT rooms at designated floors.

AADVS-Gs
  AADVS configurations with integrated AADVS QUALITY control ALGORITHM for distribution and dispensing of MEDICATIONS and/or accessories for a GROUP/FLOOR-specific environment, including configurations for: multi-floor hospitals; multi-floor elderly care facilities. The AADVS configurations including AADVS providing services from AADVS supported PHARMACY directly to designated floors of the multi-story facility.

AADVS Pharmacy
  Pharmacy configured with AADVS components, including AADVS QUALITY control ALGORITHM.

AADVS Pharmacy Central
  AADVS configurations with integrated AADVS QUALITY control ALGORITHM in support of centralized processing of prescription MEDICATIONS followed by distribution and dispensing of MEDICATIONS to authorized CUSTOMERS at convenient locations, including locations on-site and remote. AADVS configurations for transporting MEDICATIONS include configuration based on AADVS Portable Vending Cartridges, as described in my PATENTS.

AADVS Pharmacy Kiosk
  Stand-alone kiosk configured with AADVS components allowing the kiosk to be refilled with medications and other items, which then can be dispensed automatically to authorized customers.

Quality Algorithm
  Quality controls using AADVS systems and AADVS components to ensure that only quality verified ITEMS, including prescription medications, are provided by AADVS to all Customers. The QUALITY ALGORITHM control criteria includes: incoming, in-process and final automatic verifications by respective AADVS components of MEDICATION and PROCESS specification parameters such as: weights (prescription medications, container with prescription medications), barcode label on the container with prescription medication; size of the container with prescription medication; environment surrounding MEDICATIONS (temperature, humidity); security—are verified to comply with QUALITY ALGORITHM criteria of respective parameters to insure only 100% quality verified ITEMS, including prescription medications, are provided to all Customers within high end standards for QUALITY customer services. The non-compliant, or rejected by AADVS ITEMS are returned back to PROVIDER.

Item
  Items as referenced in this application, include: prescription medications inside a container; over-the-counter medications inside a container; test samples, such as patient blood, urine: general items.

DETAILED DESCRIPTION OF THE INVENTION

For simplicity, unless specifically described in greater details, the following references to AADVS components and AADVS processes are abbreviated as follows:
AADVS Adaptable AADVS, including configurations for serving a pharmacy, which based on monitored ambient environment and monitored self-diagnostics executes in real-time controls to sustain operation of the system within predefined ACCEPTANCE CRITERIA.
ALGORITHM Includes adaptability to ambient environment, self-diagnostics, and executing quality control processes to ensure quality of prescription medications and/or quality of customer services are in compliance to ACCEPTANCE CRITERIA
MEDICATION Prescription medication, or CONTAINER with prescription MEDICATION
PROVIDER Authorized representatives of the pharmacy
CUSTOMER Authorized representatives of the patient (AADVS-Ps configurations), and/or authorized personnel within a facility serving patients (AADVS-Gs configurations)
FACILITY Includes: hospital, elderly care facility, etc., responsible for providing care to patients
SYSTEM AADVS configurations, including configurations supporting preparation, distribution, storage and vending of quality prescription medications to CUSTOMERS
QUALITY Prescription medications in full compliance to respective specifications, and supported by SYSTEM process control ALGORITHM providing convenient, safe and efficient services for CUSTOMERS and PROVIDERS
SYSTEM AADVS with integrated QUALITY control ALGORITHM operating within ACCEPTANCE CRITERIA For simplicity, the respective FIGS. listed in the Drawings include drawings which are illustrating AADVS components in a non-scale diagram type of format using primarily straight lines, and which is intended to demonstrate the principals and features of the designs. The actual configurations, including: size and shape, will be selected to provide reliable operation of all AADVS components. The AADVS configurations, include configurations shown on figures listed in the document DRAWINGS, and other configurations supporting the principals and methods described in the application.

The designs described in this application in respect to supporting the QUALITY ALGORITHM, include:
1) Designs in support of variety of configurations of the AADVS SYSTEM, illustrated on FIGS. 1-5, 13-15

2) Designs in support of variety of configurations of the AADVS carrier, which are illustrated on FIGS. 6-12. The carriers are attached to the AADVS conveyor, and are configured for accepting variety of types, sizes, and weights of MEDICATIONS. The carrier configurations support a number of important SYSTEM functions, including: loading (manual, automatic) of MEDICATIONS into the carrier; transporting of the MEDICATIONS by the carrier conveyor within a vending module with practically no impact, in terms of: vibration, internal friction between pills (as example) on the MEDICATION stored in the carrier; unloading (automatic dispensing, manual unload) of the MEDICATION out of the carrier. Additional configurations of the designs of the carrier are described in this application.

Figure 13:
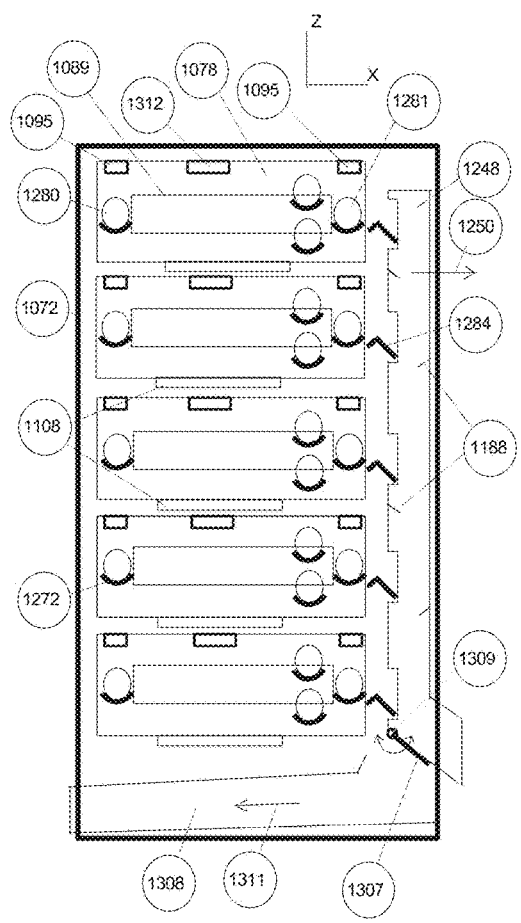
Figure 14:
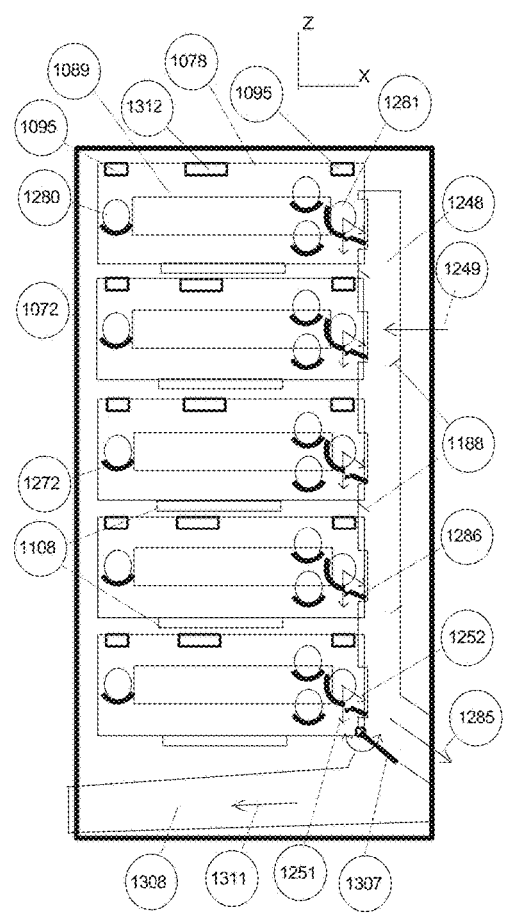
Figure 15:
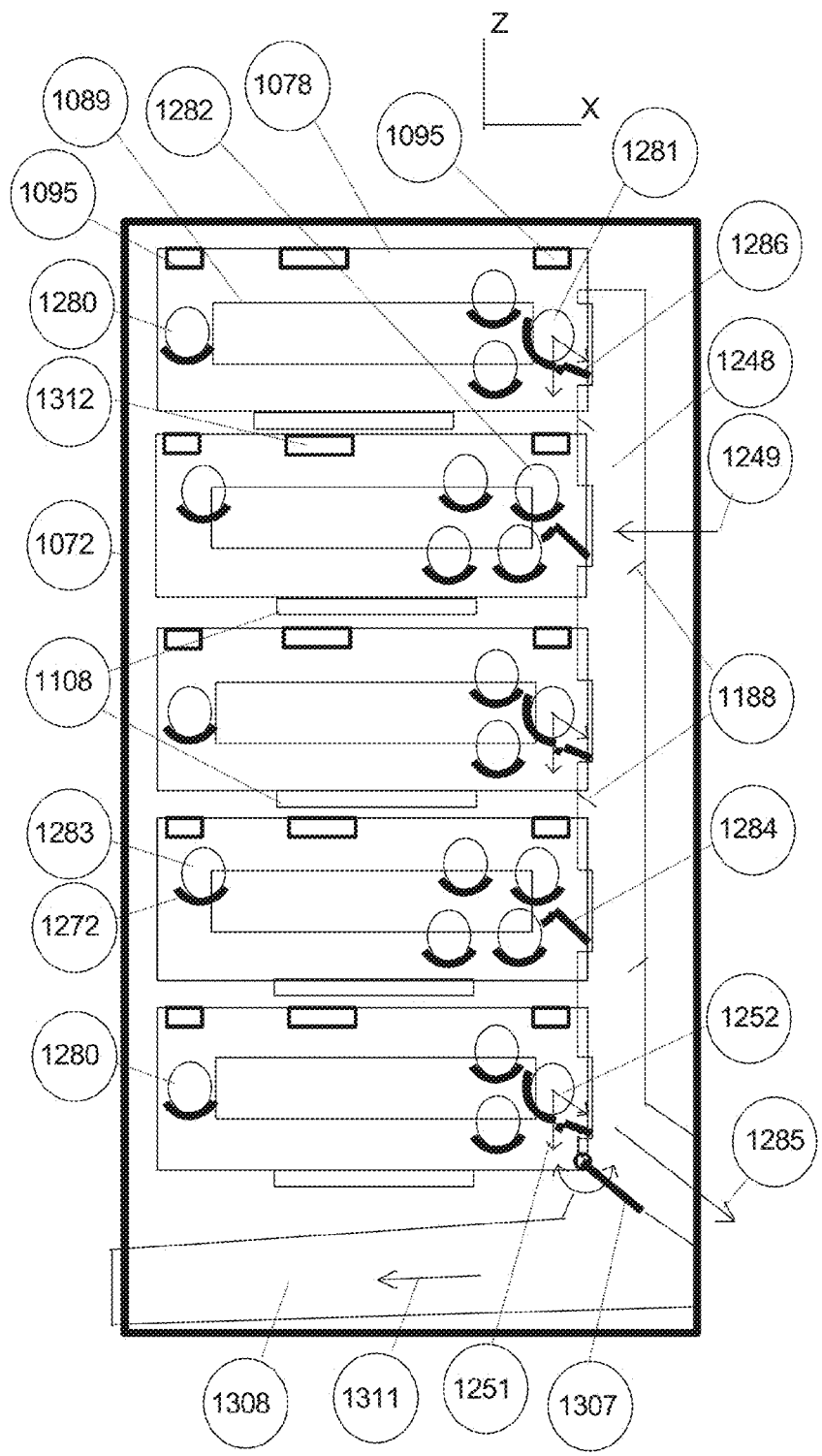

3) Designs in support of variety of configurations of the AADVS-Ps conveyor for transporting the carriers which are illustrated on FIGS. 13-15, and are providing convenient integration of the QUALITY ALGORITHM to effectively and efficiently achieve MEDICATION quality objectives.

4) Designs in support of variety of configurations of the AADVS-Gs conveyor for transporting the carriers which are illustrated on FIGS. 16-41, and are providing convenient integration of the QUALITY ALGORITHM to effectively and efficiently achieve MEDICATION quality objectives.

5) Designs in support of variety of configurations of the AADVS-Ps vending modules which are illustrated on FIGS. 1-5, 13-15. The designs support important SYSTEM functions, including: accepting, storing and dispensing MEDICATIONS, with in-process QUALITY verification and controls ensuring only quality MEDICATIONS are dispensed and/or delivered to authorized customer, while the rejected MEDICATIONS, or MEDICATIONS per request of an authorized PROVIDER, are dispensed or delivered back to PROVIDER. The designs are providing convenient integration of the QUALITY ALGORITHM to effectively and efficiently achieve required objectives, including: quality of MEDICATIONS; security and safety of MEDICATIONS; quality of customer services; protection of the environment, including energy efficiency and compliance to ROHS.

Example of measuring weight of a carrier for an AADVS conveyor configured with primarily vertical indexing of carriers is described below. The weight measurement of the carrier would take place at one or both locations, top and/or bottom of the conveyor, where the conveyor is changing direction of the motion. The top and/or bottom locations of the conveyor include a relatively flat section, allowing at least one carrier to be aligned such that there is no other carrier immediately below the carrier. The available space below the carrier will allow the scale platform to position itself in respect to the carrier and perform the measurement of the weight of the carrier. The process of measuring the weight of a carrier using AADVS components includes:

1) Index conveyor to align selected carrier with weight measuring station, and stop conveyor from moving.
2) Advance the scale platform from its original home position toward the carrier, and position the scale platform underneath the carrier, which can be labeled as the scale Z-home position.
3) Advance the scale platform from the Z-home position upward toward the carrier pocket, and elevate the pocket to disengage the weight of the pocket from the remaining parts of the conveyor. Note, the distance of the vertical elevation is within the respective limits set by the slots of the vertical brackets (left/right) supporting the carrier from the conveyor.
4) Measure the weight.
5) Lower the scale platform to the Z-home position. This will allow the carrier to move down and return back to its default support position by the conveyor,
6) Retract the scale platform back to its original home position, allowing the conveyor to index without interfering with the scale platform.

The above process will be performed prior to loading objects (container with medication) into the conveyor, in order to establish the weights of each empty carrier. A data base of the weights of each carrier will be established by the AADVS controller, based on barcode ID attached to the carrier and the measured weight of the empty carrier. The above process can be performed to verify the weight of an empty carrier, and the data base updated accordingly. The AADVS controller maintains up-to-date information (data base) of the inventory of carriers within AADVS vending module, and respectively within the entire AADVS system. In respect to the carrier, the configurations of the information maintain includes and or combination of: status of the carrier (empty, loaded, not available, etc.); weight of the empty carrier; length of the pocket of an empty carrier, shape of the empty pocket; current weight of the carrier with an object inside; length of the object inside the carrier, and other information as needed. The objective of the AADVS QUALITY ALGORITHM includes maintaining up-to-date information (data base) of locations and status of the objects (containers with medication) stored inside the carriers. The location of an object within AADVS consists of any combination of the following data: pharmacy ID where the object is located; AADVS equipment ID where object is located (vending module, transporting module, etc.); conveyor 10; carrier pocket 10; etc. In addition as a separate processes, or as a replacing processes of QUALITY verification steps in respect to measuring weight and/or size of the container with medications, will include stationary measuring stations for weight and distance/length of the container. The verification measurements of container weight and/or size are made at various process steps, including: prior to container entering AADVS module; periodic in-process verifications while within the AADVS; and as a final quality verification step prior to dispensing the container to an authorized customer.

Example of measuring size of an object inside a carrier for an AADVS conveyor configured with primarily vertical indexing of carriers is described below. The size measurement of the object inside the carrier would take place at one or both locations, top and/or bottom of the conveyor, where the conveyor is changing direction of the motion. The top and/or bottom locations of the conveyor include a relatively flat section, allowing at least one carrier to be aligned such that there is no other carrier immediately above the carrier. The reading of the barcode labels within AADVS can be accomplished statically—no movements of the object with the attached barcode label, or dynamically while the object with the attached label is moving at a speed within specified limits. In addition, the configuration (including specification of the label: type of label, size, location, etc.) of the barcode labels within AADVS includes configuration supporting an automatic process of reading respective barcode labels attached to a carrier pocket and/or attached to an object located within the pocket, by a single barcode reader, and the reading process can be either one or combination of static and dynamic processes. For simplicity, the static measurement is described below. The process of measuring the length of an object inside a carrier will include:
1) Attach barcode labels with evenly spaced bars for measuring distance to inner bottom surface, at the center, along each pocket of the carrier
2) Advance the conveyor and stop the carrier at the size measuring station/position, aligning the distance barcode label with the barcode reading device. Stop conveyor from moving.
3) AADVS controller attached to the barcode reading device—reading the barcode label, which is aligned underneath the device. AADVS controller calculating if the carrier pocket empty, or the length of an object inside the carrier pocket AADVS SYSTEM configurations, combining the AADVS components with integrated AADVS QUALITY control ALGORITHM, include configurations for providing quality prescription medications for a multi-floor facility, such as a multi-floor: hospitals, elderly care,—enhancing the SYSTEM list of outstanding features, by facilitating highly efficient and effective distribution of quality medications.

EXAMPLE #1

A Hospital with a 4-floor Configuration, with the Hospital Layout Configured as Follows 1-st floor: location of a pharmacy only. The pharmacy configuration includes storage of: raw materials; prescription medications; regular medications; medical accessories, in particular the items required for packing the medications, and items required for taking medications (dose cups, etc.)
2-4 floors: location of patients' room; hospital medical support staff medical equipment etc.
All floors: loading and unloading of items from AADVS—on one side
AADVS Configured as Follows:
1) The AADVS conveyor system configured as a VERTICAL index AADVS conveyor, including configuration of
    a) A single conveyor extending from the 1-st floor to the 4-th floor
    b) An independent multi-conveyor system with at least one conveyor extending from the 1-st floor to 4-th floor, and others extending from the 1-st floor to lower floors, as required to support demand for medications at each floor, and sustaining required reliability of the delivery system itself
2) Each AADVS conveyor configured based on one or combination of:
    a) Single track vertical conveyor
    b) Multi-track vertical conveyor
    c) Independent single track vertical conveyor
    d) Independent multi-track vertical conveyor
3) The AADVS at the 1-st floor providing full support for accepting and sustaining only quality items (medication and accessories) within the AADVS, including support for:
    a) Verification of quality of prescription medications, including: medication weight; container size.
    b) Verification of quality of regular medications, including verification of the known weight and size of the container with medications.
    c) Verification of quality of medical accessories to be distributed by the AADVS conveyors, including verification of the known weight and size of the package containing the medical accessories.
    d) Dispensing of medications and medical accessories back to PROVIDER, upon request by the PROVIDER, or automatically, as result of quality verifications, if any failed to comply to required quality parameters.
    e) Maintaining environment within the AADVS SYSTEM (conveyors throughout all floors) as required per specification of medications and accessories, handled by AADVS.
As needed, the AADVS conveyors can be functionally separated, assigned or individually allocated, with some conveyors configured to distribute one or combination of;
    Prescription medications requiring similar ambient environment
    Standard medications requiring similar ambient environment
    Medical accessories requiring similar ambient environment
4) The AADVS, maintaining real-time inventory of items within the AADVS, and sustaining only quality items within the AADVS, with items rejected being returned to PROVIDER
5) The AADVS at the distribution floors providing full support for verification of quality of items prior to dispensing, including:
    a) Verification of: item barcode label; destination floor; patient name; room number etc.
    b) Verification of item quality, including verification of: item barcode; carrier barcode where item is transported in; weight of item; size of weight. Item includes: prescription medication; standard medication; medical accessories; etc. which are distributed by the AADVS system.
The origination of a prescription for a patient within the hospital can be issued by an authorized physician anywhere within the hospital, or at an outside facility. The prescription, in addition to the patient name, and patient location parameters, such hospital room number, will have an additional parameter destination floor of the hospital where the patient is currently residing.
NOTE: If at the time of origination of the prescription, the patient location (hospital floor, room number, bed number, etc.) is not available or is not completed for any reason, the QUALITY ALGORITHM based on prescription information, including: prescription barcode, patient name, medication, based on information entered by PROVIDER (hospital), or linked directly from the hospital data base, will add the required destination parameters automatically, including which floor the AADVS conveyor should deliver the prescription medications to.

EXAMPLE #2

A Hospital with a 6-floor Configuration, with the Hospital Layout Configured as Follows 1) 1-st floor: location of a pharmacy only, with loading from two sides. The pharmacy configuration includes storage of: raw materials; prescription medications; regular medications; medical accessories, in particular the items required for packing the medications, and items required for taking medications (dose cups, etc.)
2) 2-6 floors: location of patients' room; hospital medical support staff, medical equipment; etc.
3) All floors: loading and unloading of items from AADVS—from one or both sides AADVS configurations include configurations supporting loading/unloading from all 4 sides (left/right/front/back). Each side can be functionally allocated to a specific range or type of items being distributed. The configuration of the AADVS, as also illustrated in the AADVS patent, includes configurations supporting loading/unloading to/from any combination of sides, including: opposite sides; adjacent sides.

EXAMPLE #3

A Hospital with 8-floor Configuration, with the Hospital Layout Configured as Follows 1) 4-th floor location of a pharmacy only, with loading from two sides. The pharmacy configuration includes storage of: raw materials; prescription medications; regular medications; medical accessories. In particular the items required for packing the medications, and Items required for taking medications (dose cups, etc.). In general, to optimize AADVS configuration in terms of: reliability, costs, etc., the AADVS system for tell buildings will include configurations based on independent AADVS conveyors, with a number of AADVS conveyors serving from a pharmacy located at a middle floor up to the upper floors, and a number of AADVS conveyors serving from a pharmacy located at a middle floor down to the lower floors. In addition, the weight of each AADVS conveyor will be optimized in terms of the number of carriers. Since in an AADVS configuration for a hospital, it is expected that the unloading of carriers at the respective floors will take place within a relatively short period of time (minutes), the distance in-between adjacent carriers supported from the AADVS conveyor will be increased. For example, if for the AADVS vertical configuration of a stand-alone system the clearance distance between the adjacent carriers loaded with a maximum height ITEMS can be set within 1-3 inches with an objective to optimize utilization of available space, in contrast the AADVS vertical configuration supporting multi-floor distribution the clearance distance between the adjacent carriers loaded with a maximum height multi-ITEM POCKET can be set within 12-36 inches with an objective to optimize the overall weight, and to keep it as low as possible while providing required service rates in terms of a number of medications delivered to each floor within a specified period of time. In addition, if the AADVS vertical configuration of a stand-alone system is designed for transporting and auto-dispensing medications to an authorized patient (patient-specific service), in contrast, the AADVS vertical configuration supporting multi-floor distribution will utilize multi-pocket carriers, allowing each carrier to transport a number of medications for a number of patients (floor-specific service) which will be manually removed from carrier by authorized personnel at each floor.
2) AADVS conveyor system #1 configuration serving from pharmacy floor #4 up to floors 5 through 8
3) AADVS conveyor system #2 configuration serving from pharmacy floor #4 down to floors 3 through 1
4) All floors: loading and unloading of items from AADVS include configuration allowing service from one or both sides of the conveyor Throughout all process steps. AADVS controllers monitor status of medications, and ensure that only medications with 100% compliance to respective specifications are made available to authorized Customers and/or authorized personnel.

FIG. 1—illustrates 3-D view of a pharmacy (1) configured using Automatic Distributed Vending System (AADVS), with integrated AADVS QUALITY control ALGORITHM. The configurations of the Automatic Distributed Vending System (AADVS) include AADVS configurations described in this application, and AADVS configurations described in my PATENTS. Selected number of the AADVS components and respective configurations included in my PATENTS are listed below.

1) From the patent No. U.S. Pat. No. 8,028,822 "Automatic Distributed Vending System":
   Carrier—illustrated on FIGS. 14 through 28 of the Drawings and described in the Specifications
   Carrier Conveyor—illustrated on FIGS. 29 through 62 of the Drawings and described in the Specifications
   Automatic Vending Module—illustrated on FIGS. 63 through 86 of the Drawings and described in the Specifications
   System—illustrated on FIGS. 1 through 7 of the Drawings and described in the Specifications
2) From the U.S. Pat. No. 8,954,190 "Optimization of Pharmacy Operations using Automatic Distributed Vending System"
   Carrier—illustrated on FIGS. 51, 52, 98, 99, 122, 123 of the Drawings and described in the Specifications
   Carrier Conveyor—illustrated on FIGS. 3 through 29 of the Drawings and described in the Specifications
   Portable Vending Cartridge—illustrated on FIGS. 31, 32 of the Drawings and described in the Specifications
   Automatic Vending Module—illustrated on FIGS. 30, 33 through 50, 124, 125, 126 of the Drawings and described in the Specifications
   System—illustrated on FIGS. 1, 2 of the Drawings and described in the Specifications The power distribution within AADVS can be configured per my U.S. Pat. No. 8,341,837 "Modular Power Distribution and Control System", and the identification of the AADVS devices can be configured per my U.S. Pat. No. 8,099,261 "Low-cost Solid-state Identification Device".

The configurations of the AADVS QUALITY control ALGORITHM include configuration illustrated on FIGS. 51-60 of this application. For simplicity, the AADVS configuration shown on FIG. 1 is for a stand-alone pharmacy, which is configured for preparation, storage, distribution, and dispensing of MEDICATIONS and/or dispensing accessories for a PATIENT-specific environment, abbreviated as AADVS-Ps. For simplicity, the layout of the AADVS apparatus, including variety of configurations of the AADVS components of the apparatus, and location of the components within the apparatus, are for illustration purposes, in support of specifications and claims of this application.

Figure 3:
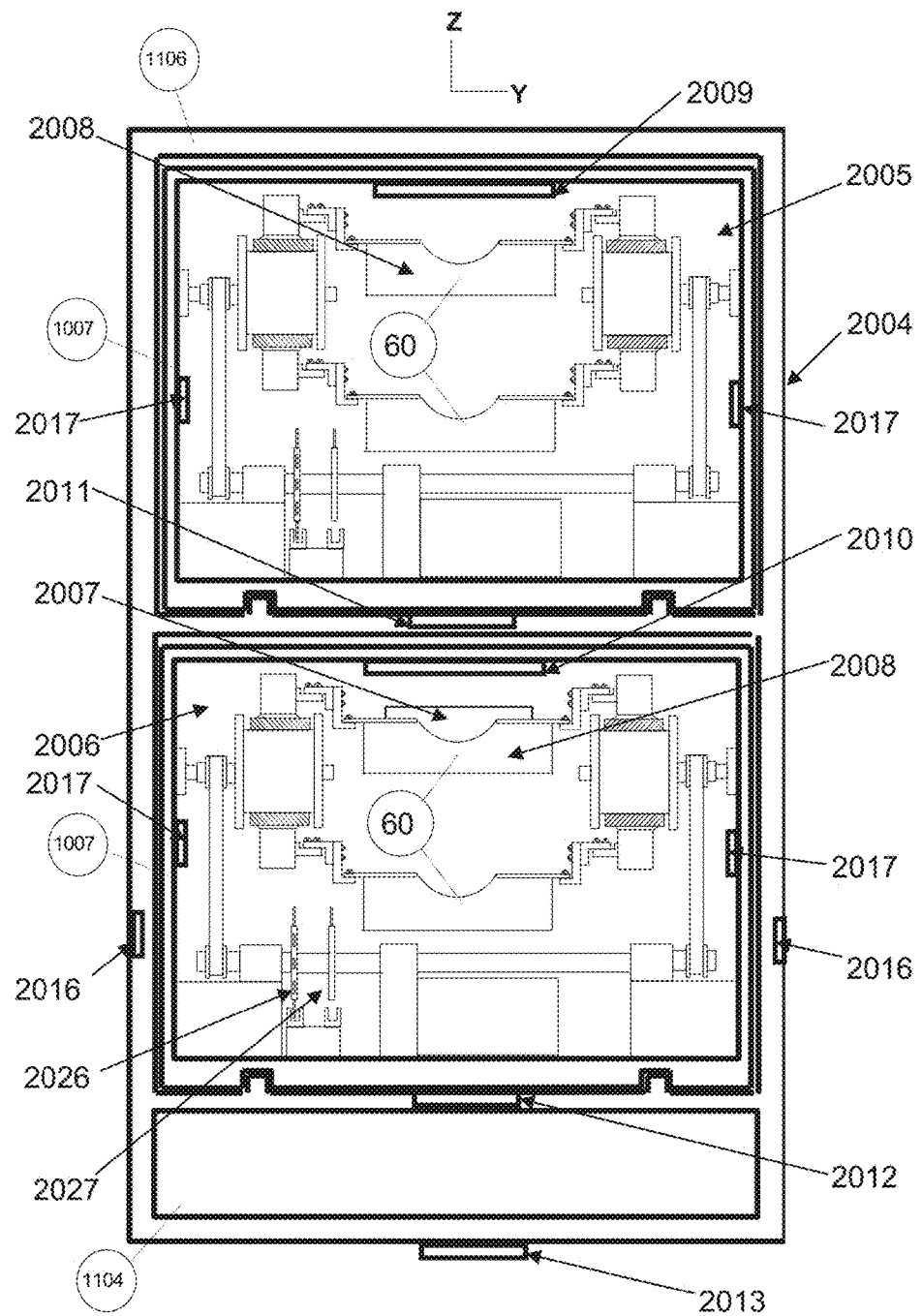

The AADVS vending modules (5,10,16) are configured to support AADVS-Ps, and are further configured for:
1) Supporting either one or combination of: on-site MEDICATION processing of individual prescriptions, and/or centralized MEDICATION processing of individual prescriptions delivered to the pharmacy in AADVS portable vending cartridges described in my patents.
2) Supporting dispensing of quality MEDICATIONS at the floor level of the pharmacy to authorized CUSTOMERS. As needed, the configuration of the AADVS vending modules can be changed in support of distribution and dispensing of the MEDICATIONS to the floors located above the pharmacy, and/or the floors located below the pharmacy. For simplicity, the extension (2030) is illustrated for the AADVS vending modules (5,16) extending the service from the pharmacy floor to the floors located above the pharmacy, while extension (2031) extending the service from the pharmacy floor to the floors located below the pharmacy. For simplicity to describe the process details performed by the PROVIDER inside the pharmacy, the wall (20) is shown as transparent. The AADVS components comprising the AADVS-Ps (1) with AADVS QUALITY control ALGORITHM, are also illustrated and described on FIGS. 2-15, 42-50. The AADVS-Ps (1) includes the following features:

1) Each MEDICATION (or accessory), including prescription medication, is for a single PATIENT or CUSTOMER, and is housed in an individual CONTAINER, selected by PROVIDER at the time of completing the prescription per recommendations of the AADVS QUALITY control ALGORITHM criteria, including CONTAINER's weight and/or size
2) Each CONTAINER is loaded by authorized PROVIDER into AADVS CARRIER directly (manual process), or indirectly with the assistance of the AADVS auto-loading components (11,13), as shown on FIG. 1
3) AADVS CARRIERS are configured to store/transport CONTAINER(s), with each CONTAINER allocated for a single PATIENT or CUSTOMER
4) Dispensing configurations of requested CONTAINERS with MEDICATIONS to authorized CUSTOMER include: automatic, semi-automatic and manual methods
5) Dispensing configurations of CONTAINERS with MEDICATIONS, either requested and/or rejected by AADVS QUALITY control QUALITY ALGORITHM, to authorized PROVIDERS include: automatic, semi-automatic, and manual methods The application describes AADVS automation technology, including AADVS configurations for improving QUALITY of operations at pharmacies, with number of objectives and features, including: superior quality of products delivered to customers with written reports confirming "100% factory sealed quality"; safety of raw materials and medications; highly efficient service rate of medications to customer; superior privacy of sensitive information related to customers; variety of configurations and layouts indoor and outdoor to enhance pharmacy appearance and expanding service to unattended kiosks. As part of automating pharmacy operations, AADVS configurations include configuration handling prescription and non-prescription medications. For simplicity, a specific AADVS PROCESS configuration is selected, which includes a pharmacy (PROVIDER) with installed Automatic Distributed Vending System (AADVS) as illustrated on FIG. 1. The PROCESS configuration, as illustrated on FIG. 1, includes the AADVS QUALITY control ALGORITHM process steps illustrated and described on FIGS. 51-60, such as:
  a) PROVIDER—preparation of MEDICATIONS with assistance from AADVS (2000, 2001)
  b) PROVIDER—per direction from AADVS, manually loading each MEDICATION into respective empty carrier of a conveyor within a specific vending module of AADVS (11, 13, 2015)
  c) AADVS—performing incoming verification of MEDICATIONS before accepting them from PROVIDER (2003, 2015)
  d) AADVS—maintaining the MEDICATION within specifications, and returning/dispensing back to PROVIDER rejected MEDICATIONS (2002, 2016)
  e) AADVS—dispensing only MEDICATIONS in-compliance to specifications to authorized customer (2025)

The QUALITY control ALGORITHM will be configured for the AADVS PROCESS illustrated on FIG. 1. While the AADVS was designed to provide only quality MEDICATIONS, addition of the QUALITY ALGORITHM to the AADVS will ensure that all quality objectives are implemented effectively and efficiently. In general, the PROCESS of producing MEDICATIONS includes a number of important PROCESS steps. For simplicity, the following STEPS are considered:

1) Verification of prescription issued by an authorized physician for a MEDICATION. If accepted—unique identification tag (ID) for the MEDICATION is assigned.
   Example: ID can be a barcode label. RFID, combination of both, etc.
2) Review of specification requirements for the MEDICATION requested by the physician.
   Example: medication type, unit dosage, total amount of units, etc.
3) Review of specification requirements for the type of MEDICATION prescribed, as directed by a respective agency. Example: safety requirements, security requirements, warning labels, etc.
4) Review of specification requirements for customer service, as directed by a respective agency
   Example: customer information privacy, packing procedure for completed MEDICATION, etc.
5) Review of customer requirements in respect to MEDICATION, including: location and date for pick-up or delivery, other prescription MEDICATIONS present within the system
6) Review of customer service history
7) Prepare MEDICATION summary of requirements, based on previous STEPS.
   Example: an abbreviated version of the MEDICATION summary together with the MEDICATION ID will be printed on the MEDICATION label, to be attached to a container selected for housing the MEDICATION.
8) Allocation of: respective amount of raw material, technology, personnel for preparing the MEDICATION within the set objectives and requirements, including in-process quality and final quality inspections of the MEDICATION
9) Preparation of MEDICATION
10) Storage of MEDICATION
11) Providing MEDICATION to an authorized customer The PROCESS STEPS 1 through 8 are primarily related to verification of data in preparation for a MEDICATION to be PROCESSED in STEPS 9 through 11. For simplicity, assuming STEPS 1 through 8 are executed by PROVIDER as required per respective regulations, the paragraph below focuses on application of the QUALITY ALGORITHM for the remaining PROCESS STEPS 9-11. For reference, under existing logistics within a pharmacy:

STEP 9: Preparation of MEDICATION. MEDICATION will be extracted in required volume or quantity from the selected raw material, and placed into a container which will have a MEDICATION label attached. The container with MEDICATION will be placed into a bag with another MEDICATION label attached.

STEP 10: Storage of MEDICATION. The bag with the container and MEDICATION inside will be placed into a storage bin, indexed by an order selected by PROVIDER. Example: first letter of the customer name.

STEP 11: Providing MEDICATION to an authorized customer. When requested and paid for by an authorized customer, the PROVIDER will locate the corresponding bag, based on parameters: MEDICATION ID, name of customer, and then issue the bag to the customer.

For simplicity the AADVS with integrated application-specific configuration of the QUALITY ALGORITHM will be referenced as a SYSTEM. For illustration purposes, the SYSTEM will be configured as follows:

A) The SYSTEM controller based on the MEDICATION ID, will have access to respective PROVIDER data base containing MEDICATION summary as described by STEP 7.

B) The SYSTEM controller will have access to respective PROVIDER data base containing raw material information (weight of unit of measurement ambient environment for storing and transporting, etc.) in respect to MEDICATION summary as described by STEP 7.

C) The SYSTEM will provide assistance to the PROVIDER for executing STEPS 8-9, and full support for executing STEPS 10-11. NOTE: The PROCESS steps associated with providing user interface, and the process of authorization of a customer to obtain MEDICATION, is considered to be managed by the PROVIDER, with addition of a coordinated interface to the SYSTEM for executing appropriate dispensing of requested MEDICATION.

In general, the AADVS is designed to provide a comprehensive system-level and component-level support for the effective and efficient integration of the QUALITY ALGORITHM during the initial installation of a new SYSTEM, and support for gradual phase-by-phase integration onto an existing AADVS. System-level support for the QUALITY ALGORITHM includes AADVS configurations for supporting a number of system-level functions, including:

1) Centralized processing of prescription medications, in particular the refill prescriptions
2) On-site processing of prescription medications
3) Combination of the above, while maintaining the quality of medications at all times Component-level support for the QUALITY ALGORITHM includes AADVS device configurations for supporting a number of process control functions, including:

1) User interface
2) Manual, semi-automatic and automatic loading of MEDICATIONS into vending modules
3) Manual, semi-automatic and automatic unloading of quality MEDICATIONS from vending modules to authorized customers
4) Automatic monitoring and control of in-PROCESS quality to ensure compliance to respective quality objectives identified by the QUALITY ALGORITHM. This includes monitoring and sustaining required ambient environment (temperature, humidity, vibration, etc.) surrounding the MEDICATION
5) Automatic inspection of MEDICATION quality parameters, including inspection of in-PROCESS PARAMETERS introduced by the QUALITY ALGORITHM, which are performed by the respective devices at the point of MEDICATION entry into AADVS; within AADVS continuously while MEDICATION is stored in the AADVS; and prior to MEDICATION being dispensed from AADVS. The PARAMETERS can include any or combination of: weight of container with medication; size of the container with medication; location of the medication within AADVS identified by the vending conveyor carrier ID, and vending module ID; etc.
6) Automatic dispensing of rejects back to PROVIDER, as soon as the non-complaint medication was detected
7) Automatic monitoring of inventory resources, including: status (empty, loaded, out-of-service, etc.) of carriers within a vending module; status (available capacity, full, out-of-service, in-user-service, etc.) of vending modules within the AADVS
8) Automatic monitoring of inventory and location (vending module, carrier within the module, etc.) of medication within AADVS. s inside resources, including: status (empty, loaded, out-of-service, etc.) of carriers within a vending module; status (available capacity, full, out-of-service, in-user-service, etc.) of vending modules within the AADVS
9) Automatic monitoring of the apparatus safety and security, including safety and security of MEDICATIONS located within AADVS SYSTEM. The safety and security monitoring configurations include: devices for verification and authorization of the personnel assigned by the PROVIDER; SENSORS installed inside enclosures where the MEDICATIONS are located, such as: SENSORS inside AADVS Portable Vending Cartridges (PVC) and AADVS Vending Modules, which will be configured to monitor and record safety and security status, such as un-authorized brake-in and/or opening of the enclosure.

It is assumed, that the STEPS 1 through 7, have an adequate support from the PROVIDER, and as result, will be completed by the PROVIDER within required guidelines and acceptance quality criteria. AADVS interfaces to PROVIDER include: AADVS control interfaces (touch screens, keypads, etc.); AADVS information/instruction interfaces (monitors, LED status lights, etc.); and other required system and local level interfaces. In respect to remaining PROCESS STEPS 9 through 11, the SYSTEM activities will include:

STEP 9: Preparation of MEDICATION. Based on newly introduced MEDICATION summary for a specific MEDICATION ID (STEP 7), AADVS controller (14) will obtain MEDICATION quality requirements, including which raw material should be selected to prepare the MEDICATION. The QUALITY ALGORITHM, with respective sections of the ALGORITHM control programs, interface programs, etc. will reside inside AADVS controllers, primarily controller (14). The ALGORITHM, utilizing the SYSTEM (hardware and software) resources of the AADVS, will:

1) Calculate the weight of the MEDICATION itself (without any additives, etc.)
   Example: unit weight times number of units.
2) Instruct PROVIDER using AADVS control interfaces (monitors situated with assistance from AADVS components (2000)—to verify the combined weight of MEDICATION prepared by the PROVIDER, which should be equal to calculated weight (1)
3) Calculate the minimum space required for storing the MEDICATION, and any required additives, such as (example for pills): cotton ball to minimize motion of pills inside container, water absorbent pack to keep the pills dry, etc.
   Example: unit volume times number of units, plus the calculated volume of additives.
4) Analyze on-hand inventory of available containers for storing MEDICATION.
   Example: container data—weight size, storage volume.

5) Analyze availability of empty carriers within the vending modules of the AADVS at the location where the MEDICATION is expected to be delivered to the customer or patient.
6) Introduce PARAMETER #1—By selecting container from the inventory per at least one of the following criteria, which must be unique in respect to the at least one of the vending modules available (5):
   a) The combined weight of the selected container with the MEDICATION
   b) The size of the container with MEDICATION
   NOTE: the selection of weight, size or combination of both, depends on inventory of MEDICATIONS within the SYSTEM, and also the reliability of technology available for conducting in-PROCESS quality verifications of the selected criteria without causing "false" alarms!
7) Prepare the MEDICATION label with required information. The label can include barcode label, which can be used for auto-tracking the MEDICATION location within the SYSTEM,
8) Introduce PARAMETER #2—by selecting the vending module for loading the MEDICATION
   Example: Vending module which is in compliance to criteria (6a)
   NOTE: Vending modules of the AADVS can be configured to provide: controlled environment of the entire module or a section of; added security and/or safety for stored MEDICATIONS, etc. The selection of the vending module by the QUALITY ALGORITHM will be made based on the entire set of requirements listed in the MEDICATION specifications, and availability of the vending modules with specific configuration to meet those requirements. If the existing AADVS inventory is insufficient to support the QUALITY ALGORITHM, the request will be made to PROVIDER to add required AADVS resources to ensure the SYSTEM fully supports the quality objectives.
9) Instruct the PROVIDER to use the container per (6)
10) Verify the PARAMETER #1 was selected property by measuring the actual weight of the container with MEDICATION vs. the calculated weight, using AADVS components (2001). In addition, the size of the container can be also verified to match the size of the container recommended by the AADVS for additional quality controls.
11) Instruct PROVIDER to attach the label prepared in (7) to the container with MEDICATION and perform verification of the label via AADVS components (2001).
   NOTE: The label is attached to the container with MEDICATION after the PARAMETER #1 is verified, practically eliminating the probability that the label can be attached to a wrong container with different MEDICATION.

STEP 10: Loading MEDICATION into AADVS, and sustaining the MEDICATION inside AADVS per respective specifications for the MEDICATION, and sustaining MEDICATIONS inside AADVS within safety and security requirements introduced by the AADVS QUALITY control ALGORITHM. Based on STEP 9, the SYSTEM will:
1) Prepare the vending module selected in STEP 9(8), and align an empty carrier of a proper size and shape for accepting the MEDICATION.
2) Instruct the PROVIDER to use the vending module selected in STEP 9(8) for loading the MEDICATION
3) Verify using AADVS components (2003) the proper (ID, weight, size) MEDICATION was loaded into the carrier of the selected vending module.
   PARAMETER #3—ID of the vending module and the carrier within the module where the MEDICATION is loaded, are linked to MEDICATION as on-going in-PROCESS control PARAMETERS of the AADVS.
4) Monitor in-PROCESS PARAMETERS and quality specification parameters (MEDICATION ID, location, environment, weight, size, due date, security, etc.) related to MEDICATION, while MEDICATION is within AADVS, using AADVS components (2002). Execute respective AADVS supported PROCESS controls to sustain in-PROCESS quality. Promptly identify non-compliance, and return MEDICATION as reject back to PROVIDER using AADVS provided support for dispensing rejects.
5) Monitor MEDICATIONS safety and security within AADVS using AADVS sensors (2016). Promptly identify non-compliance, and inform the PROVIDER to resolve the problem. In addition to QUALITY verifications, AADVS prior to dispensing will verify the status of MEDICATION safety and security, and dispense the MEDICATION in full compliance to QUALITY, safety and security.
6) Maintain history (REPORT) of quality monitoring results of in-PROCESS PARAMETERS and specification parameters related to MEDICATION, and make the REPORT available to PROVIDER and customer, if required by PROVIDER logistics. The REPORT can include the entire chronology of important events, including: the date/time/location of the origination of the MEDICATION to the date/time/location of the dispensing of the MEDICATION.

STEP 11: Dispense MEDICATION to authorized CUSTOMER. The PROVIDER will inform the CUSTOMER the MEDICATION is available for pick-up. To pick-up MEDICATION, the CUSTOMER will need initially present required ID at AADVS controller (6 or 15). The AADVS ALGORITHM will:
1) Instruct the CUSTOMER to present required ID
2) Verify CUSTOMER ID
3) Display the available MEDICATION(s) for the PATIENT pick-up
4) Instruct the CUSTOMER to select MEDICATION(s) for pick-up.
   NOTE: One of the criteria of the ALGORITHM is to maintain high efficiency of CUSTOMER services. As result, as much as possible, the MEDICATIONS prescribed for a specific PATIENT will be loaded and sustained within a single AADVS vending module.
5) Inform the CUSTOMER to proceed to the AADVS vending module with specific ID (1254) where selected MEDICATION will be dispensed. NOTE: If the selected AADVS vending module is available, the ALGORITHM will start blinking the module status ID (1254) in green color, and begin advancing the first (if not only) selected MEDICATION inside the vending module toward final inspection and dispensing.
6) At the AADVS vending module with specific ID, the ALGORITHM via CUSTOMER interface (2032) will instruct the CUSTOMER to confirm ID, and make required payments for the MEDICATION(s) selected
7) Verify CUSTOMER ID and confirm required payments were made by the CUSTOMER (2032)

8) Perform FINAL QUALITY inspection of the MEDICATION and confirm compliance (2025)
9) Perform MEDICATION safety and security record, and confirm compliance (2016)
10) Dispense the MEDICATION(s) to the pick-up bin (27), and inform the CUSTOMER via (2032)—MEDICATION is ready for pick-up.
11) Provide onsite support for the CUSTOMER, including: on-screen (2032) instructions, which can be printed out; HISTORY report for each MEDICATION, confirming its compliance to specifications; other support available online, or by phone, or in-person via pharmacy service window (21).

As part of the improving quality of services of customers, the projected and the actual availability of the MEDICATION at the required location for dispensing to an authorized customer can be added by the QUALITY ALGORITHM as an important in-PROCESS quality PARAMETER. In addition, the SYSTEM as combination of AADVS resources and the QUALITY control ALGORITHM, can implement functions related to maintaining security and safety regulations or requirements related to specific MEDICATION. The QUALITY ALGORITHM will perform these functions, including: while the MEDICATION is within AADVS; customer private information; packing the MEDICATION at the time of dispensing; protecting the MEDICATION from being accessed from the customer side while the MEDICATION is being stored within AADVS; protecting the MEDICATION from being accessed by un-authorized PROVIDER while the MEDICATION is within AADVS.

The above description of the SYSTEM, and the role of the QUALITY ALGORITHM, is supported by simple mathematics. Majority of existing pharmacies rely on processing prescription medications without verification of in-process parameters, such as: weight of the medication. For example, the weight and the size of the container, and then the weight of the container with medication inside, are not added to the quality requirements, and as result, not monitored. The existing system track the medication by a single identification, which is primarily includes a unique barcode label attached to container with medication, with another equal label attached to the packing bag, and respective documentation within the pharmacy. This existing processes, including the ones in compliance to the current regulations, still are insufficient to achieve the expected quality results expected for prescription medications. It is important to underline, that the QUALITY ALGORITHM will use specific criteria of selecting PRODUCT specific in-PROCESS quality PARAMETERS, to avoid unnecessarily burden on the SYSTEM, including potentially high level of "false" alarms, resulting in unjustifiable increase in the amount of rejected medications, and potential impact on PRODUCT costs. The mathematics in support of the QUALITY ALGORITHM are described below. For simplicity a simple PROCESS is selected for illustration of the principals and mathematical support of the results. In general terms, if the quality determination of the PRODUCT from a known process step (example STEP 3, for reference) relies on verification of a single parameter, example PRODUCT ID, then the PROCESS relies on previous process steps preceding STEP 3 for ensuring that the quality of the PRODUCT was verified before the PRODUCT ID was attached. Below are 2 EXAMPLES with simplified PROCESS to illustrate the logic.

EXAMPLE 1

An ITEM from a warehouse was requested for being shipped to a customer.

STEP 1: locate the ITEM within the warehouse
STEP 2: place the ITEM into a shipping box
STEP 3: attach ITEM ID label to the shipping box and ship the ITEM
STEP 4: verify presence of the ITEM during the storage/delivery using the ITEM ID label on the shipping box
STEP 5: deliver the ITEM per ITEM ID label on the shipping box

EXAMPLE 2

A prescription MEDICATION was requested from a pharmacy to be prepared and then shipped to a customer STEP 1: prepare MEDICATION per prescription
STEP 2: place the MEDICATION into a storage container, and attach MEDICATION ID label to the container
STEP 3: place the container with MEDICATION into a shipping box
STEP 4: attach MEDICATION ID label to the shipping box and ship the box
STEP 5: verify presence of the MEDICATION during the storage/delivery using the ITEM ID label on the shipping box
STEP 6: deliver the MEDICATION per MEDICATION ID label attached on the shipping box In the EXAMPLE 1—the PROCESS relies on the in-PROCESS quality of STEPS 1-3, and then on the quality inspections of the ITEM ID label for the remaining STEPS 4-5. In the EXAMPLE 2—the PROCESS relies on in-PROCESS quality of STEPS 1-4, and then on the quality inspections of the MEDICATION ID label for the remaining STEPS 5-6. In both EXAMPLES, assuming the PRODUCT ID is a barcode label, there are STEPS (STEP 4-5, example 1; STEP 5-6, example 2) within the PROCESS, which do place the PRODUCT quality based on verification of a single parameter—proper identification of the barcode label. As result, there is a quality "bottle-neck" created, where a single quality verification process of a parameter—the barcode label in this case, can impact the quality of the end PRODUCT being delivered to a customer. For simplicity, let's assume the SYSTEM barcode reading device has an accuracy rating of 99.99% (potential single ERROR can happen in 10000 barcode scans). CONCLUSION: if the PRODUCT is delivered by mail, then the SYSTEM quality rating cannot exceed the quality rating of the "bottle-neck" quality STEP, which is the quality rating of the barcode label of 99.99%. In simple terms, the PROCESS can deliver a wrong PRODUCT in 10000 shipments. Application of the QUALITY ALGORITHM to both examples, would result in modification of the PROCESS, with the QUALITY ALGORITHM after reviewing the specifics of the PROCESS and requirements for the PRODUCT quality, adding in-PROCESS verification parameter such as the weight of the ITEM or MEDICATION. The initial weight would be established respectively at STEP 2 (example 1), and at STEP 3 (example 2), and the weight PARAMETER will be included in the ID label, and all the following STEPS would include verification of both the barcode and the weight PARAMETERS. For simplicity, let's assume the SYSTEM weight measuring device has an accuracy rating of 99.99% (potential single ERROR, causing an actual weight being measured outside of the device known tolerances, can happen in 10,000 measures). With the application of the QUALITY ALGORITHM, the quality of both PROCESSES has improved, since the probability of missing an ERROR in reading the barcode and the weight for a given PRODUCT is significantly lower. In simple terms, the PROCESS after integration of the QUALITY ALGORITHM can deliver a wrong PRODUCT in 100,000,000 shipments. That is a significant improvement.

NOTE: While the probability of delivering a wrong PRODUCT has been drastically reduced, the potential reject rate remained at 1 out of 10,000 shipped! Mathematical review of both EXAMPLES 1.2 is illustrated below. Let's name the:

Barcode as PARAMETER #1, and the weight as PARAMETER #2

Respective reject rates as REJECT #1=0.00001 and REJECT #2=0.00001

For simplicity let's define the:

SYSTEM quality as the probability for all identified quality PARAMETERS being rejected at the same time.

SYSTEM reject rate as the probability for at least one identified quality PARAMETER being rejected.

For the SYSTEM without the QUALITY ALGORITHM, relying on PARAMETER #1 only:

SYSTEM quality=REJECT #1=0.00001

SYSTEM reject=REJECT #1=0.00001

For the SYSTEM with integrated QUALITY ALGORITHM, relying on PARAMETER #1 and PARAMETER #2:

SYSTEM quality=logical AND of (REJECT #1, REJECT #2)

SYSTEM quality=(REJECT #1+REJECT #2)=0.000000001

SYSTEM reject=logical OR of (REJECT #1, REJECT #2)

SYSTEM reject=(REJECT #1+REJECT #2)=0.000000002

Conclusion: while the SYSTEM quality was drastically improved by the QUALITY ALGORITHM, the probability of a rejected PRODUCT has doubled in ratio. In respect to the above EXAMPLES, the SYSTEM reject ratio can be improved. One of the methods for improving the SYSTEM reject ratio includes increasing tolerances (acceptance range for the PRODUCT weight measurement) for the PARAMETER #2. The QUALITY ALGORITHM for selecting the in-PROCESS quality control parameters includes criteria for the selection to avoid or minimize the burden on the SYSTEM, including potential increase of: rejects; "false" alarms, etc. In general, the SYSTEM reject ratio and probability of "false" alarms can be lowered by the QUALITY ALGORITHM by increasing tolerance or increasing the acceptance range of results attained at the in-PROCESS quality verification steps introduced by the QUALITY ALGORITHM. In respect to EXAMPLES 1,2—the ALGORITHM based on analyzing results of potential increase in the SYSTEM rejects, would:

1) Analyze the weights of other similar PRODUCTS within the SYSTEM, and
2) Selecting the shipping box, which together with the PRODUCT inside, will produce a combined weight different from other shipping boxes being processed by the SYSTEM within the same section of the SYSTEM, which would allow the QUALITY ALGORITHM to increase the acceptance window for the actual measurement of the weight of the box with the PRODUCT inside, to reduce the probability of unnecessary rejects, while maintaining the PRODUCT quality at the required level.

As result, the reject rates for PARAMETERS #2 can be reduced from 0.00001 to 0.000005, as an example. This would reduce the overall SYSTEM level reject rate from 0.00002 to 0.0000015, equal to 25% improvement. The QUALITY ALGORITHM will take into account a number of logical scenarios in respect to attaining the most effective and efficient PROCESS. For example, the ALGORITHM will consider the following available options:

1) Addition of a similar PARAMETER to the ones already introduced into the SYSTEM, for example additional second unique barcode label attached to the MEDICATION (container with medication), can improve the process of quality verification, and/or
2) Duplication of barcode readers at a quality verification location will lower the probability that both will cause an error at the same time at that location, and can improve the process of quality verification.
3) Risks, associated that the SYSTEM hardware implementation can use a data link connecting all or some barcode readers, which can create a situation of an ERROR related to the data link itself.

Figure elements are labeled as follows:

6, 15—AADVS Station Controller #1 and #2 respectively. Controller can be configured as a local Host Controller, and also for initial verification of Customer identification. Station Controller will perform all required functions, including real-time synchronization controls, in support of the safe, reliable and efficient operations of the AADVS components. AADVS Controller will synchronize with all respective stand-alone controllers to monitor and control in real-time a number of functions, including: status, inventory. Status will include: location, availability, operating condition, environment. Inventory will include: equipment, stored medications inside. Inventory will be monitored via local controllers connected to respective sensors, including: barcode, RFID. Status will be monitored via local controllers connected to respective sensors, including: environment, safety. Synchronization control will include support of: centralized processing of prescription medications, on-site processing of prescription medications, and combination of both. AADVS controllers will also monitor and control status of medications within the AADVS, including: expiration date, environment weight location, status (request date/time, location). AADVS Controllers will synchronize the inventory and status information to ensure: required medications within respective specifications are available for dispensing to authorized Customers at specified locations and time; corrective controls are executed in real-time to ensure that only medications within their specifications are dispensed to authorized Customers. In respect to Customers, AADVS Controller can be configured to provide required user interface (2032), including: verification of identification, on-site processing of payments for medications purchased, on-site help/assistance in respect to instructions on how to use medications.

10—Automatic Vending Module (AVM) configured with: user interface (2032); sensors (2002, 2003, 2015) for verification of quality of MEDICATIONS; sensors (2016) for verification of safety and security of MEDICATIONS inside AADVS; and MEDICATION pick-up bin (27). AVM configurations include AVM configuration as shown on FIG. 1 in support of AADVS-Ps configurations. Controller at AVM, if not occupied, will lit the ID sign (1254), and advance Carriers inside to prepare medications for dispensing as soon as informed by the Station Controller of a pending transaction to an authorized Customer. AVM Controller via user interface will confirm Customer identification, and selected medications for which the Customer paid at the Station Controller. AVM Controller will allow Customer to specify if consultation is required, and if medications Log Report should be printed. Customer has a choice to select consultation via: on-site Pharmacist at the Service Window (21); or AADVS real-time voice/video on-site via AVM user interface; or remotely via Internet. Customer can also select if medications should be dispensed and packaged inside a box. AVM Controller will then proceed with: final QUALITY verifications; safety and security verifications; and after full compliance will dispense requested medications to authorized customer. Customer will pick-up medications from the pick-up bin, and receive print-outs of instructions and the log history, as selected. The Log Report will contain essential information in respect to medications, including: origination date and location; conformance to specifications—environment, weight, size of container, due date. The AVM Controller will control the ID sign (1254).

5, 16—AADVS vending modules with configuration selected in support of AADVS-Ps configurations, or as needed, in support of AADVS-Gs configurations, as indicated by module extensions (2030) extending the service from the pharmacy floor to the floors located above the pharmacy, while extension (2031) extending the service from the pharmacy floor to the floors located below the pharmacy.

7—Station Computer #1 touch-screen monitor, as part of user interface. The monitor at the Station Computer or at the Automatic Vending Module (10) can be used by Controllers to interface with Customer and Provider, including allowing authorized Customer to preview the Log History of prescription medication stored inside respective AVM unit before selecting the medication for being dispensed.

8—Station Computer #1 card reader, which can be configured to perform variety of functions, including: accept ID cards, ATM/credit cards, as part of identification and payment options.

9—Station Computer #1 printer, which can be configured to print: sales receipts; instructions; log history of dispensed medications.

11—AADVS Automatic Item Loading/Unloading assembly configured together with Automatic Item Feeding assembly (13) for on-site loading of medications, and incoming QUALITY verification (2003, 2015) of MEDICATIONS prior to accepting them into the AADVS vending modules (10)

12—Area behind Modules, which can be configured for Provider working bench/area, including: monitoring on-site processes; QUALITY control verifications (2000, 2001).

13—Automatic Item Feeding assembly, which can be configured to include AADVS QUALITY verification components (2015), which can be configured to perform any combination of the quality controls, including: barcode reader to identify the prescription medication before being loaded; scale to measure weight of container with medication; feeding conveyor; and other support devices which can be used by AADVS Controllers to monitor inventory, status and quality of prescription medications inside the AADVS.

14—AADVS Host Computer, which can be configured to coordinate all activities within AADVS, and Interface with other Controllers within and outside AADVS via wired or wireless LAN.

19—AADVS right partition wall

20—AADVS center partition wall

27—Item Pick-up Bin, Customer side. As needed, the dispensed medications can be presented to the Customer in privacy packaging, as described in my patents.

2000—AADVS components or devices, including sensors, which are configured by AADVS QUALITY control for verifications of: barcode labels, weight, and size of an object. The AADVS weight measuring components are used for measuring weight, and include weight verification of: raw medications, empty containers, and containers with medications inside. The details in respect to measuring weight of a CARRIER are illustrated and described on FIGS. 42-26. The AADVS barcode reading devices are used for verification of: barcode label attached to an object, and for measuring the length of an object, as illustrated and described for FIG. 19. The components (2000) are used by PROVIDER and the SYSTEM. As shown on FIG. 1, the (2000) are used by PROVIDER and the SYSTEM during the initial processing of a prescription.

2001—AADVS components or devices described for (2000), which are used by PROVIDER and the SYSTEM prior to the process step of loading a container with medication into a vending module, including (5, 10, 16).

2002—AADVS scale installed inside a vending module, and is configured for verification of the weight of the carrier conveyor installed inside a vending module, including (5, 10, 16). Monitoring the weight of the conveyor, allows the AADVS QUALITY control to detect and verify proper addition and/or removal of items from the conveyor, including: increase in the weight of the conveyor by the weight of a container with medication, when the expected container with medication was added; decrease in the weight of the conveyor by the weight of a container with medication, when the expected container with medication was removed, including dispensed to an authorized CUSTOMER.

2003—AADVS components or devices described for (2000), which are used by the SYSTEM as part of incoming process verification of container with medication before being accepted by the AADVS vending module, including (5, 10, 16).

2015—AADVS components or devices described for (2000), which are used by PROVIDER and the SYSTEM as part of incoming process verification of container with medication before being accepted by the AADVS loading module, including (11, 13).

2016—AADVS components or devices which are configured and used by the SYSTEM for verification of: environment within the AADVS vending module; SECURITY and SAFETY of items inside AADVS vending modules, including (5,10,16). The components for monitoring environment include: temperature sensors; humidity sensors. The components for monitoring SECURITY include sensors for monitoring position of panels enclosing the AADVS vending module.

2025—AADVS components or devices described for (2000), which are used by the SYSTEM as part of final process verification of container with medication before being dispensed by AADVS vending module to authorized CUSTOMER, including (11, 13).

2032—CUSTOMER interface components of the AADVS vending module, including (5,10,16). Configuration of the interface components includes: ID reader; credit card reader, touch-screen; control buttons, including button for requesting assistance from PROVIDER.

In general, configuration of the AADVS components include configurations which support AADVS SYSTEM configurations, including SYSTEMS with the following key features described below.

Carrier support conveyor inside each Portable Vending Cartridge (PVC) can be configured to support multiple number of tracks, with the number of tracks limited only by available physical size, weight and costs. Also includes carrier conveyors with single and multi-pocket carriers, with each pocket configured to support required item(s), container, bag with item(s). Each pocket of a carrier can be subjected to track-specific process control, including: environmental, loading and unloading methods. Carrier support conveyor can be configured to support horizontal, vertical and combination of horizontal and vertical layouts. Conveyor can be based on flexible belt, including timing belt. Carrier support conveyor can be configured to support required capacity by utilization of single and multiple carrier support conveyors. Carrier support conveyor can be configured to operate with a single drive pulley, or combination of drive and support pulleys.

Automatic Vending Module (AVM) can be configured to accept a number of Portable Vending Cartridges (PVC), with the number of cartridges limited by physical size, weight and costs. The number and indexing of each PVC inside AVM can be configured to include: PVC only with horizontal index; PVC only with vertical index; combination of PVC's, with some having horizontal index, and some having vertical index. Example: Front of AVM can be configured to have insertable PVC with vertical index, while the back side— configured to accept slide-able PVC's with horizontal index. Loading of items into the carriers can be configured to support: remote loading via Portable Vending Cartridges (PVC); on-site local loading; and combination of both. Dispensing of items can be configured to include: multi-item dispensing on Customer side; simultaneous multi-tem dispensing on Customer and Provider sides. Depending on number of PVC installed and number of static conveyor assemblies installed, dispensing is configured to provide convenient access to items being dispensed from all carrier conveyors. As needed, the section of AVM designated for provider—can be located and sealed behind the pharmacy walls, or kiosk structure, while the section of AVM designated for customer, specifically—user interfaces and dispensed items pick-up bin—are exposed to customers for convenience. Dispensing via slide-able tunnel is described in the application. AADVS controllers located inside various components (PVC, AVM, etc.)—are interfaced via LAN with the Host controller, and operation of each component, as needed, can be coordinated in real-time directly by the Host controller with and/or without operator assistance. AADVS control QUALITY ALGORITHM includes operation criteria, such as: optimization using available resources; sustaining required quality of operations; sustaining quality of items being processed; providing maximum rate of service to customers. Conveyor timing belt inside Portable Vending Cartridges (PVC) can be configured with: either permanently embedded or removable (pluggable) carrier support bearings; permanently embedded index slots; and permanently embedded rollers to reduce friction. Carrier support conveyor can be configured with multiple number of tracks, with the number of tracks limited only by available physical size, weight and costs. Carrier support conveyor can be configures with a variety of layouts, including: horizontal and vertical track layouts, with single belt, multi-belt, synchronized and non-synchronized configurations. Carriers are configured along the conveyor belt, as needed, including providing required space ("index dead zone", i.e. no carrier present is allowed) for convenient conveyor mounting of a configuration consisting of a single conveyor belt in the middle and carriers supported from bearing assemblies indexed on each side of the conveyor, forming a single belt dual track configuration. Carrier support conveyor required capacity can be achieved by utilization of multiple carrier support conveyors. Simple closed-loop dual pulley driven carrier conveyors will improve reliability, lower noise. Portable Vending Cartridge (PVC) can be configured with: one conveyor belt and one pulley; one conveyor belt and 2 pulleys; multiple conveyor belts with multiple number of pulleys. In addition, PVC can be configured with motorized conveyor, self-contained; or with conveyor only, while the motor drive located inside the mating slot of an Automatic Vending Module (AVM), which will engage with conveyor upon inserting of PVC into mating slot of AVM. Portable Vending Cartridge can be configured with: horizontal conveyors; or vertical conveyors. Automatic Vending Module can be configured to accept a number of slideably insertable PVC units, each with unique configuration, including: PVC with horizontal conveyors and PVC with vertical conveyors. The carrier conveyor inside PVC can be configured to support and index carriers, empty or loaded with items. Carrier conveyor can be configured as: single conveyor belt with dual track, one track of carriers on each side of the conveyor belt, sharing one carrier support bearing assembly; dual conveyor belt with single track in-between, with carriers supported from each side via respective carrier support bearing assembly; multi-conveyor belt with multi-track of carriers. Carrier conveyor can be aligned horizontally, vertically, or combination of two—sections with horizontal and vertical indexes. In its simplest configuration, a carrier conveyor will consist of one conveyor belt with embedded or fasten-in carrier support bearing assemblies; drive/support pulley; and support mechanics for pulleys, mechanical couplings. In this case, the conveyor drive mechanics (motor, mechanical couplings) and control electronics will reside inside the mating slot of the Automatic Vending Module (AVM), which will engage with the carrier conveyor when respective PVC containing the conveyor will be inserted into the slot. Carrier conveyor can be configured to support any combination of carriers, including: carriers of different sizes; carriers with single and multiple pockets. AADVS can be configured to match requirements of a specific pharmacy, providing:

1) Superior throughput. An automatic vending module (AVM) can be configured to contain: multiple independent portable vending cartridges (PVC), which when installed inside the module, would form a multi-track horizontal and vertical carrier transport system, capable of simultaneous loading and/or unloading of a number of items; static built-in multi-track conveyors, which are installed along the perimeter of the vending module, surrounding portable vending cartridges. For example, a vending module configured with: three (3) independent portable vending cartridges, each configured as a 3-track carrier transport conveyor, and two static conveyors installed along the perimeter—can allow simultaneous loading and/or unloading of 22 items at designated pickup bins located along the perimeter of the module. As result, the AADVS will outperform any vending system ever configured.

2) Superior QUALITY and PROCESS controls, such as: simultaneous inspection of carriers and items inside carriers, simultaneous tracking of carriers and items inside carriers; simultaneous item processing, etc. to be conducted simultaneously along multiple tracks, which can be controlled by AADVS Controllers, including in synch or independent operations.

3) Superior safety and security monitoring and verifications of the MEDICATIONS inside AADVS SYSTEM.

4) Complete real-time, independent of operator, closed loop control of all process steps by controller. 100% guaranteed quality of prescription medications is accomplished initially by using AADVS Controller and components:
   a) Verification of prescription entered by Provider, AADVS Controller will identify: respective container to store the prescription based on medication specifications (solid or liquid, temperature, humidity, unit weight, total weight) (size, weight, capacity); and calculate the expected combined weight of the container with correct amount of medication inside selected container
   b) Provider will follow directions from AADVS Controller and will select appropriate container for storing medications
   c) Provider using AADVS components will measure weight and size of the container with filed prescription medication, and AADVS Controller will perform initial validation of these parameters to match the respective specification entered by Provider into non-volatile memory under identification record, such as barcode, attached to the container with medication, and will record and store the validated information under prescription barcode label code, attached to the container with medications
   d) While within AADVS, each container with medication inside, will be periodically inspected by Controller for verification of: weight, size of the container to match the barcode label on the container
   e) AADVS components, such as Portable Vending Cartridges (PVC), Automatic Vending Modules (AVM) will have quality inspection devices, such as: barcode readers, configured to be located at required inspection points, including: entry, transfer in-between sub-assemblies, prior-to-dispense (final verification); weight measuring scales, which can be configured to measure the weight of: each container individually, conveyor assembly with carriers, transfer sub-assemblies; size measuring devices (optical, etc.), which can be configured to measure the size of: each container as it passes check points along the conveyor assembly, at transfer points in-between sub-assemblies—with an objective to monitor specifications parameters of the container with medications per information stored by AADVS Controller based on barcode label attached to the container, and ensure it is maintained within specifications prior to dispensing to authorized Customer. The containers, which failed inspection, will be rejected by AADVS Controller, and as configured by Provider—will be dispensed back to the Provider.

5) The design of AADVS can be configured with appropriate thermal isolation or insulation of heat generating components (motors, drives) from Carrier section inside Portable Vending Cartridges (PVC), and will support automatic dispensing of medications, which are maintained within respective environmental specifications (temperature, humidity) at all times. In addition, sections of the Automatic Vending Modules (AVM) containing medications inside installed PVC units, can be configured with thermal isolation, or insulation, or combination of both, and can be further configured to be enclosed structurally to allow portable environmental control devices, such as: temperature controllers, humidity controllers—to maintain all medications inside (AVM) within specified environment at all times.

AADVS supports variety or configurations, which include specific configurations for each individual component, and combination of configurations for any given system to meet specific requirements. In addition, other AADVS support components provide the following functions: Automated Container loading and unloading; Dispensed Container packing, etc. Operation of all components within Automatic Distributed Vending System for Pharmacy (AADVS) is synchronized in real-time by local and remote Controllers to achieve the most efficient, safe, reliable and cost-effective operations at all times. The AADVS can be configured for direct synchronization by Controllers without operator assistance, or combination of direct and operator controls. When configured for direct, the remote or host AADVS Controller will synchronize with all respective stand-alone Controllers and AVM Controllers to monitor and control in real-time a number of functions, including: status, inventory. Status will include: location, availability, operating condition, environment. Inventory will include: equipment, stored medications inside. Inventory will be monitored via local controllers connected to respective sensors, including: barcode, RFID. Status will be monitored via local controllers connected to respective sensors, including; environment, safety. Synchronization control will include support of: centralized processing of prescription medications, on-site processing of prescription medications, and combination of both. Synchronization control will optimize processing of prescription medications, including: location, date/time, selected PVC, selected available carrier within PVC, distribution to selected AVM—to ensure quality and efficiency of all process and logistics steps at all time. In respect to a specific AADVS layout, remote or host Controller will monitor and control in real-time: the number, location, status of available equipment (AVM, PVC, support components, etc.); inventory of each AVM (number of PVC installed); inventory of each PVC components (number of carriers, status of carriers); inventory of each PVC content (number of medications, medications ID barcode). Controllers will also monitor and control status of medications within the AADVS, including: expiration date, environment, weight, location, status (request date/time, location). AADVS Controllers will synchronize the inventory and status information to ensure: required medications within respective specifications are available for dispensing to authorized Customers at specified locations and time; connective controls are executed in real-time to ensure that only medications within their specifications are dispensed to authorized Customers. In respect to operation of AVM, Controller will synchronize operation of each PVC inside AVM, to ensure: Carrier Conveyors are synchronized to maintain required alignment and position accuracy; quality of each medication stored inside PVC is maintained within specifications (environment, safety, expiration, weight). In addition, AVM Controller will synchronize operation of all PVC's inside AVM, to ensure: safe, reliable and efficient operation of respective Carrier Conveyors. AVM Controller will start each Conveyor after a short delay from the start time of another Conveyor within AVM, to avoid peak demands in electrical power. Controller will align selected Carriers for loading of medications. Controller will align selected Carriers for unloading of medications, and when unloading Sliding Tunnel is used, Controller will synchronize operation of all Carrier Conveyors inside each PVC installed in the AVM to ensure: only selected Carriers with inspected medications inside are presented for unloading; dispensing rate of several medications to an authorized Customer is completed within shortest time possible.

Figure 2:
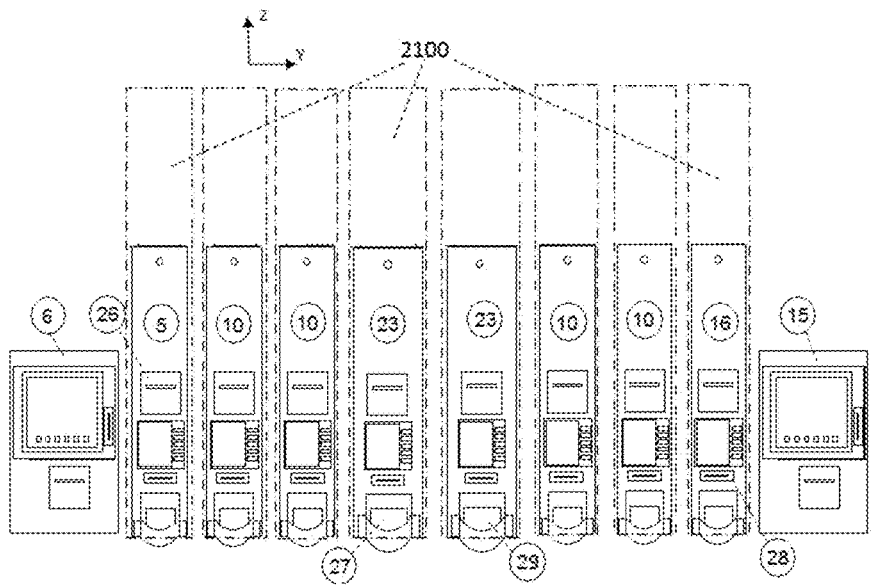

FIG. 2—illustrates Z-Y view of a pharmacy configured using Automatic Distributed Vending System (AADVS) with integrated QUALITY control ALGORITHM. For simplicity, the configuration shown is for a stand-alone pharmacy, responsible for preparation, storage, distribution, and dispensing of MEDICATIONS and/or accessories for a PATIENT-specific environment, abbreviated as AADVS-Ps. The AADVS vending modules (5,10,16,23) are configured to support AADVS-Ps, and are further configured for supporting:
1) Variety of sizes of MEDICATIONS, for optimum utilization of the space inside the modules, and available space allocated within the pharmacy. As illustrated, module (5)—smallest size, modules (10)—medium size, module (16)—large size, module (23)—extra-large size.
2) Vertical conveyor indexing system of carriers, which is shown by module outline (2100). The vertical indexing will use the space from the floor level of the pharmacy to the very top of the ceiling of the pharmacy, maximizing use of available space vertically, while optimizing the required space horizontally.
3) Dispensing of quality MEDICATIONS at the floor level of the pharmacy to authorized CUSTOMERS.

The AVM modules will include respective AADVS components in support of AADVS QUALITY control ALGORITHM, including components (2002, 2003, 2016, 2025) illustrated and described for FIG. 1, and not shown here for simplicity. Remaining figure elements are labeled as follows:

6, 15—AADVS Station Controller #1 and #2, as described for FIG. 1

26—Module printer

28—Module card reader, which can accept ID cards, ATM/credit cards

29—Item Pick-up Bin, Customer side

Other AADVS components illustrated and described on FIG. 1 (not shown here for simplicity), can be configured and installed in support of AADVS QUALITY control ALGORITHM.

FIG. 3—illustrates Z-Y view of (1106) AADVS Automatic Vending Module (AVM). The AVM (1006) is further configured as AVM (2004), and includes AADVS components (2009, 2010, 2011, 2012, 2013, 2017) supporting integration of the AADVS QUALITY control ALGORITHM. For illustration purposes, the AVM (2004) configuration consists of 2 sections (1007). The upper section (1007) of (2004) is configured for operation with (2005) Portable Vending Cartridge (PVC), and the lower section (1007) of (2004) is configured for operation with PVC (2006). The PVC (2005) and PVC (2006) are configured with a single track dual belt in general, the AVM units, such as (2004), can be configured with variety of features described in my patents and in this application. AVM parameters, including: dimensions; number of sections in support of required number of PVC's; layout of each section in support of specific configuration of the mating PVC to be installed; methods of inserting PVC into a meting section; methods of sustaining ITEMS inside installed PVC's; methods of dispensing ITEMS from installed PVC's; methods of interfaces for PROVIDER and CUSTOMER; methods of interfacing with AADVS controllers—are configured to support required operation under AADVS QUALITY control ALGORITHM. Remaining figure elements are labeled:

60—Conveyor Carrier assembly (not all components are shown)

2007—CONTAINER with MEDICATION inside a CARRIER (2008), which is positioned inside one of the CARRIER (as shown) for PVC (2006). The location of the identification barcode label (not shown for simplicity) attached to the CONTAINER (2007), and respective loading and position of the CONTAINER (2007) inside the CARRIER (2008) is in compliance with the AADVS QUALITY control requirements to allow the QUALITY control ALGORITHM using barcode sensors (2009, 2010) to verify the information presented on these barcode labels. Example of acceptable configuration: the barcode label of the CONTAINER (2007) loaded inside (2008) is facing up in respect to Z-axis, just as the barcode labels attached to (2008), and are reliably identified by respective barcode reading devices (2009, 2010) aligned down along the Z-axis.

2008—Same as (60), which is configured with barcode labels (not shown for simplicity) in support of AADVS QUALITY control. The number and location of the barcode labels for (2008) complies with respective QUALITY process verification requirements. For example: the barcode label for identification of the (2008) can be placed on one or both (Y-axis) ledges of the CARRIER, as shown and described for FIGS. 8-9, while the evenly spaced bars barcode label, such as (2014) shown on FIG. 10, can be placed along the Y-axis in the center of the bottom portion of the CARRIER.

2009—AADVS components or devices of AADVS PVC (2005), including sensors, which are configured by AADVS QUALITY control for verifications of barcode labels and size of an object. The AADVS barcode reading devices are used for verification of: barcode label attached to an object, and for measuring the length of an object, as illustrated and described for FIG. 19.

2010—Same as (2009) for AADVS PVC (2006).

The AADVS components (2009, 2010) and the AADVS QUALITY control can be configured to perform STATIC and/or DYNAMIC verifications of barcode labels attached to a CARRIER (2008) and barcode label(s) attached to CONTAINER with MEDICATION (2007) inside a (2008). STATIC verification includes the AADVS conveyor advancing and holding (not moving) the respective CARRIER (2008) to a specified position under respectively (2009, 20010), and activating the respective (2009, 2010) to obtain information of the barcode labels attached to (2008) and also obtain information of the barcode label(s) attached to (2007), when the (2007) is present inside the (2008). DYNAMIC verification includes the AADVS conveyor advancing, including moving at regular speed, or lowered speed, the respective CARRIER (2008) to a specified position under respectively (2009, 20010), and activating the respective (2009, 2010) to obtain information of the barcode labels attached to (2008) and also obtain information of the barcode label(s) attached to (2007), when the (2007) is present inside the (2008). The AADVS controllers via respective SENSORS maintain in real-time information of the location of the respective components within AADVS, including: position of the CARRIER conveyor; position of each CARRIER; position of respective SENSORS. The timing of activating the respective barcode reading devices (2009, 2010) will be based on AADVS detecting presence of the respective components, such as (2008, 2007) within the operating window of the respective SENSORS (2009, 2010), and then activating (2009, 2010) to obtain barcode information as described above. The obtained information from the respective barcode labels attached to the CARRIER (2008) will be used by AADVS QUALITY control to verify via respective barcode sensors (2009, 2010): identity of (2008); status of (2008), including EMPTY status if none of barcode labels are blocked. The obtained information from the respective barcode labels attached to the MEDICATION (2007) will be used by AADVS QUALITY control to verify via respective barcode sensors (2009, 2010): identity of (2007); length of the (2007) along the Y-axis.

2011—AADVS components or devices of AADVS AVM (2004), including sensors, which are configured by AADVS QUALITY control for verifications of the weight of the AADVS PVC (2005 in the example) loaded into the upper section (1007).

2012—Same as (2011) for measuring weight of AADVS PVC (2006 in example) loaded into lower section (1007).

2013—AADVS components or devices of AADVS AVM (2004), including sensors, which are configured by AADVS QUALITY control for verifications of the weight of the AADVS AVM (2004).

2016—AADVS components or devices of AADVS AVM (2004), including sensors, which are configured by AADVS QUALITY control for verifications of the SECURITY of AADVS AVM (2004). The configurations of AADVS components (2016) includes sensors for monitoring the status of the panels enclosing the AADVS AVM (2004).

2017—AADVS components or devices of AADVS PVC (2005, 2006), including sensors, which are configured by AADVS QUALITY control for verifications of the SECURITY of AADVS PVC (2005, 2006). The configurations of AADVS components (2017) includes sensors for monitoring the status of the panels enclosing the AADVS PVC (2005, 2006).

1104—Available space inside AVM (1106) which can be used for installation of components such as: Controllers, PSU, LAN interfaces, USB interfaces, environmental controllers, etc.

Figures 4, 5:
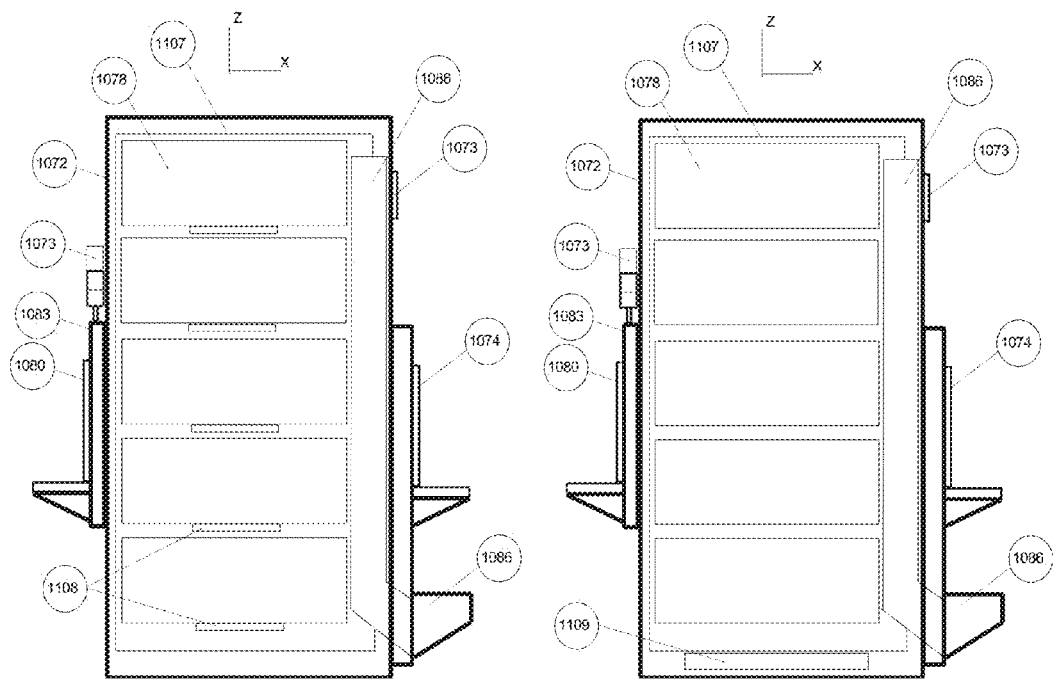

FIG. 4—illustrates Z-X view of (1072) AADVS Automatic Vending Module (AVM), configured with scale components (1108), which are connected to Controller for real-time measurements of the weight of each PVC (1078) installed inside AVM (1072). Loading of items into each PVC (1078) inside AVM (1072), or unloading of items from PVC (1078), will be verified by controller in real-time by monitoring the respective scales and detecting change in weight. The Controller based on item identification, such as barcode label, will obtain the item expected weight from the non-volatile memory, and compare to detected change in weight. If the change in weight is within predefined tolerances, and was expected, then the controller can make the item available for dispensing to Customer. If the change in weight is unexpected, Controller in real-time will execute pre-configured correction actions, as part of apparatus configurations parameters. Correction action can be configured to include: informing Provider vie available interfaces (audio/visual/electronic) of PVC with violation in weight; returning items beck to Provider. The AVM and each PVC will include respective AADVS components in support of AADVS QUALITY control ALGORITHM, including components (2002, 2003, 2016, 2025) illustrated and described for FIG. 1, and not shown here for simplicity. Elements labeled as follows:

1074—User interface controller. Customer side

1075—Item pick-up bin, form which the authorized CUSTOMERS will receive dispensed MEDICATION 1078—PVC. As shown—qty. 5 of PVC's are installed into AVM (1072)

1079—Status indicator for AVM (1072)

1080—Provider interface controller for AVM (1072)

1083—Mounting platform supporting user interfaces for the PROVIDER, and which can be configured to rotate around Z-axis 1086—Item dispensing and delivering tunnel. Items dispensed from each PVC inside AVM are entering the tunnel and then roll down to the pick-up bin (1075)

1108—AADVS components or devices of AADVS AVM (1072), including sensors, which are configured by AADVS QUALITY control for verifications of the weight of each of the AADVS PVC modules loaded into (1072).

FIG. 5—illustrates Z-X view of assembled AVM (1072), shown on FIG. 4, configured with one scale component (1109), which is connected to Controller for real-time measurements of the weight of all PVC (1078) installed inside AVM (1072). Loading of items into AVM, or unloading of items from AVM will be verified by controller in real-time by monitoring the scale (1109) and detecting change in weight. The Controller based on item identification, such as barcode label, will obtain item expected weight from the non-volatile memory, and compare to detected change in weight. If the change in weight is within predefined tolerances, and was expected, then the controller can make the item available for dispensing to Customer. If the change in weight is unexpected, Controller in real-time will execute pre-configured correction actions, as part of apparatus configurations parameters. Correction action can be configured to include: informing Provider via available interfaces (audiovisual/electronic) of PVC with violation in weight; returning items back to Provider. The AVM and each PVC will include respective AADVS components in support of AADVS QUALITY control ALGORITHM, including components (2002, 2003, 2016, 2025) illustrated and described for FIG. 1, and not shown here for simplicity. Remaining elements are labeled same as on FIGS. 3-4

Figures 6, 7:
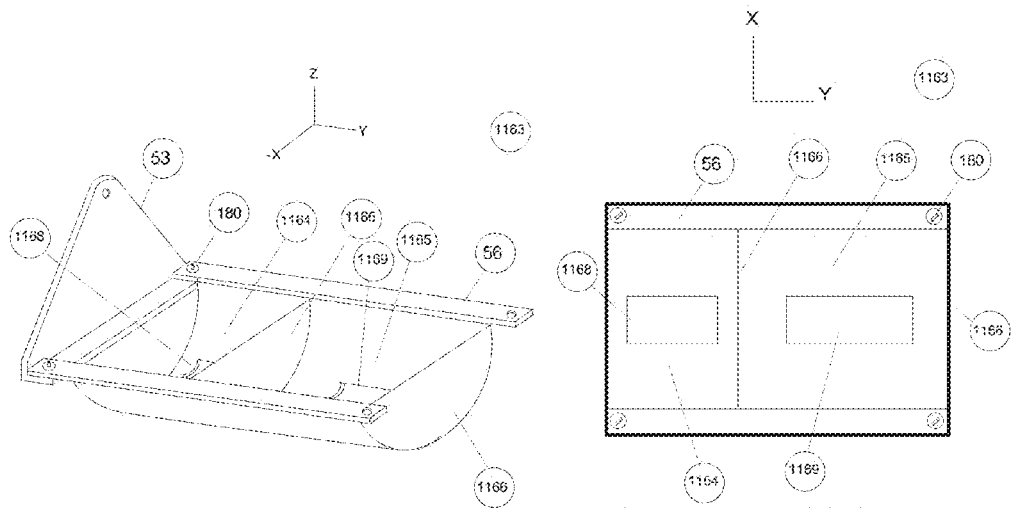

FIG. 6—illustrates X-Y-Z view of section of a carrier (1163). The configurations for a CARRIER include: single pocket configurations for storing and transporting a single CONTAINER with MEDICATION; and a multi-pocket configurations with individual pockets configured for storing individual CONTAINER with MEDICATION. The CARRIER (1163) illustrates a configuration of a dual pocket, with smaller pocket (1164) and larger pocket (1165). Figure elements are labeled as follows:

53—Part of carrier support assembly (only one shown for simplicity)

56—One of Carrier holding assembly platforms, which can be used for placing barcode label(s).

Barcode label can contain information related to Carrier.

180—One of mounting screws for securing position of Carrier holding plate

1184—Pocket #1 of the carrier used for holding and transporting item of respective size and shape 1165—Pocket #2 of the carrier used for holding and transporting item of respective size and shape 1166—Carrier pocket side wall 1168—Barcode label in the base of Pocket #1, which can be configured for measuring the size of a CONTAINER placed inside the POCKET #1.

1169—Barcode label in the base of Pocket #2, which can be configured for measuring the size of a CONTAINER placed inside the POCKET #2.

FIG. 7—illustrates X-Y view section of a carrier (1163) shown on FIG. 6. Elements labeled same as FIG. 6

Figures 8, 9, 10:
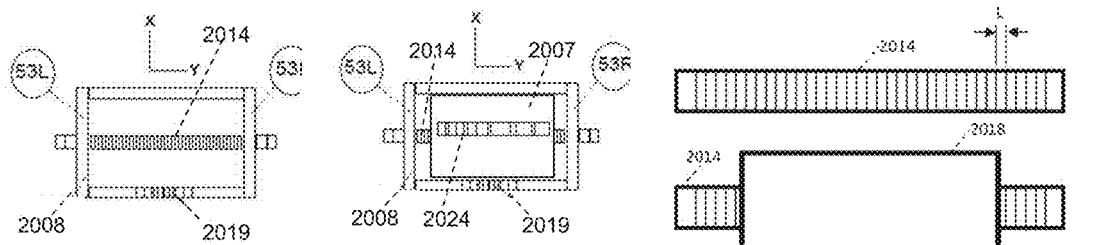

FIG. 8—Top view of the empty Carrier (2008). Figure elements are labeled as follows:
- 53L—Carrier support assembly, left side
- 53R—Carrier support assembly, right side
- 2014—Barcode label located at the bottom of the Carrier (2008), and is configured for measuring size along the Y-axis of a CONTAINER placed inside the CARRIER (2008). Details illustrated and described for FIG. 10. This barcode label will be covered by Item or Container loaded inside the Carrier. This fact can be detected by respective AADVS Controller, and can be used by Controller to verify or establish if respective Carrier is loaded or not, and also used by AADVS computer(s) for overall real-time inventory management of available capacity of empty Carriers with an objective to optimize their loading to achieve prompt availability of specified Items at designated locations.
- 2019—Carrier barcode label located on top of one of the Carrier side ledges. As needed, the same label can be installed on the opposite ledge of the CARRIER. This barcode label can be used by respective AADVS Controller and AADVS QUALITY control for continuous verification of status of respective Carrier within the system. Barcode label can be configured to contain information about the Carrier. The information can include Carrier parameters, which can be used by AADVS for proper identification and usage of the Carrier for respective range of Items or Containers.

FIG. 9—Top view of the Carrier shown on FIG. 8 with loaded Container (2007) inside. The container (2007) can be filed with medications. The CONTAINER (2007) can be configured with a barcode label (2024), containing parameters, including parameters in respect to specifications of the MEDICATIONS located inside the CONTAINER. The CONTAINER (2007) is loaded per AADVS requirements, including the requirement of orientation of the CONTAINER in respect to the barcode label (2024) facing up toward the Z-axis. In general, in respect to AADVS SYSTEM monitoring and processing barcode labels, the location and configuration of:
- a) Barcode labels attached to: AADVS components, such as CARRIERS;
- b) Barcode labels placed on ITEMS, such as CONTAINERS loaded into the AADVS carriers;
- c) ITEMS within AADVS, including the ITEM orientation within AADVS, such as CONTAINERS loaded into AADVS CARRIERS;
- d) Barcode reading devices designated for detecting and reading the barcode labels listed in (a-c);

are all will comply with AADVS requirements, including the requirements for reliable reading of the respective barcode labels by the respective AADVS barcode reading devices, including DYNAMIC barcode reading, when ITEM with a barcode label is moving, such as CONTAINER inside a CARRIER being advanced by AADVS conveyor; and STATIC reading when a non-moving ITEM with barcode label is aligned to present its barcode label to a respective barcode reading device. Figure elements are labeled same as on FIG. 8

FIG. 10—illustrates example of an even bar spaced (length L in-between the bars) barcode label (2014) with a resolution of L for measuring length of a container (2018) placed on top of the surface to which the label (2014) is attached. The length of the container (2018) will be calculated as follows: $L(2018)=(N-1)\times L$, where N—number of consecutive bars blocked by the container (2018). As shown, the $L(2018)=25\times L$.

Figure 11:
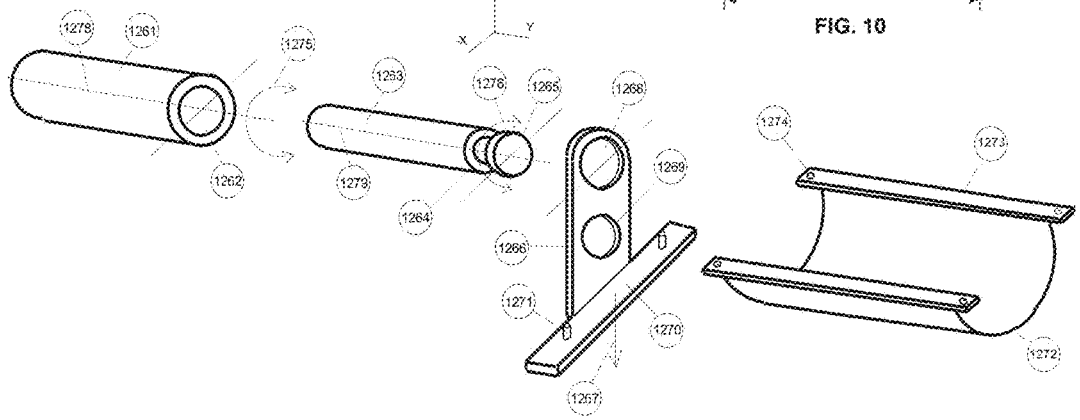

FIG. 11—Illustrates configuration of a support for a carrier (1272) which enables the carrier (1272) to swing in direction (1275) about the primary axis (1278) of the bearing (1261), and independently swing in direction (1276) about the secondary axis (1279) of the carrier support shaft (1263). For simplicity, only one side of the carrier support is illustrated. For small and light items, and respectively small and light carriers, the support for the carriers can be configured from one side only, with the opposite side being suspended in the air. The independent dual axis rotational support (referenced for simplicity as "dual axis support") illustrated will reduce friction for the carrier to swing about the primary axis (1278), which will in-turn reduce required forces required to be applied to the carrier (1272) in order to swing required angle in respect to the primary axis (1278), or Y-axis, and allow the item originally located inside the carrier (1278) to roll-out for dispensing. The "dual axis support" is applied for dispensing via sliding tunnel, as described on FIG. 13. FIG. 13. Figure elements:
- 1262—Cavity of (1261) configured with an inner race into which the carrier support shaft (1263) of the item carrier is inserted, allowing the item carrier to swing in direction (1275) about the axis (1278) of the inner race
- 1264—Slot in the carrier support shaft (1263) configured to accept a carrier support bracket (1266) and allow the carrier support bracket (1266) together with attached carrier to swing in direction (1276) about the axis (1279) of the carrier support shaft (1263)
- 1269—Opening in the support bracket (1266) as illustration of removing extra materials to reduce weight
- 1270—Platform of carrier support bracket (1266) configured to provide support for item carrier base (1272)
- 1271—Holding pin or threaded stud of (1270) configured to accept or mate the mounting opening (1274) of the item carrier base (1272)
- 1273—Section of carrier base (1272) configured for mounting the carrier (1272) to support bracket (1266). This section can be used for placement of a barcode label with information about the carrier (1272).

Figure 12:
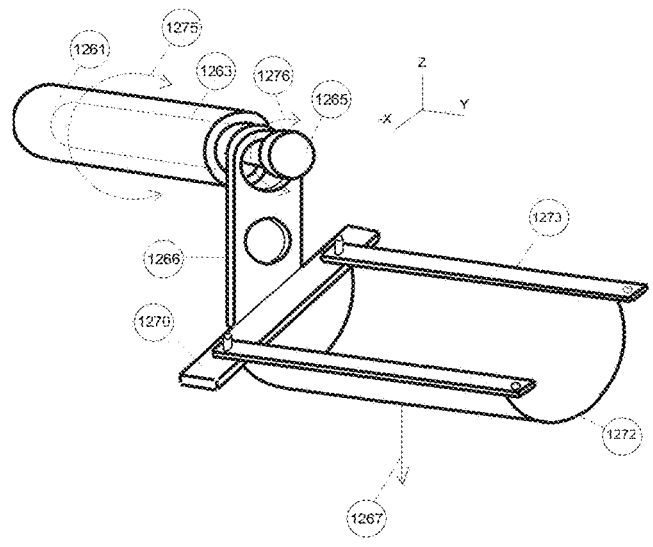

FIG. 12—Illustrates assembled carrier (1272) supported from the cavity (1264) of the shaft (1263) inserted into inner race of the bearing (1261). For simplicity, the conveyor belt to which the bearing (1261) is attached is not shown. The illustrated mounting will enable carrier (1272) together with support bracket (1266) to swing in direction (1275) about the primary axis (1278) of the bearing (1261), and independently swing in direction (1276) about the secondary axis (1279) of the support shaft (1263). For simplicity, only one side of the carrier support is illustrated. For small and light items, and respectively small and light carriers, the support for the carriers can be configured from one side only, with the opposite side being suspended in the air. The independent dual axis rotational support (referenced for simplicity as "dual axis support") illustrated will reduce friction for the carrier to swing about the primary axis (1278), which will in-turn reduce required forces required to be applied to the carrier (1272) in order to swing required angle in respect to the primary axis (1278), or Y-axis, and allow the item originally located inside the carrier (1278) to roll-out for dispensing. Additional bracket can be configured to restrict the support bracket (1266) during transportation or as needed, from exiting the slot (1264) of the support shaft (1263). The "dual axis support" illustrated, can be applied for dispensing items from carriers via sliding tunnel, as described on FIG. 13.

FIG. 13—Illustrates AADVS Automatic Vending Module (AVM) (1072) configured with 5 installed Portable Vending Cartridges (PVC) (1078), with a Slide-able Unloading Tunnel (SUT) (1248). For simplicity, the AADVS components on FIGS. 13-15 are shown in a format of a diagram, which is intended to illustrate the principals in respect to unloading the content from respective carriers using Slide-able Unloading Tunnel (1248).

FIG. 13 is copied from FIG. 124 of the document DRAWINGS and described in details in the document SPECIFICATIONS, both documents listed in the U.S. Pat. No. 8,954,190 "Optimization of Pharmacy Operations using Automatic Distributed Vending System". The respective AADVS devices and components, including: weight measuring (1108); ID reading (1095); size measuring (1312); and security monitoring not show for simplicity—are all integrated into AADVS QUALITY control ALGORITHM as described in this patent.

FIG. 14—Illustrates Automatic Vending Module (AVM) (1072) configured with 5 installed Portable Vending Cartridges (PVC) (1078), shown on FIG. 13, with a Slide-able Unloading Tunnel (SUT) (1248) installed on Provider side, and is directed by controller to advance in direction (1249) toward unloading position, and engage its "Self-adjusting Plates" (1286) with respective carriers (1272) aligned by Controller for dispensing the items (1281) they contain. FIG. 14 is copied from FIG. 125 of the document DRAWINGS and described in details in the document SPECIFICATIONS, both documents listed in the U.S. Pat. No. 8,954,190 "Optimization of Pharmacy Operations using Automatic Distributed Vending System". The respective AADVS devices and components, including: weight measuring (1108); ID reading (1095); size measuring (1312); and security monitoring not show for simplicity—are all integrated into AADVS QUALITY control ALGORITHM as described in this patent.

FIG. 15—Illustrates Automatic Vending Module (AVM) (1072) configured with 5 installed Portable Vending Cartridges (PVC) (1078), shown on FIG. 14, with variation where a selected number of carriers (1272) with items (1281) inside selected PVC units are aligned for unloading on Customer side, and respectively—selected number of carriers (1272) with items (1280) inside selected PVC units are aligned for loading/unloading on Provider side. FIG. 15 is copied from FIG. 126 of the document DRAWINGS and described in details in the document SPECIFICATIONS, both documents listed in the U.S. Pat. No. 8,954,190 "Optimization of Pharmacy Operations using Automatic Distributed Vending System". The respective AADVS devices and components, including: weight measuring (1108); ID reading (1095); size measuring (1312); and security monitoring not show for simplicity—are all integrated into AADVS QUALITY control ALGORITHM as described in this patent.

Figure 16:
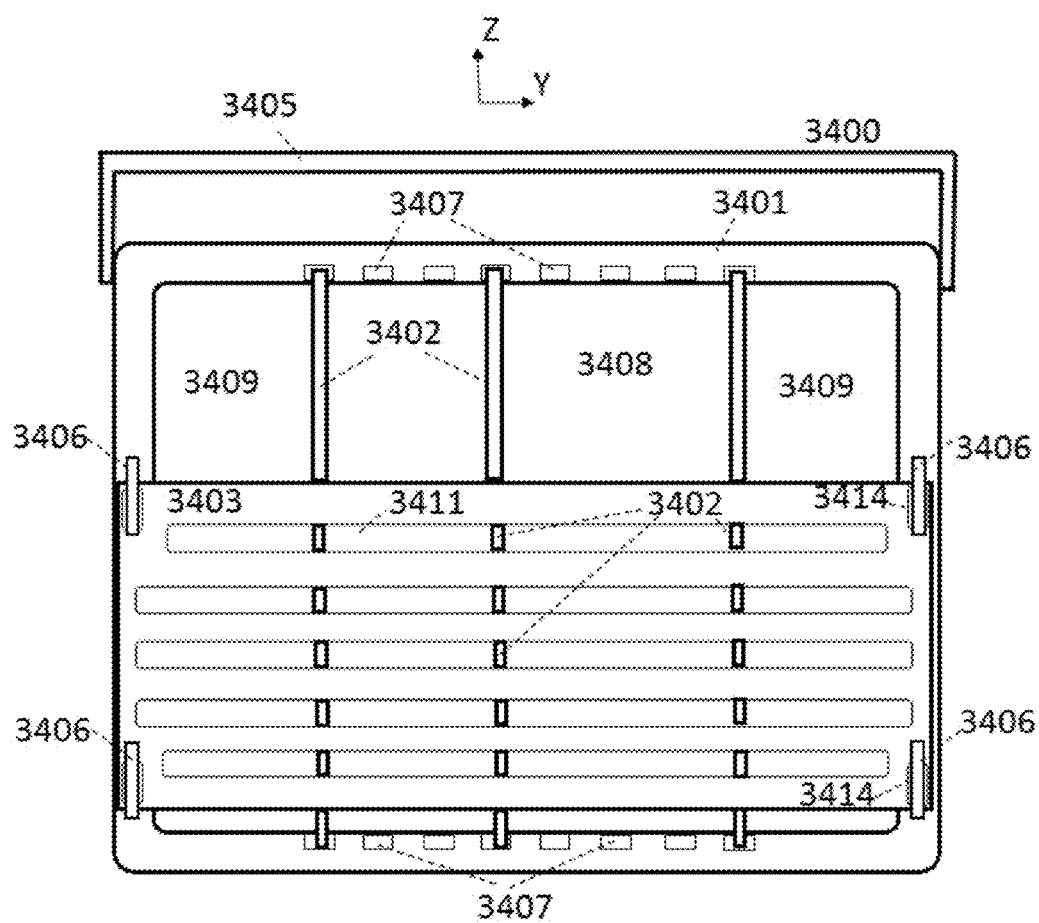

FIG. 16—illustrate a configurable multi-ITEM BASKET or TRAY (3400), which can be configured for: loading, housing, transporting and dispensing multiple CONTAINERS with PRESCRIPTION medications, including such medications containing pills, liquid. The shown configuration of the (3400) is symmetrical in respect to X-axis, meaning the front view shown and the back view are the same. The elements are labeled as follows:

3401—Configurable main FRAME of (3400) with SLOTS (3407) for inserting DIVIDER plates (3402) to create POCKETS, including POCKETS (3408, 3409) for medication CONTAINERS of various sizes, as needed

3403—Configurable front and back insert PLATES with slots (3414) configured to allow the (3403) to slide along Z-axis over the HOOKS (3406) of the (3401), and secure the (3403) in the position as shown, and as result, retaining CONTAINERS located inside the POCKETS of the (3400)

3411—Slots of the (3403) configured to reduce weight of the (3403), and allow OPERATOR to partially view ITEMS, which are stored in the POCKETS (3408, 3409) of the (3400) behind (3403).

3405—Configurable HANDLE attached to (3401), which is used by the OPERATOR to handle (3400), including loading and unloading of the (3400) into and out of the respective AADVS Conveyor CARRIERS.

Figure 17:
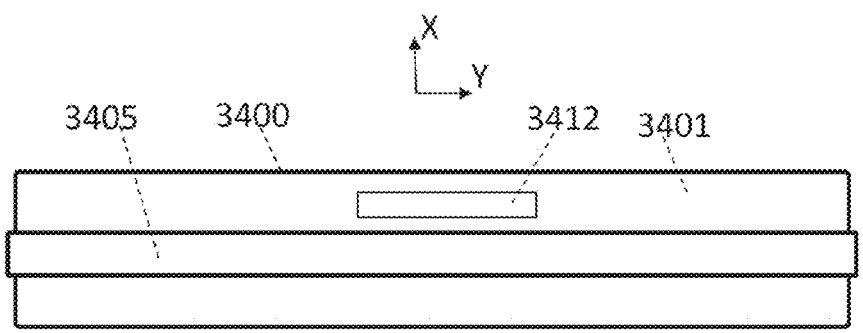

FIG. 17—illustrate X-Y view of the configurable multi-ITEM BASKET or TRAY (3400) shown on FIG. 16, with (3400) identification label (3412), which can be configured as type barcode, and which is attached to main FRAME (3401). The (3412) will be identified by the respective AADVS devices, and used by the AADVS QUALITY control ALGORITHM to monitor status of TRAYS within the AADVS.

Figure 18:
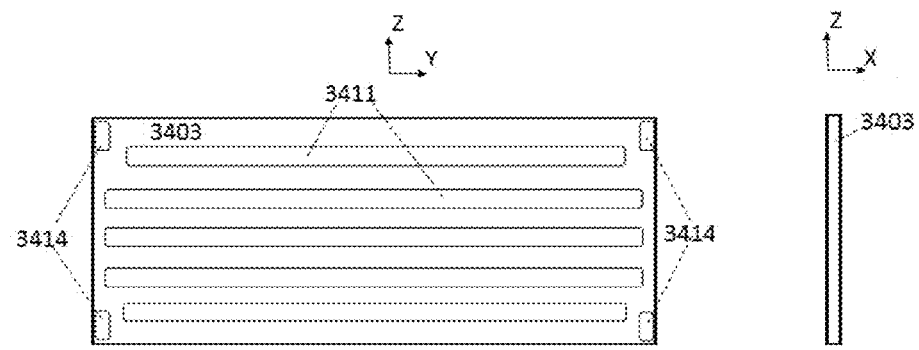

FIG. 18—illustrate views of the configurable insert PLATE (3403). Elements labeled same as on FIG. 16.

Figure 19:
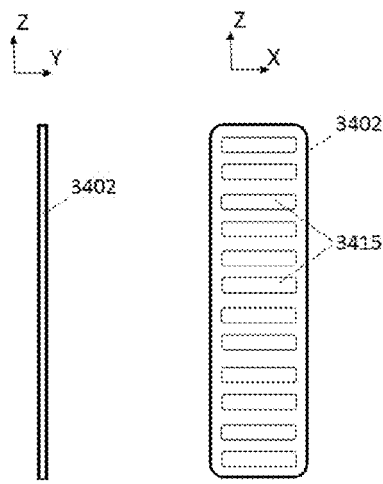

FIG. 19—illustrate views of the configurable DIVIDER plate (3402), which is configured with SLOTS (3415) to reduce its weight. The size and location of the SLOTS on this part and other parts will be configured to maximize reduction of weight, while retaining full functionality, including durability and reliability requirements.

Figure 20:
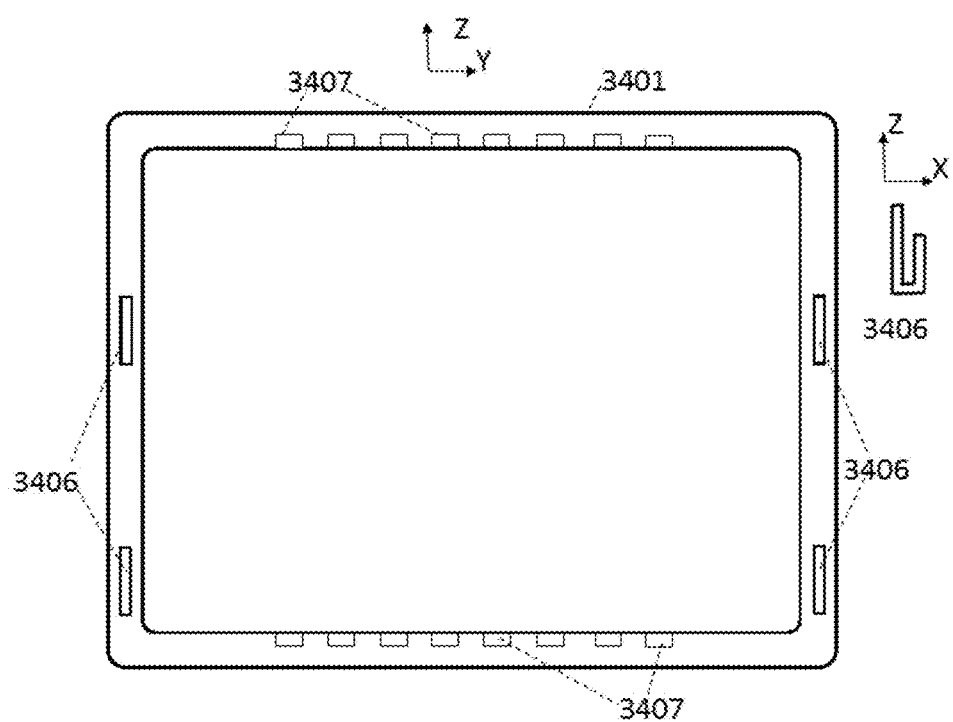

FIG. 20—illustrate configurable main FRAME (3401). Elements labeled same as on FIG. 16.

Figure 21:
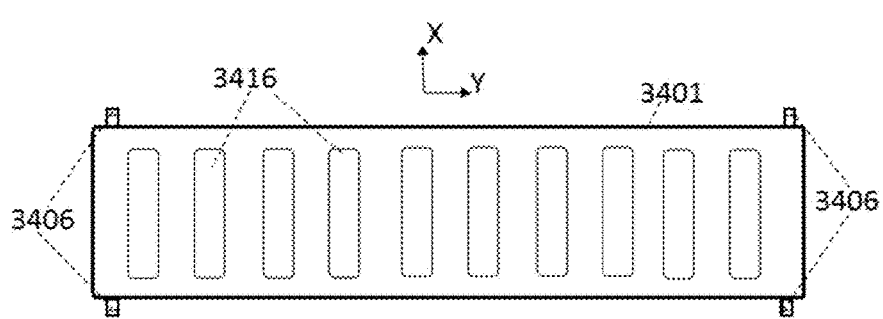

FIG. 21—illustrate X-Y view of the configurable main FRAME (3401), which is configured with slots (3416) to reduce its weight.

Figure 22:
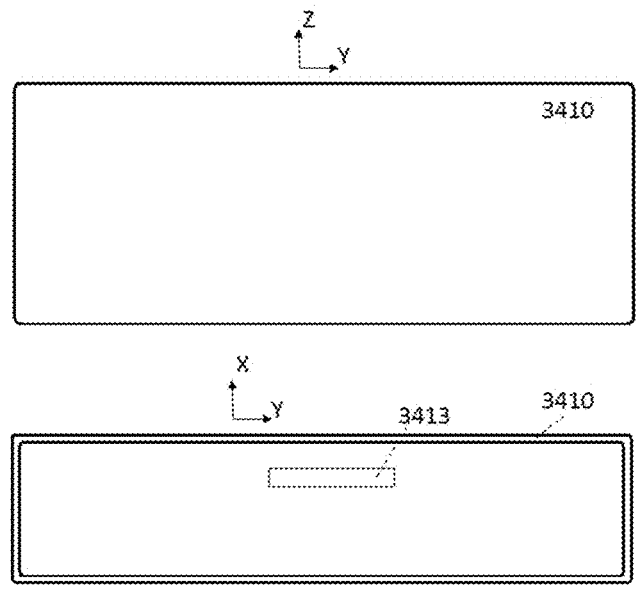

FIG. 22—illustrate views of an empty POCKET (3410) of a carrier. The POCKET (3410), when attached to a CARRIER of AADVS CONVEYOR, will be configured to accept, store and transport ITEMS, including ITEMS inside the multi-ITEM BASKET (3400). The (3413) is the carrier POCKET identification label which can be configured as type barcode, and which is attached to the bottom of the POCKET (3410). The (3413) will be identified by the respective AADVS devices, and used by the AADVS QUALITY control ALGORITHM to monitor status of CARRIERS with the POCKET such as (3410).

Figure 23:
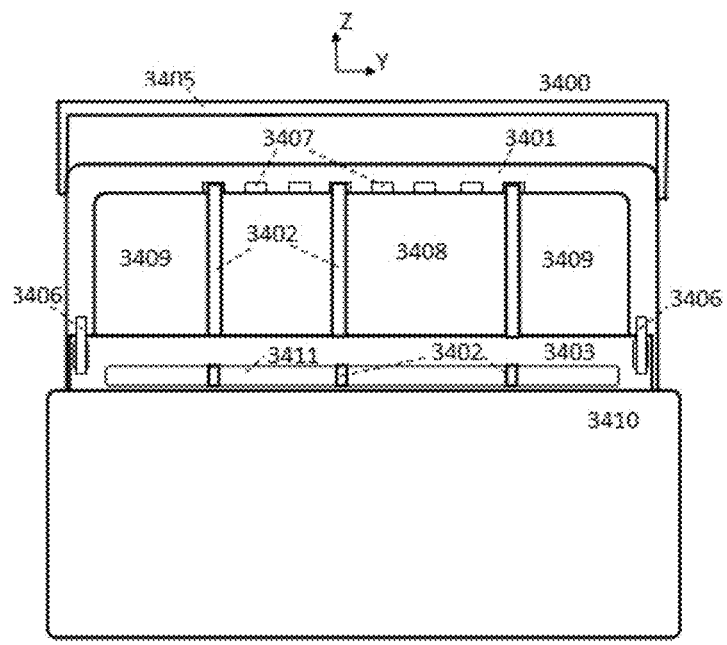

FIG. 23—illustrate Z-Y view of a carrier POCKET (3410) loaded with the multi-ITEM BASKET (3400). Elements are labeled same as on FIG. 16.

Figure 24:
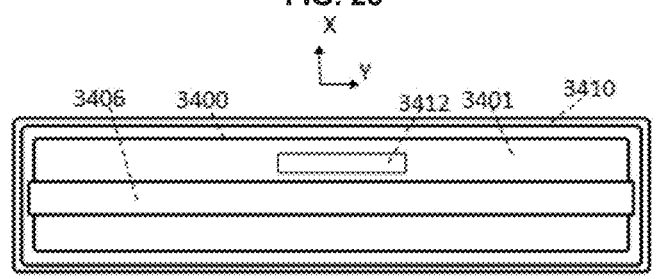

FIG. 24—illustrate X-Y view of a carrier POCKET (3410) loaded with the multi-ITEM BASKET (3400). Elements are labeled same as on FIG. 16 and FIG. 17.

Figure 25:
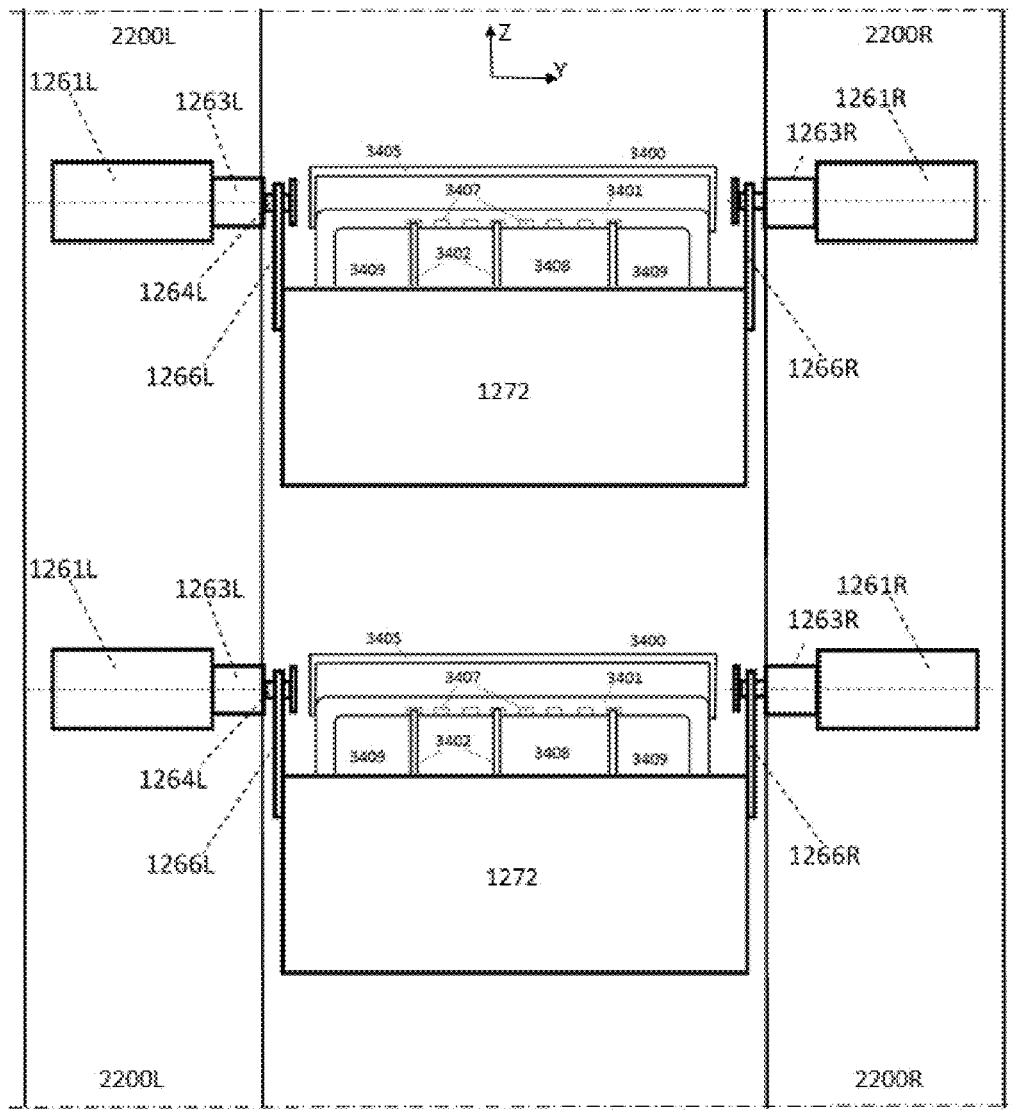

FIG. 25—illustrate Z-Y view of an AADVS carrier CONVEYOR (2200), which is configured with the following parameters: single closed loop transport TRACK; VERTICAL index; dual BELTS (2200L, 2200R) which can be configured with embedded or insertable BEARING assemblies (1261L, 1261R); each BEARING can be configured to support respective side of the item CARRIER (1272), which s described in details on FIGS. 11, 12; the CARRIER (1272) is loaded with the multi-ITEM BASKET (3400). When CONVEYOR (2200) is moving, the CARRIERS, supported from the BEARINGS of the BELTS of the CONVEYOR, will maintain essentially vertical alignment in respect to Z-axis, with insignificant swing angle around Y-axis, eliminating practically any vibrations experienced by the items stored inside the BASKET (3400). Remaining elements labeled as on FIG. 11, 12, 23.

Figure 26:
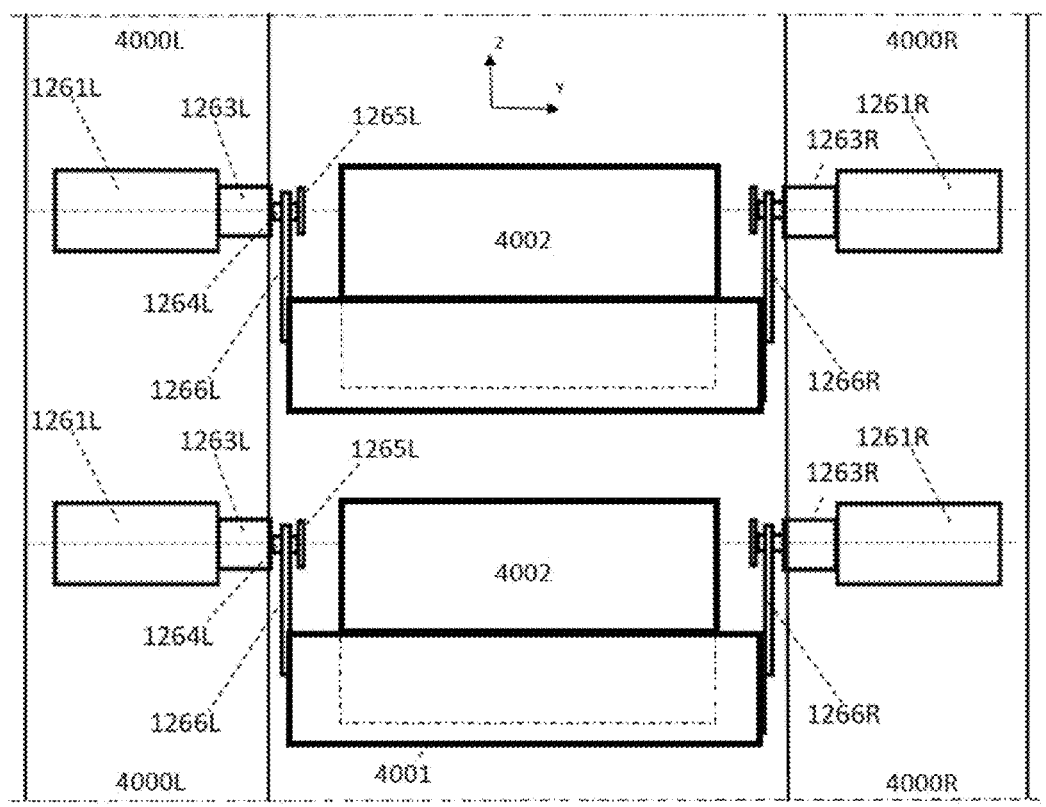

FIG. 26—illustrate Z-Y view of an AADVS carrier CONVEYOR (4000), which is configured with the following parameters: single closed loop transport TRACK; VERTI- CAL index; dual BELTS (4000L, 4000R) which can be configured with embedded or insertable BEARING assemblies (1261L. 1261R); each BEARING can be configured to support respective side of the item CARRIER (4001), which is described in details on FIGS. 11, 12; the CARRIER (4001) is loaded with a CONTAINER (4002) with prescription MEDICATIONS inside. When CONVEYOR (4000) is moving, the CARRIERS, supported from the BEARINGS of the BELTS of the CONVEYOR, will maintain essentially vertical alignment in respect to Z-axis, with insignificant swing angle around Y-axis, eliminating practically any vibrations experienced by the MEDICATIONS stored inside the CONTAINER (4002). Remaining elements are labeled same as on FIG. 11, 12, 23, 25.

Figure 27:
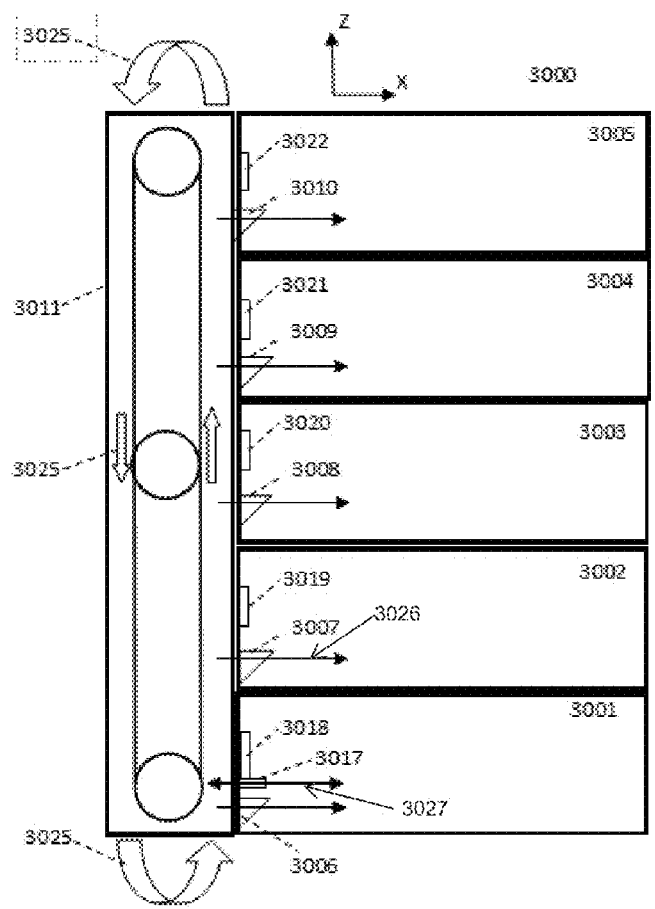

FIG. 27—illustrate Z-X view of AADVS (3000) with integrated AADVS QUALITY control ALGORITHM. The AADVS (3000) in this example is further configured for providing single side (right side of X-axis, as shown) services for a multi-floor building (5-floors in this example). The AADVS (3000) is configured with AADVS CONVEYOR (3011), such as the one shown on FIG. 25, for supporting FLOOR-GROUP distribution/dispensing of ITEMS, such as prescription MEDICATIONS, originated at the PHARMACY situated on the first floor (3001). The ITEMS are processed by the PHARMACY and then loaded by authorized personnel into CARRIERS, such as the one shown on FIG. 23, of the CONVEYOR (3011), and as indicated by arrow (3027) and then delivered by AADVS CONVEYOR (3011) to the service FLOORS (3002-3005), where the ITEMS are removed from the CARRIER by authorized personnel, as indicated by arrow (3026). The AADVS (3000) configurations include also configurations supporting distribution/dispensing of ITEMS, such as MISC. supplies, which can be loaded at designed FLOORS into the CARRIERS, such as the one shown on FIG. 23, of the AADVS CONVEYOR (3011) and distributed to other FLOORS, as needed. The configurations of access to AADVS (3000) by the PHARMACY at the 1-st FLOOR and authorized personnel at FLOORS 2 through 5 are illustrated on FIG. 28. The features of the AADVS (3000) include: continuous monitoring of QUALITY of MEDICATIONS, by continuous verification of specification parameters related to MEDICATIONS and PROCESS parameters related to sustaining QUALITY of MEDICATIONS. The AADVS QUALITY control ALGORITHM for AADVS (3000) can be configured as described in this application, including configurations based on respective applicable STEPS described on FIGS. 51 through 60. Elements are labeled as follows:

3006—Access window for loading/unloading of ITEMS into/from CONVEYOR (3011) of the AADVS (3000). The bi-directional arrow signifies the ability of the PHARMACY to load/unload the ITEMS.

3017—AADVS QUALITY verification devices providing support for the PHARMACY in performing QUALITY verification STEPS prior to loading the MEDICATION inside AADVS (3000), and devices performing incoming inspection by AADVS (3000) QUALITY control ALGORITHM prior to accepting the loaded MEDICATION into AADVS (3000). Only MEDICATIONS in full compliance are accepted by AADVS (3000), while the rejected MEDICATIONS are returned back to PROVIDER.

3018—AADVS (3000) control interface for PROVIDER of the PHARMACY.

3007, 3008, 3009, 3010—Access window for loading/unloading ITEMS into CONVEYOR of the AADVS (3000), respectively for service FLOORS (3002 through 3005). The respective arrows signify unloading of ITEMS.

3019, 3020, 3021, 3022—AADVS (3000) control interface respectively for FLOORS (3002 through 3005)

3011—AADVS CONVEYOR SYSTEM, which is configured to support AADVS services described above. AADVS CONVEYOR configurations include: single TRACK dual BELT configuration described on FIGS. 25 and 26.

3025—direction of advancing of the AADVS CONVEYOR (3011), shown counter-clockwise as example. The AADVS CONVEYOR (3011) can be configured for moving in both directions, counter-clockwise and clockwise.

Figure 28:
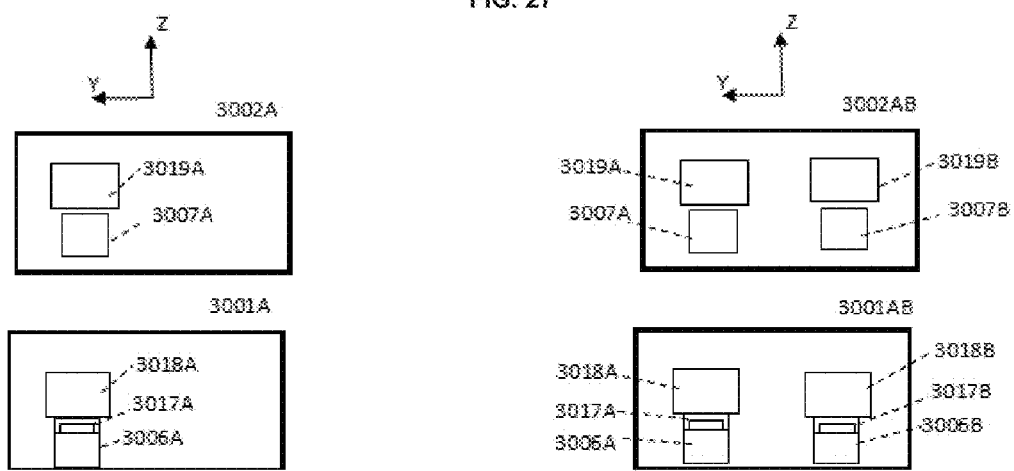

FIG. 28—illustrate Z-Y views of AADVS (3000) configurations of the PHARMACY located on FLOOR (3001), and configurations of the service FLOOR (3002), as an example.

3001A—Configuration AADVS (3000) supporting single CONVEYOR SYSTEM, PHARMACY FLOOR (3001).

3006A—Access window for loading/unloading ITEMS into/from the CONVEYOR of the AADVS (3000) by authorized personnel by the PHARMACY.

3017A—AADVS QUALITY verification devices providing support for the PHARMACY in performing QUALITY verification STEPS prior to loading the MEDICATION inside AADVS (3000), and devices performing incoming inspection by AADVS (3000) QUALITY control ALGORITHM prior to accepting the loaded MEDICATION into AADVS (3000). Only MEDICATIONS in full compliance are accepted by AADVS (3000), while the rejected MEDICATIONS are returned back to PROVIDER.

3018A—AADVS (3000) control interface for PROVIDER of the PHARMACY.

3002A—Configuration AADVS (3000) supporting single CONVEYOR SYSTEM, service FLOOR (3002).

3007A—Access window for loading/unloading ITEMS into/from CONVEYOR of the AADVS (3000) by authorized personnel on FLOOR (3002). As needed, AADVS QUALITY verification devices providing support for the authorized personnel on FLOOR (3002), not shown for simplicity, can be added and used by authorized personnel to perform QUALITY verification STEPS of unloaded MEDICATIONs from AADVS (3000).

3019A—AADVS (3000) control interface for authorized personnel FLOOR (3002).

3001AB—Configuration AADVS (3000) supporting dual independent AADVS CONVEYOR SYSTEMS service from the same side, labeled "A" (left side) and "B" (right side) for simplicity, PHARMACY FLOOR (3001).

3006A, 3006B—respectively CONVEYOR "A" and CONVEYOR "B" access window for loading/unloading ITEMS into/from the respective CONVEYORS of the AADVS (3000) by authorized personnel by the PHARMACY.

3017A, 3017B—respectively CONVEYOR "A" and CONVEYOR "B" AADVS QUALITY verification devices providing support for the PHARMACY in performing QUALITY verification STEPS prior to loading the MEDICATION inside AADVS (3000), and devices performing incoming inspection by AADVS (3000) QUALITY control ALGORITHM prior to accepting the loaded MEDICATION into AADVS (3000). Only MEDICATIONS in full compliance are accepted by AADVS (3000), while the rejected MEDICATIONS are returned back to PROVIDER.

3018A, 3018B—respectively CONVEYOR "A" and CONVEYOR "B" AADVS (3000) control interface for PROVIDER of the PHARMACY.

3002AB—Configuration AADVS (3000) supporting dual independent AADVS CONVEYOR SYSTEMS, service FLOOR (3002).

3007A, 3007B—respectively CONVEYOR "A" and CONVEYOR "B" access window for loading/unloading ITEMS into/from CONVEYOR of the AADVS (3000) by authorized personnel on FLOOR (3002). As needed, AADVS QUALITY verification devices providing support for the authorized personnel on FLOOR (3002), not shown for simplicity, can be added and used by authorized personnel to perform QUALITY verification STEPS of unloaded MEDICATIONs from AADVS (3000).

3019A, 3019B—respectively CONVEYOR "A" and CONVEYOR "B" AADVS (3000) control interface for authorized personnel FLOOR (3002).

Figure 29:
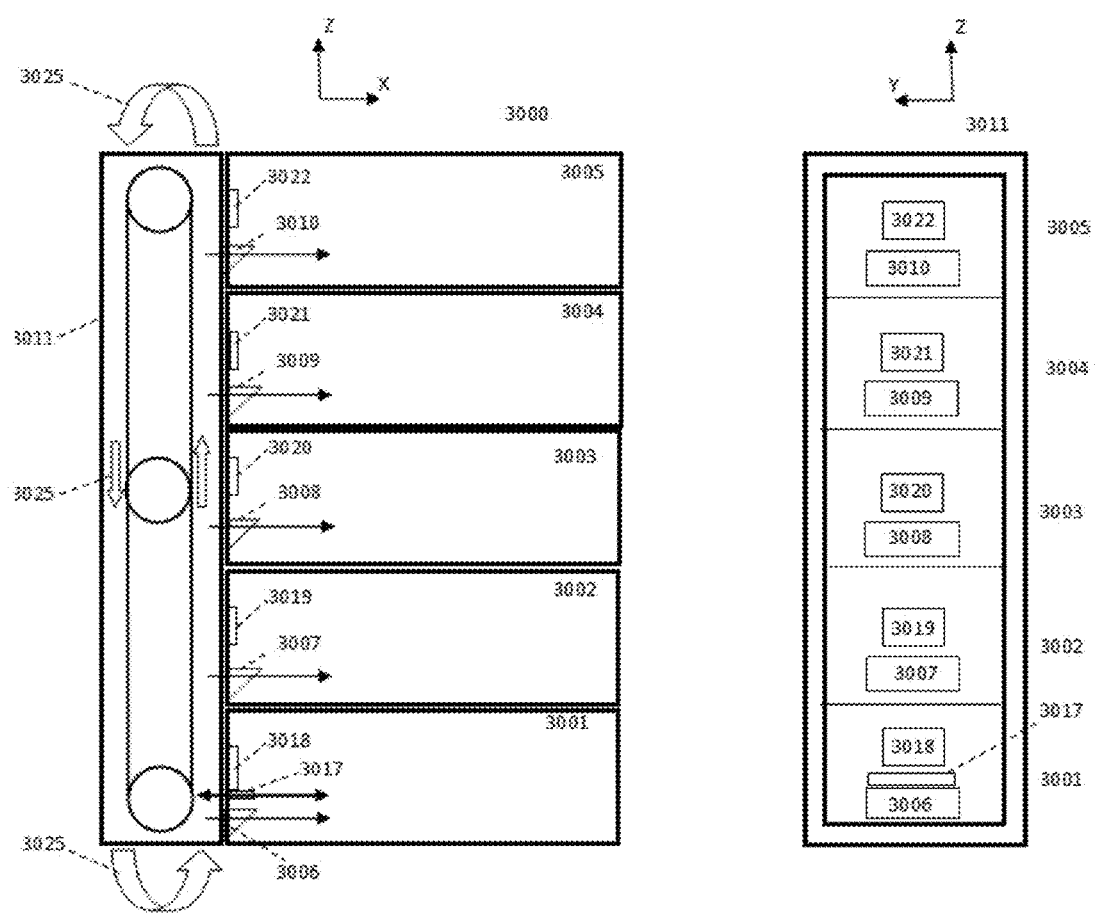

FIG. 29—illustrate views of AADVS (3000) described on FIG. 27, and which is configured with a single AADVS CONVEYOR. Elements are labeled same as on FIG. 27.

Figure 30:
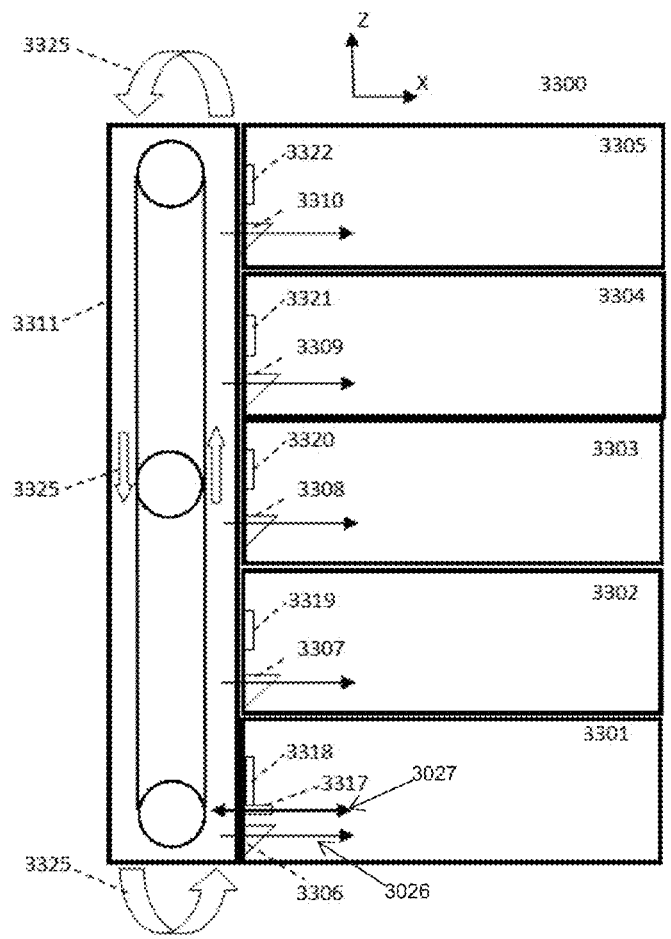

FIG. 30—illustrate Z-X view of AADVS (3300) with integrated AADVS QUALITY control ALGORITHM. The AADVS (3300) in this example is further configured for providing single side (right side of X-axis, as shown) services for a multi-floor building (5-floors in this example). The AADVS (3300) is configured with AADVS CONVEYOR (3311), such as the one shown on FIG. 26, for supporting distribution/dispensing of ITEMS, such as PATIENT specific prescription MEDICATIONS, originated at the PHARMACY situated on the first floor (3301). The ITEMS are processed by the PHARMACY and then loaded by authorized personnel into CARRIERS, such as the one shown on FIG. 12, of the CONVEYOR (3311) and then delivered by AADVS CONVEYOR (3311) directly to the PATIENTS room located on service FLOORS (3302-3305), where the ITEMS are removed from the CARRIER by authorized personnel. The configurations of access to AADVS (3300) by the PHARMACY at the 1-st FLOOR and authorized personnel at FLOORS 2 through 5 are illustrated on FIG. 31. The features of the AADVS (3300) include: continuous monitoring of QUALITY of MEDICATIONS, by continuous verification of specification parameters related to MEDICATIONS and PROCESS parameters related to sustaining QUALITY of MEDICATIONS. The AADVS QUALITY control ALGORITHM for AADVS (3300) can be configured as described in this application, including configurations based on respective applicable STEPS described on FIGS. 51 through 60. Elements are labeled as follows:

3306—Access window for loading/unloading of ITEMS into/from CONVEYOR (3311) of the AADVS (3300). The bi-directional arrow signifies the ability of the PHARMACY to load/unload the ITEMS.

3317—AADVS QUALITY verification devices providing support for the PHARMACY in performing QUALITY verification STEPS prior to loading the MEDICATION inside AADVS (3300), and devices performing incoming inspection by AADVS (3300) QUALITY control ALGORITHM prior to accepting the loaded MEDICATION into AADVS (3300). Only MEDICATIONS in full compliance are accepted by AADVS (3300), while the rejected MEDICATIONS are returned back to PROVIDER.

3318—AADVS (3300) control interface for PROVIDER of the PHARMACY.

3307, 3308, 3309, 3310—Access window for loading/unloading ITEMS into/from CARRIERS of the CONVEYOR (3311) of the AADVS (3300), respectively for service FLOORS (3302 through 3305). The respective arrows signify unloading of ITEMS.

3319, 3320, 3321, 3322—AADVS (3300) control interface respectively for FLOORS (3302 through 3305)

3311—AADVS CONVEYOR SYSTEM, which is configured to support AADVS services described above. AADVS CONVEYOR configurations include: single TRACK dual BELT configuration described on FIG. 26.

3325—direction of advancing of the AADVS CONVEYOR (3311), shown counter-clockwise as example. The AADVS CONVEYOR (3311) can be configured for moving in both directions, counter-clockwise and clockwise.

Figure 31:
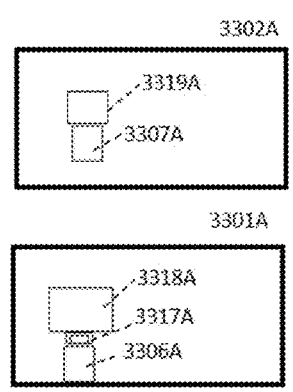

FIG. 31—illustrate Z-Y views of AADVS (3300) configurations of the PHARMACY located on FLOOR (3301), and configurations of the AADVS (3000) for the service FLOOR (3302), as an example.

3301A—Configuration AADVS (3300) supporting single CONVEYOR SYSTEM, PHARMACY FLOOR (3301).

3306A—Access window for loading/unloading ITEMS into/from the CONVEYOR of the AADVS (3300) by authorized personnel by the PHARMACY.

3317A—AADVS QUALITY verification devices providing support for the PHARMACY in performing QUALITY verification STEPS prior to loading the MEDICATION inside AADVS (3300), and devices performing incoming inspection by AADVS (3300) QUALITY control ALGORITHM prior to accepting the loaded MEDICATION into AADVS (3300). Only MEDICATIONS in full compliance are accepted by AADVS (3300), while the rejected MEDICATIONS are returned back to PROVIDER.

3318A—AADVS (3300) control interface for PROVIDER of the PHARMACY.

3302A—Configuration AADVS (3300) supporting single CONVEYOR SYSTEM, service FLOOR (3302).

3307A—Access window for loading/unloading ITEMS into/from CONVEYOR of the AADVS (3300) by authorized personnel on FLOOR (3302). As needed, AADVS QUALITY verification devices providing support for the authorized personnel on FLOOR (3302), not shown for simplicity, can be added and used by authorized personnel to perform QUALITY verification STEPS of unloaded MEDICATIONs from AADVS (3300).

3319A—AADVS (3300) control interface for authorized personnel FLOOR (3302).

3301AB—Configuration AADVS (3300) supporting dual independent AADVS CONVEYOR SYSTEMS, labeled "A" and "B" for simplicity, PHARMACY FLOOR (3301).

3306A, 3306B—respectively CONVEYOR "A" and CONVEYOR "B" access window for loading/unloading ITEMS into/from the respective CONVEYORS of the AADVS (3300) by authorized personnel by the PHARMACY.

3317A, 3317B—respectively CONVEYOR "A" and CONVEYOR "B" AADVS QUALITY verification devices providing support for the PHARMACY in performing QUALITY verification STEPS prior to loading the MEDICATION inside AADVS (3300), and devices performing incoming inspection by AADVS (3300) QUALITY control ALGORITHM prior to accepting the loaded MEDICATION into AADVS (3300). Only MEDICATIONS in full compliance are accepted by AADVS (3300), while the rejected MEDICATIONS are returned back to PROVIDER.

3318A, 3318B—respectively CONVEYOR "A" and CONVEYOR "B" AADVS (3300) control interface for PROVIDER of the PHARMACY.

3302AB—Configuration AADVS (3300) supporting dual independent AADVS CONVEYOR SYSTEMS, service FLOOR (3302).

3307A, 3307B—respectively CONVEYOR "A" and CONVEYOR "B" access window for loading/unloading ITEMS into/from CONVEYOR of the AADVS (3300) by authorized personnel on FLOOR (3302). As needed, AADVS QUALITY verification devices providing support for the authorized personnel on FLOOR (3302), not shown for simplicity, can be added and used by authorized personnel to perform QUALITY verification STEPS of unloaded MEDICATIONs from AADVS (3300).

3319A, 3319B—respectively CONVEYOR "A" and CONVEYOR "B" AADVS (3300) control interface for authorized personnel FLOOR (3302).

Figure 32:
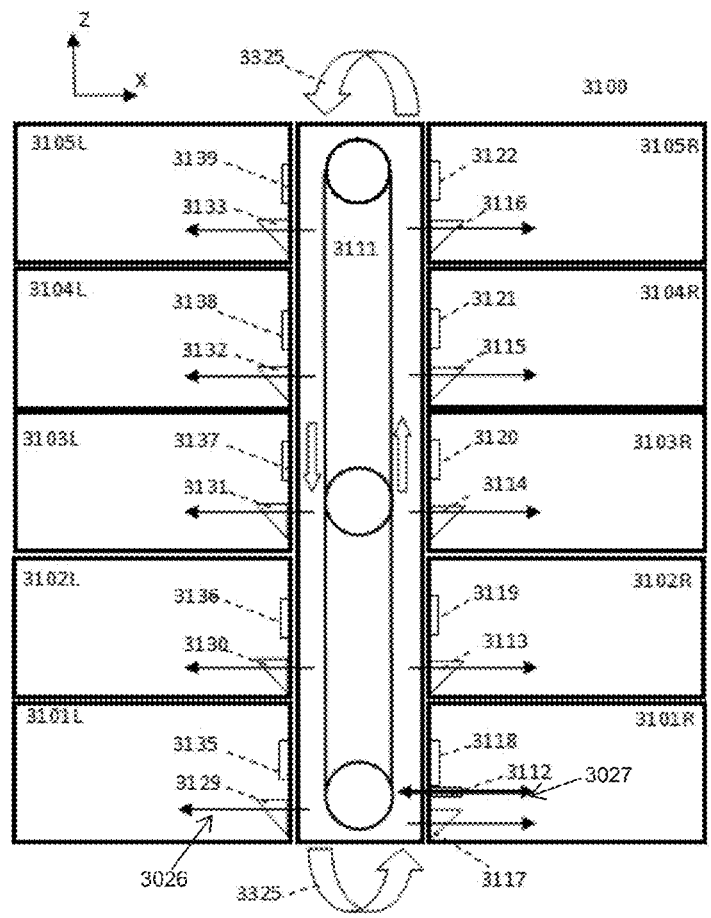

FIG. 32—illustrate Z-X view of AADVS (3100) with integrated AADVS QUALITY control ALGORITHM. The AADVS (3100) is configured for providing dual side services, left side elements labeled with suffix "L", and the right side elements are labeled with suffix "R". The AADVS (3100) is configured for serving a multi-floor building (5-floors in this example). The AADVS (3100) configured with a PHARMACY situated on the 1-st FLOOR section (3101R). The PHARMACY is configured to provide services from one side (3101R). The AADVS (3100) is configured with AADVS CONVEYOR SYSTEM (3111), which is configured for providing services from the PHARMACY located on the right section FLOOR (3101R) to the left section FLOOR (3101L), and for both left and right sections of the upper FLOORS (3102 through 3105). The AADVS CONVEYOR SYSTEM (3111) includes configurations consisting of a single AADVS CONVEYOR or combination of multiple independent AADVS CONVEYORS starting at the PHARMACY FLOOR (3101R). Each AADVS CONVEYOR can be configured with a single side services of a FLOOR as described on FIGS. 27-31, or configured with a dual side services of a FLOOR, as described in this example. Figure elements are labeled as follows:

3117—Access window for the PHARMACY situated on the right side of the FLOOR #1 (3101R), which is configured for loading/unloading of ITEMS into/from CONVEYOR (3111) of the AADVS (3100). The bi-directional arrow signifies the ability of the PHARMACY to load/unload the ITEMS.

3112—AADVS QUALITY verification devices providing support for the PHARMACY section (3101R) in performing QUALITY verification STEPS prior to loading the MEDICATION inside AADVS CONVEYOR (3111), and devices performing incoming inspection by AADVS CONVEYOR (3111) QUALITY control ALGORITHM prior to accepting the loaded MEDICATION into AADVS (3100). Only MEDICATIONS in full compliance are accepted by AADVS (3100), while the rejected MEDICATIONS are returned back to PROVIDER.

3118—AADVS (3100) control interface for PROVIDER of the PHARMACY section (3101R).

3113, 3114, 3115, 3116—Access window for loading/unloading ITEMS into/from CARRIERS of the CONVEYOR (3111) of the AADVS (3100) by authorized FLOOR service personnel, respectively for service FLOORS (3102R through 3105R). The respective arrows signify unloading of ITEMS.

3119, 3120, 3121, 3122—AADVS (3100) control interface respectively for FLOORS (3102R through 3105R).

3129, 3130, 3131, 3132, 3133—Access window for loading/unloading ITEMS into/from CARRIERS of the CONVEYOR (3111) of the AADVS (3100) by authorized FLOOR service personnel, respectively for service FLOORS (3101L through 3105L). The respective arrows signify unloading of ITEMS.

3135, 3136, 3137, 3138, 3139—AADVS (3100) control interface respectively for service FLOORS (3101L through 3105L).

3111—AADVS CONVEYOR SYSTEM, which is configured to support AADVS services described above. AADVS CONVEYOR configurations include: single TRACK dual BELT configuration described on FIG. 26.

3325—direction of advancing of the AADVS CONVEYOR (3111), shown counter-clockwise as example. The AADVS CONVEYOR (3111) can be configured for moving in both directions, counter-clockwise and/or clockwise.

Figure 33:
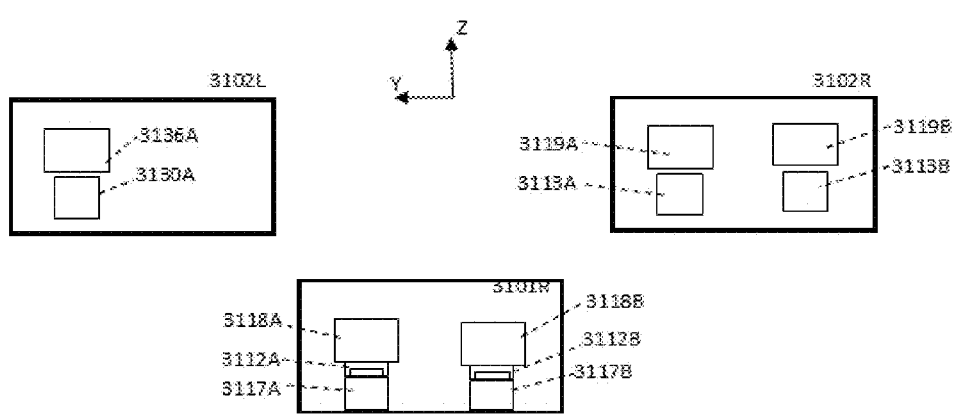

FIG. 33—illustrate Z-Y views of AADVS (3100) configurations of the PHARMACY located on FLOOR (3101R), and configurations of the AADVS (3100) for the service FLOOR (3102), as an example. Elements labeled:

3101R—Configuration AADVS (3100) supporting dual independent CONVEYOR SYSTEMS, labeled "A" and "B" for simplicity, PHARMACY FLOOR (3101R).

3117A, 3117B—respectively CONVEYOR "A" and CONVEYOR "B" access window for loading/unloading ITEMS into/from the respective CONVEYORS of the AADVS (3100) by authorized personnel by the PHARMACY.

3112A, 3112B—respectively CONVEYOR "A" and CONVEYOR "B" AADVS QUALITY verification devices providing support for the PHARMACY in performing QUALITY verification STEPS prior to loading the MEDICATION inside AADVS (3100), and devices performing incoming inspection by AADVS (3100) QUALITY control ALGORITHM prior to accepting the loaded MEDICATION into AADVS (3100). Only MEDICATIONS in full compliance are accepted by AADVS (3100), while the rejected MEDICATIONS are returned back to PROVIDER.

3102L—Configuration AADVS (3100) supporting single CONVEYOR SYSTEM, service FLOOR (3102L) as an example.

3130A—Access window for loading/unloading ITEMS into/from CONVEYOR of the AADVS (3100) by authorized personnel on FLOOR (3102L). As needed, AADVS QUALITY verification devices providing support for the authorized personnel on FLOOR (3102L), not shown for simplicity, can be added and used by authorized personnel to perform QUALITY verification STEPS of unloaded MEDICATIONs from AADVS (3100).

3136A—AADVS (3100) control interface for authorized personnel FLOOR (3102L).

3102R—Configuration AADVS (3100) supporting dual independent AADVS CONVEYOR SYSTEMS, labeled "A" and "B" for simplicity, service FLOOR (3102R), as an example.

3113A, 3113B—respectively CONVEYOR "A" and CONVEYOR "B" access window for loading/unloading ITEMS into/from the respective CONVEYORS of the AADVS (3100) by authorized personnel servicing the FLOOR (3102R).

3119A, 3119B—respectively CONVEYOR "A" and CONVEYOR "B" user interfaces for authorized personnel servicing the FLOOR (3102R).

Figure 34:
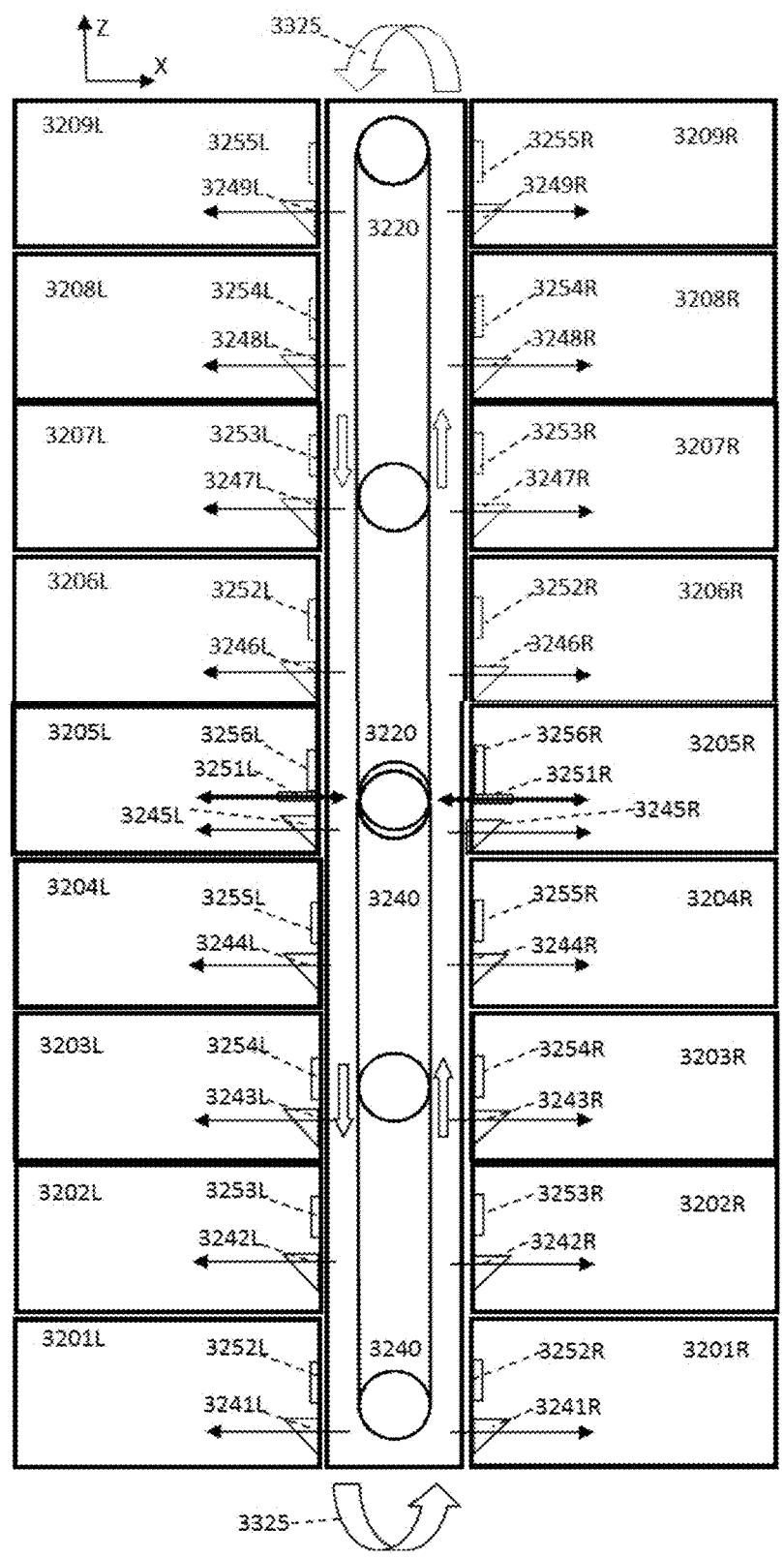

FIG. 34—illustrate Z-X view of AADVS (3200) with integrated AADVS QUALITY control ALGORITHM. The AADVS (3200) is configured for providing dual side services, left side elements labeled with suffix "L", and the right side elements are labeled with suffix "R". The AADVS (3200) is configured for serving a multi-floor building (9-floors in this example). The AADVS (3200) configured with a PHARMACY situated on the 5-th FLOOR. The PHARMACY is configured to provide services from both sides, the left side of the 5-th FLOOR (3205L) and the right side of the 5-th FLOOR (3205R). The AADVS (3200) is configured with two independent AADVS CONVEYOR SYSTEMS: the AADVS CONVEYOR SYSTEM (3220) is configured for serving from the PHARMACY FLOOR (3205) to the upper FLOORS (3206 through 3209), and the AADVS CONVEYOR SYSTEM (3240) is configured for serving from the PHARMACY FLOOR (3205) to the lower FLOORS (3204 through 3201). The AADVS CONVEYOR SYSTEM (3220) includes configurations consisting of a single AADVS CONVEYOR starting at the PHARMACY FLOOR (3205) and going up to service FLOORS (3206) through (3209), or combination of multiple independent AADVS CONVEYORS starting at the PHARMACY FLOOR (3205) and going up to service all or specific FLOORS within the range of (3206) through (3209). The AADVS CONVEYOR SYSTEM (3240) includes configurations consisting of a single AADVS CONVEYOR starting at the PHARMACY FLOOR (3205) and going down to service FLOORS (3204) through (3201), or combination of multiple independent AADVS CONVEYORS starting at the PHARMACY FLOOR (3205) and going down to service all or specific FLOORS within the range of (3204) through (3201). Each AADVS CONVEYOR can be configured with a single side services of a FLOOR as described on FIGS. 27-31, or configured with a dual side services of a FLOOR, as described on FIG. 32, 33, and shown on this FIG. 34, as an example. Elements are labeled as follows;

3245L—Access window for the section of the PHARMACY situated on the FLOOR (3205L), which is configured for loading/unloading of ITEMS into/from CONVEYOR (3220) of the AADVS (3200). The bi-directional arrow signifies the ability of the PHARMACY to load/unload the ITEMS.

3251L—AADVS QUALITY verification devices providing support for the PHARMACY section (3205L) in performing QUALITY verification STEPS prior to loading the MEDICATION inside AADVS CONVEYOR (3220), and devices performing incoming inspection by AADVS CONVEYOR (3220) QUALITY control ALGORITHM prior to accepting the loaded MEDICATION into AADVS (3200). Only MEDICATIONS in full compliance are accepted by AADVS (3200), while the rejected MEDICATIONS are returned back to PROVIDER.

3256L—AADVS (3200) control interface for PROVIDER of the PHARMACY section (3205L).

3246L, 3247L, 3248L, 3249L—Access window for loading/unloading ITEMS into/from CARRIERS of the CONVEYOR (3220) of the AADVS (3200) by authorized FLOOR service personnel, respectively for service FLOORS (3206L through 3209L). The respective arrows signify unloading of ITEMS.

3252L, 3253L, 3254L, 3255L—AADVS (3200) control interface respectively for service FLOORS (3206L through 3209L)

3246R, 3247R, 3248R, 3249R—Access window for loading/unloading ITEMS into/from CARRIERS of the CONVEYOR (3220) of the AADVS (3200) by authorized FLOOR service personnel, respectively for service FLOORS (3206R through 3209R). The respective arrows signify unloading of ITEMS.

3252R, 3253R, 3254R, 3255R—AADVS (3200) control interface respectively for service FLOORS (3206R through 3209R)

3220—AADVS CONVEYOR SYSTEM, which is configured to support AADVS services described above. AADVS CONVEYOR configurations include: single TRACK dual BELT configuration described on FIG. 26.

3325—direction of advancing of the AADVS CONVEYOR (3220), shown counter-clockwise as example. The AADVS CONVEYOR (3220) can be configured for moving in both directions, counter-clockwise and/or clockwise.

3245R—Access window for the section of the PHARMACY situated on the FLOOR (3205R), which is configured for loading/unloading of ITEMS into/from CONVEYOR (3240) of the AADVS (3200). The bi-directional arrow signifies the ability of the PHARMACY to load/unload the ITEMS.

3251R—AADVS QUALITY verification devices providing support for the PHARMACY section (3205R) in performing QUALITY verification STEPS prior to loading the MEDICATION inside AADVS CONVEYOR (3240), and devices performing incoming inspection by AADVS CONVEYOR (3240) QUALITY control ALGORITHM prior to accepting the loaded MEDICATION into AADVS (3200). Only MEDICATIONS in full compliance are accepted by AADVS (3200), while the rejected MEDICATIONS are returned back to PROVIDER.

3256R—AADVS (3200) control interface for PROVIDER of the PHARMACY section (3205R).

3244R, 3243R, 3242R, 3241R—Access window for loading/unloading ITEMS into/from CARRIERS of the CONVEYOR (3240) of the AADVS (3200) by authorized FLOOR service personnel, respectively for service FLOORS (3204R through 3201R). The respective arrows signify unloading of ITEMS.

3255R, 3254R, 3253R, 3252R—AADVS (3200) control interface respectively for service FLOORS (3204R through 3201R)

3244L, 3243L, 3242L, 3241L—Access window for loading/unloading ITEMS into/from CARRIERS of the CONVEYOR (3240) of the AADVS (3200) by authorized FLOOR service personnel, respectively for service FLOORS (3204L through 3201L). The respective arrows signify unloading of ITEMS.

3255L, 3254L, 3253L, 3252L—AADVS (3200) control interface respectively for service FLOORS (3204L through 3201L)

3240—AADVS CONVEYOR SYSTEM, which is configured to support AADVS services described above. AADVS CONVEYOR configurations include: single TRACK dual BELT configuration described on FIG. 26.

3325—direction of advancing of the AADVS CONVEYOR (3240), shown counter-clockwise as example. The AADVS CONVEYOR (3240) can be configured for moving in both directions, counter-clockwise and/or clockwise.

Figure 35:
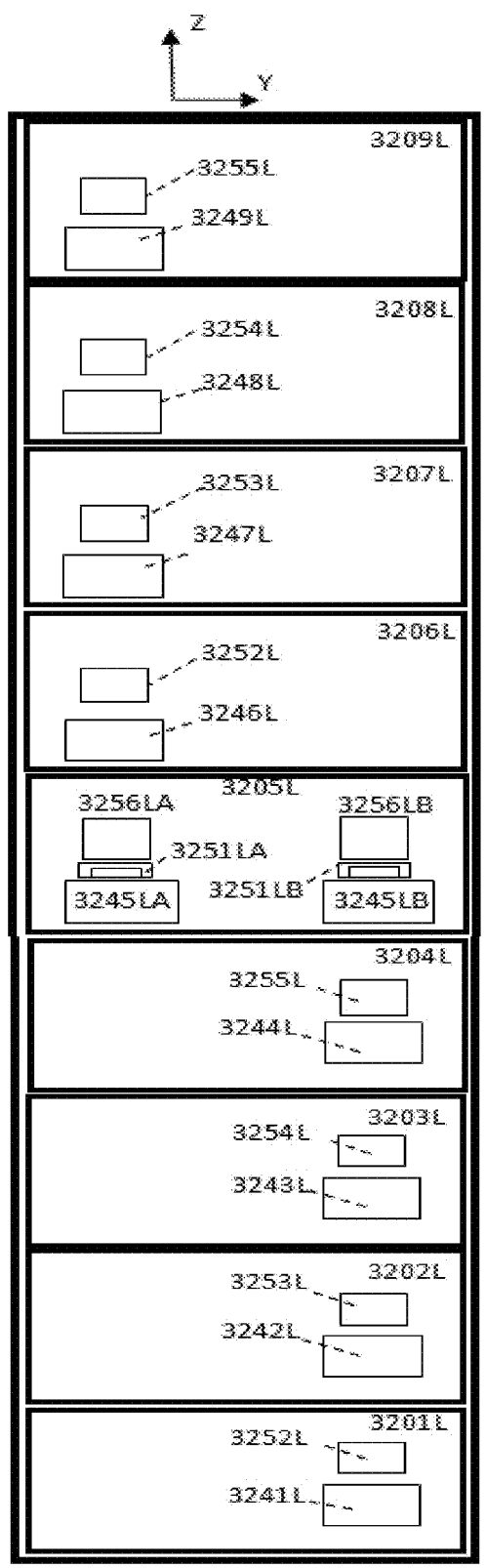

FIG. 35—illustrate Z-Y view of AADVS (3200) with integrated AADVS QUALITY control ALGORITHM, shown on FIG. 34 (left side), which is further configured to support the PHARMACY FLOOR (3205L) providing dual access, one (elements labeled with SUFFIX "A")—for servicing the AADVS CONVEYOR (3220), and the other access ((elements labeled with SUFFIX "B")—for servicing the AADVS CONVEYOR (3240). Remaining elements are labeled same as on FIG. 34.

Figure 36:
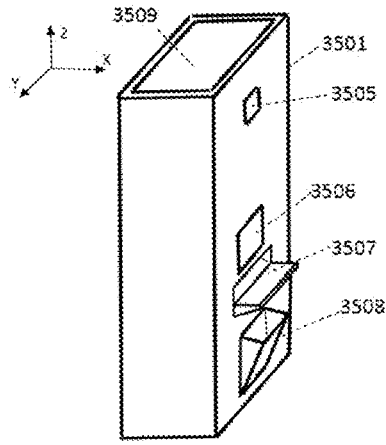

FIG. 36—illustrates 3-D view of AADVS section (3501) configured with a single AADVS vertical conveyor system, and is further configured for supporting operations at a PHARMACY floor. The configuration can be used for AADVS-Ps or AADVS-Gs for multi-floor configurations, and includes configurations described for FIGS. 27 through 35. Depending on selected layout, the AADVS section (3501) can be configured to support PROVIDER functions, including loading of MEDICATIONS into the carriers of the AADVS conveyor from one side (as shown, facing the X-axis), or both sides, including the opposite side, which is not shown for simplicity. For simplicity, the AADVS conveyor inside (3501) is not shown. The elements are labeled as follows:

3505—AADVS status indicator for PROVIDER, including configuration with LED.

3506—AADVS control panel for PROVIDER

3507—AADVS loading station for PROVIDER, which includes configurations with automatic quality verifications of the MEDICATION weight, size, barcode label

3508—AADVS pick-up bin for PROVIDER, from which AADVS dispensed requested or rejected MEDICATIONS are removed. Presence of MEDICATIONS in the pick-up bins is verified by respective AADVS QUALITY control SENSORS, including SENSORS configured for measuring weight of the pick-up bin, and reading the ID labels of MEDICATIONS being dispensed by AADVS.

3509—AADVS section upper floor interface for a multi-floor configuration, extending AADVS SYSTEM services to upper floors. As needed, a respective lower floor interface (not shown for simplicity) can be added, extending AADVS SYSTEM services to lower floors. AADVS SYSTEM for a multi-floor configuration can be assembled in sections, one floor at a time. The assembly process steps can be configured for optimum integration of the AADVS SYSTEM into a new or existing multi-floor building, including hospitals.

Figure 37:
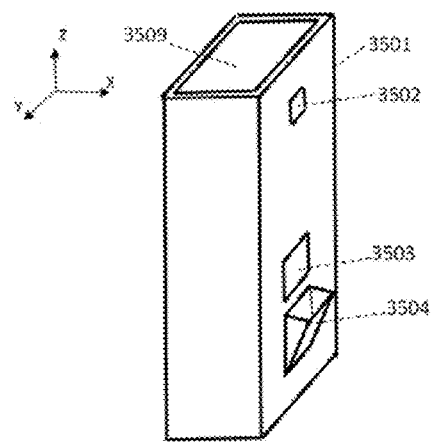

FIG. 37—illustrates 3-D view of AADVS section (3501) configured with a single AADVS vertical conveyor system, and is further configured for supporting operations at a service FLOOR. The configuration can be used for AADVS-Ps or AADVS-Gs for multi-floor configurations, and includes service FLOOR configurations described for FIGS. 27 through 35. Depending on selected layout, the AADVS section (3501) can be configured to support PROVIDER and/or authorized CUSTOMER functions, including unloading of MEDICATIONS from the carriers of the AADVS conveyor from one side (as shown, facing the X-axis), or both sides, including the opposite side, which is not shown for simplicity. For simplicity, the AADVS conveyor inside (3501) is not shown. As needed, the AADVS configuration can be further configured for supporting authorized personnel on each or selected floors to load into the empty slots inside the CARRIERS with empty CONTAINERS or rejected CONTAINERS, with appropriate labeling, to be returned back to the PHARMACY.

The elements are labeled as follows:

3502—AADVS status indicator for PROVIDER and/or authorized CUSTOMER.

3503—AADVS control panel for PROVIDER and/or authorized CUSTOMER

3504—AADVS pick-up bin for PROVIDER and/or authorized CUSTOMER. Presence of MEDICATIONS in the pick-up bins is verified by respective AADVS QUALITY control SENSORS, including SENSORS configured for measuring weight of the pick-up bin, and reading the ID labels of MEDICATIONS being dispensed by AADVS.

3509—AADVS section upper floor interface for a multi-floor configuration, as described for FIG. 36

Figure 38:
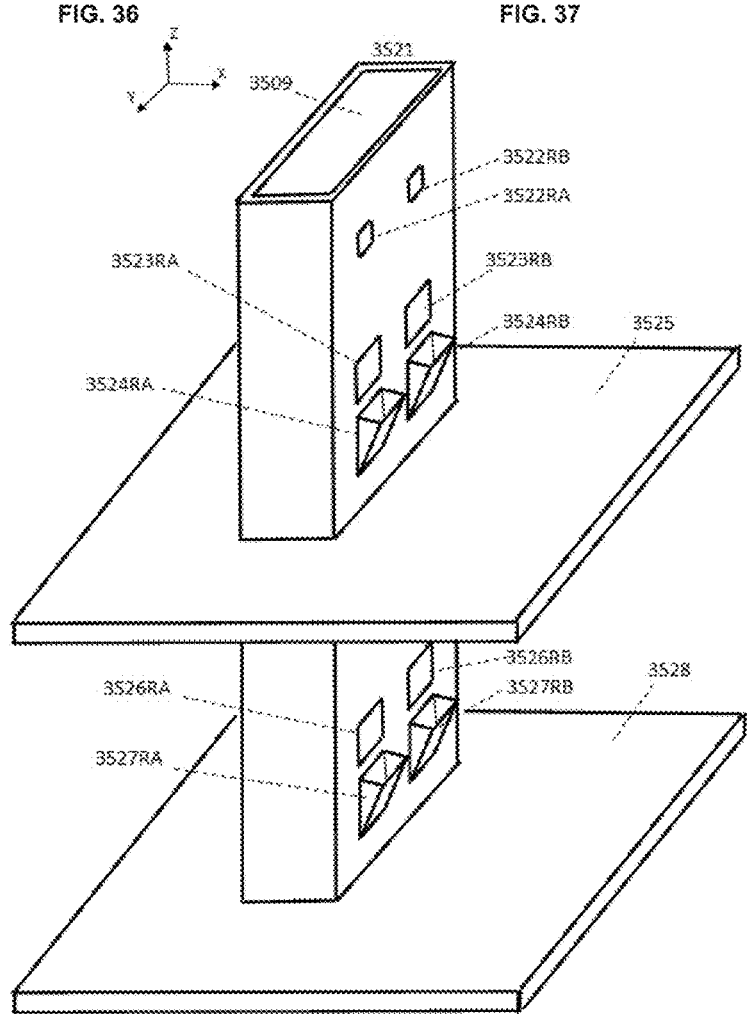

FIG. 38—illustrates 3-D view of AADVS section (3521) configured with a dual side-by-side AADVS vertical conveyor system, and is further configured for supporting operations at two service floors, upper floor (3525) and lower floor (3528). The configuration can be used for AADVS-Ps or AADVS-Gs multi-floor configurations. The AADVS section (3521) can be configured to support CUSTOMER functions from one side (as shown, facing the X-axis), or both sides, including the opposite side, which is not shown for simplicity, but described below. For simplicity, the following convention is used for labeling the respective AADVS components on this and other FIGS:

AADVS components, AADVS SYSTEM right side (X-axis)—label incorporating letter "R"

AADVS components. AADVS SYSTEM left side (X-axis)—label incorporating letter "L"

AADVS components, right side facing PROVIDER or CUSTOMER (Y-axis)—label incorporating letter "B"

AADVS components, left side facing PROVIDER or CUSTOMER (Y-axis)—label incorporating letter "A"

The elements for upper floor (3525) are labeled as follows:

3522RA(B)—status indicator, respectively for AADVS conveyor left(right) of the AADVS SYSTEM right side

3523RA(B)—CUSTOMER control panel, respectively for AADVS conveyor left(right) of AADVS SYSTEM right side

3524RA(B)—MEDICATION pick-up bin for CUSTOMER, from which dispensed requested MEDICATIONS are removed, respectively for AADVS conveyor left(right) of the AADVS SYSTEM right side

3509—AADVS section, as described for FIG. 36

The elements for lower floor (3528) are labeled as follows:

3526RA(B)—CUSTOMER control panel, respectively for AADVS conveyor left(right) of AADVS SYSTEM right side

3527RA(B)—MEDICATION pick-up bin for CUSTOMER, from which dispensed requested MEDICATIONS are removed, respectively for AADVS conveyor left(right) of the AADVS SYSTEM right side. Presence of MEDICATIONS in the pick-up bins is verified by respective AADVS QUALITY control SENSORS, including SENSORS configured for measuring weight of the pick-up bin, and reading the ID labels of MEDICATIONS being dispensed by AADVS.

Figure 39:
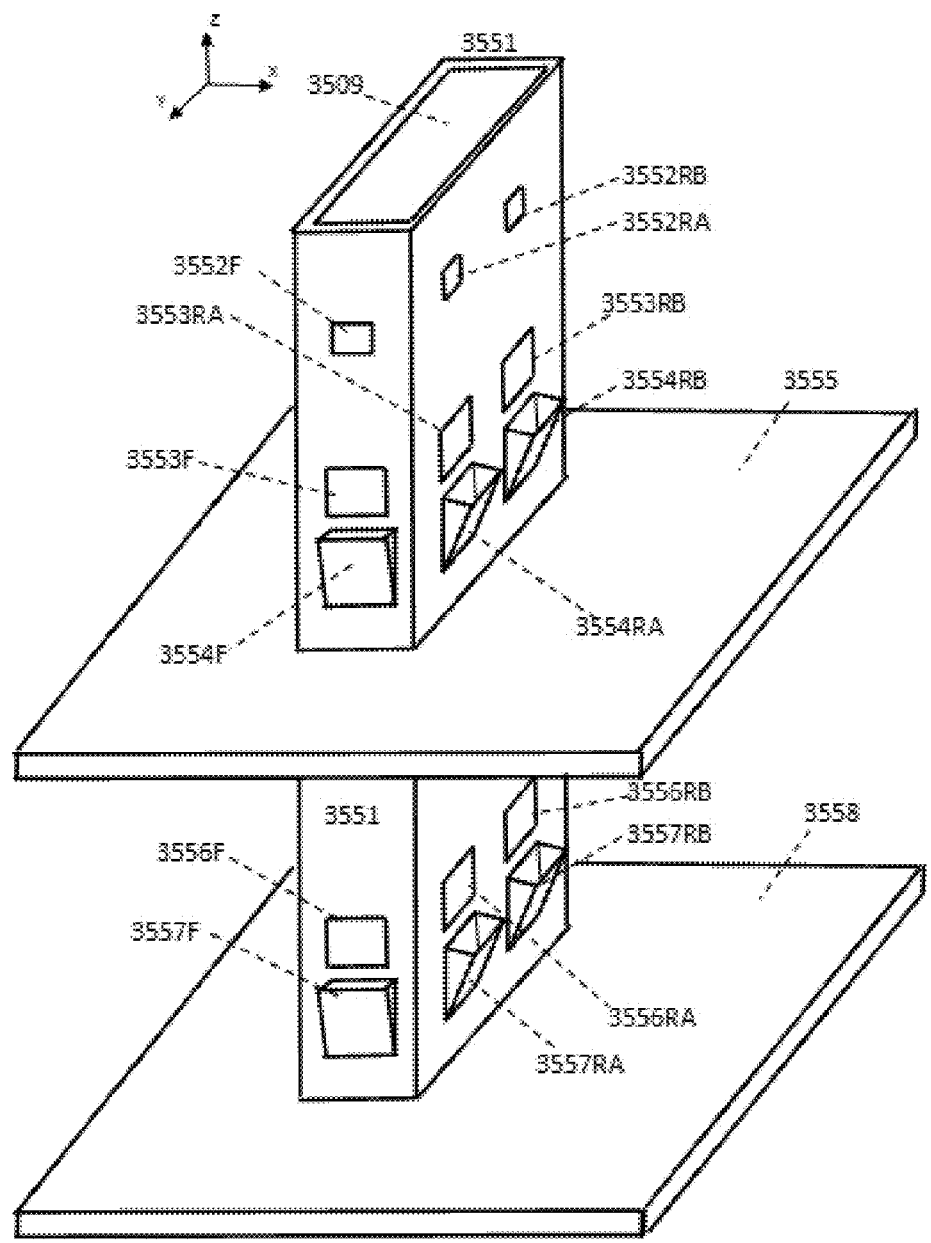

FIG. 39—illustrates 3-D view of AADVS section (3551) configured with providing respective services from each side: single service for each side (front and back) along the "Y-axis", and dual services for each side (left and right) along "X-axis". Each service can be configured with AADVS CONVEYOR SYSTEM independent of others, or configured with a shared AADVS CONVEYOR SYSTEM providing services to other sides.

Not all components are shown for simplicity. In the example, the AADVS vertical conveyor system is configured for supporting operations at two service floors, upper floor (3555) and lower floor (3558). The configuration can be used for AADVS-Ps or AADVS-Gs multi-floor configurations. For simplicity, the following convention is used for labeling the respective AADVS components on this and other FIGS:

AADVS components. AADVS SYSTEM right side (X-axis)—label incorporating letter "R"

AADVS components, AADVS SYSTEM left side (X-axis)—label incorporating letter "L"

AADVS components, AADVS SYSTEM front side (Y-axis)—label incorporating letter "F"

AADVS components, AADVS SYSTEM backside (Y-axis)—label incorporating letter "B"

AADVS components, right side facing PROVIDER or CUSTOMER (Y-axis)—label incorporating letter "B"

AADVS components, left side facing PROVIDER or CUSTOMER (Y-axis)—label incorporating letter "A"

The elements for upper floor (3555) are labeled as follows:

3552F, 3552RA, 3552RB—status indicator, respectively for AADVS conveyor front side, right side "A" and right side "B"

3553F, 3553RA, 3553RB—CUSTOMER control panel, respectively for AADVS conveyor front side, right side "A" and right side "B"

3554F, 3554RA, 3554RB—MEDICATION pick-up bin for CUSTOMER, from which dispensed requested MEDICATIONS are removed, respectively for AADVS conveyor front side, right side "A" and right side "B"

3509—AADVS section, as described for FIG. 36

The elements for lower floor (3558) are labeled as follows:

3556F, 3556RA, 3556RB—CUSTOMER control panel, respectively for AADVS conveyor front side, right side "A" and right side "B"

3557F, 3557RA, 3557RB—MEDICATION pick-up bin for CUSTOMER, from which dispensed requested MEDICATIONS are removed, respectively for AADVS conveyor front side, right side "A" and right side "B"

Figure 40:
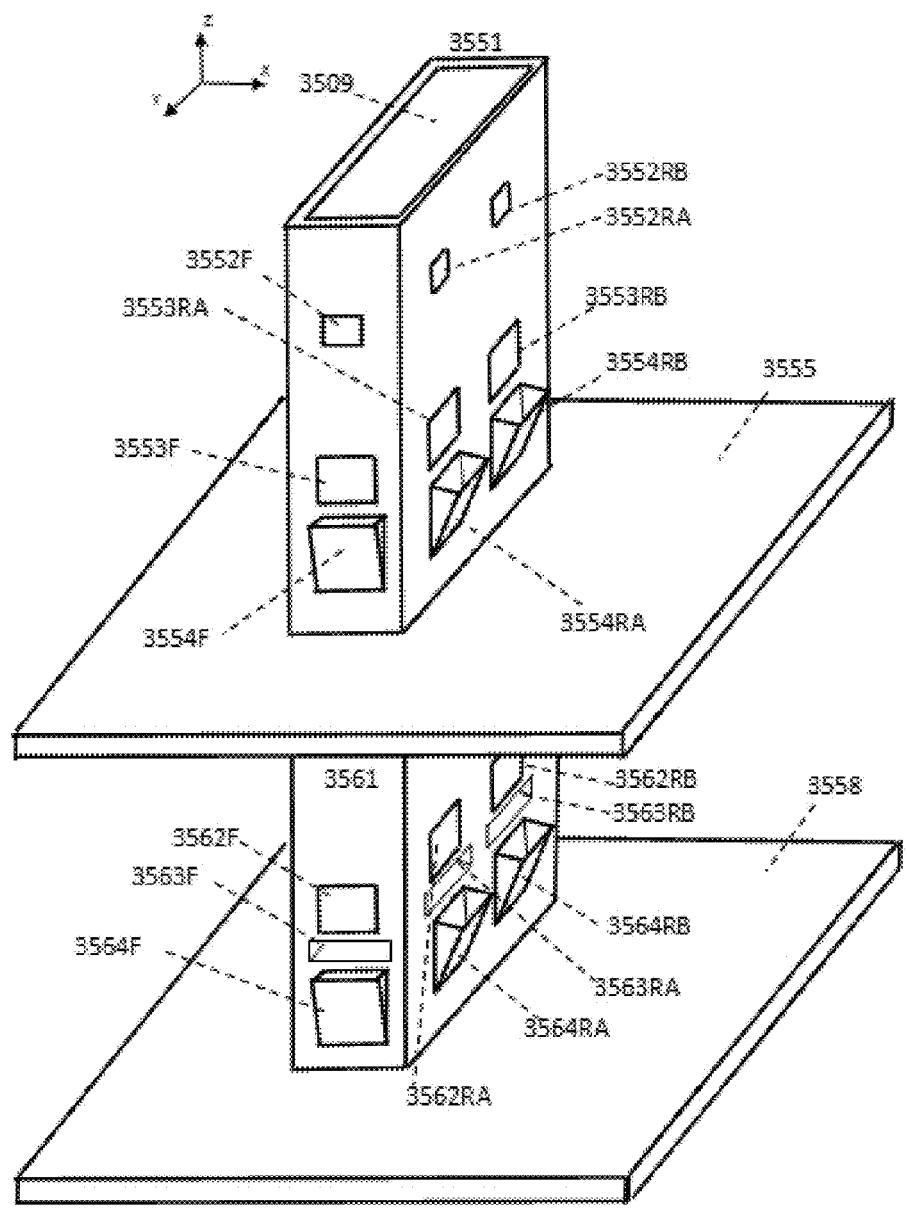

FIG. 40—illustrates 3-D view of AADVS section (3551), same as described on FIG. 39, and AADVS section (3561) configured for providing support of a PHARMACY located on FLOOR (3558), and serving independent AADVS CONVEYOR SYSTEMS servicing AADVS sections: front side, right side "A" and right side "B".

Elements for the PHARMACY FLOOR (3558) are labeled as follows:

3562F, 3562RA, 3562RB—PHARMACY control panel, respectively for AADVS conveyor front side, right side "A" and right side "B"

3563F, 3563RA, 3563RB—Access windows for the sections of the PHARMACY situated on the FLOOR (3558), which is configured for loading/unloading of ITEMS into/from CONVEYOR of the AADVS (3561) respectively for AADVS conveyor front side, right side "A" and right side "B". Access windows can be configured with AADVS QUALITY verification devices providing support for the PHARMACY in performing QUALITY verification STEPS prior to loading the MEDICATION inside AADVS CONVEYORS, and devices performing incoming inspection by QUALITY control ALGORITHM prior to accepting the loaded MEDICATION into AADVS (3561). Only MEDICATIONS in full compliance are accepted by AADVS (3561), while the rejected MEDICATIONS are returned back to PROVIDER via respective pick-up bins listed below.

3564F, 3564RA, 3564RB—MEDICATION pick-up bin for PHARMACY, serving respective AADVS sides: front, left side "A" and left side "B". The AADVS will automatically dispensed MEDICATIONS into respective pick-up bin, which are either requested by the PHARMACY and/or rejected by AADVS QUALITY control. Presence of MEDICATIONS in the pick-up bins is verified by respective AADVS QUALITY control SENSORS, including SENSORS configured for measuring weight of the pick-up bin, and reading the ID labels of MEDICATIONS being dispensed by AADVS.

Figure 41:
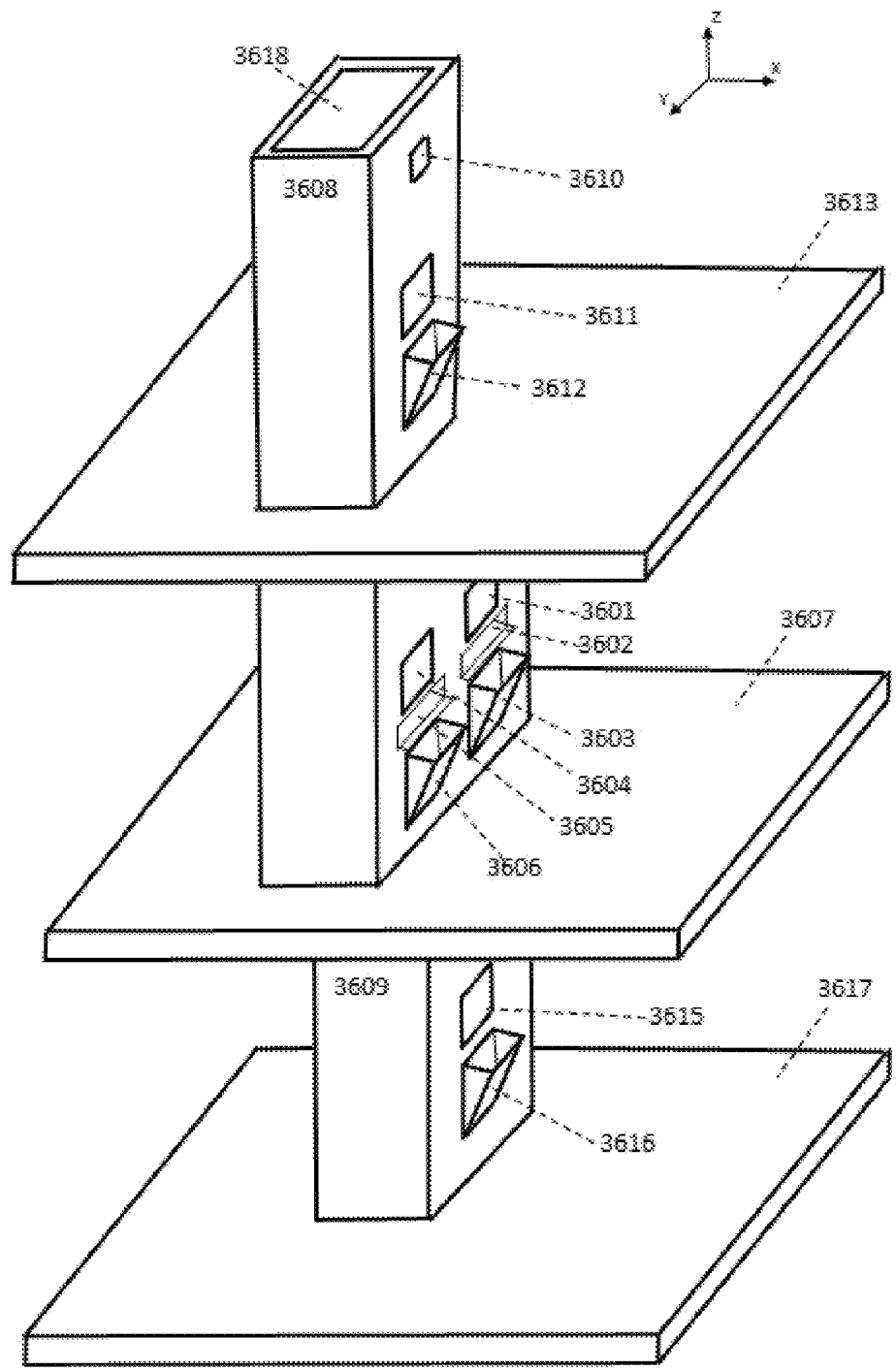

FIG. 41—illustrates 3-D view of AADVS configured for supporting PHARMACY services at the FLOOR (3607), and is further configured for providing services using AADVS CONVEYOR SYSTEM (3608) from the PHARMACY to the upper FLOOR (3613), and using AADVS CONVEYOR SYSTEM (3609) from the PHARMACY to the lower FLOOR (3617). AADVS CONVEYOR SYSTEMS (3608, 3609) for simplicity are configured and shown of providing services from one side—right in respect to X-axis. For reference, each or both AADVS CONVEYOR SYSTEMS can be configured as described for FIGS. 27 through 40. Figure elements are labeled as follows:

3601, 3604—PHARMACY control panel, respectively for AADVS conveyor (3609) and AADVS conveyor (3608)

3602, 3605—Access windows for the sections of the PHARMACY situated on the FLOOR (3607), which is configured for loading/unloading of ITEMS into/from respectively AADVS conveyor (3609) and AADVS conveyor (3608). Access windows can be configured with AADVS QUALITY verification devices providing support for the PHARMACY in performing QUALITY verification STEPS prior to loading the MEDICATION inside AADVS CONVEYORS, and devices performing incoming inspection by QUALITY control ALGORITHM prior to accepting the loaded MEDICATION into AADVS. Only MEDICATIONS in full compliance are accepted by AADVS, while the rejected MEDICATIONS are returned back to PROVIDER via respective pick-up bins listed below.

3603, 3606—MEDICATION pick-up bin for PHARMACY, serving respective AADVS conveyor (3609) and AADVS conveyor (3608). The AADVS will automatically dispensed MEDICATIONS into respective pick-up bin, which are either requested by the PHARMACY and/or rejected by AADVS QUALITY control. Presence of MEDICATIONS in the pick-up bins is verified by respective AADVS QUALITY control SENSORS, including SENSORS configured for measuring weight of the pick-up bin, and reading the ID labels of MEDICATIONS being dispensed by AADVS.

3610—STATUS indicator, AADVS conveyor (3608)

3611—Authorized personnel user interface. AADVS conveyor (3608)

3612—Authorized personnel MEDICATION pick-up bin. AADVS conveyor (3608)

3615—Authorized personnel user interface. AADVS conveyor (3609)

3616—Authorized personnel MEDICATION pick-up bin. AADVS conveyor (3609)

3618—AADVS section upper floor interface, as described for (3509)

Figure 42:
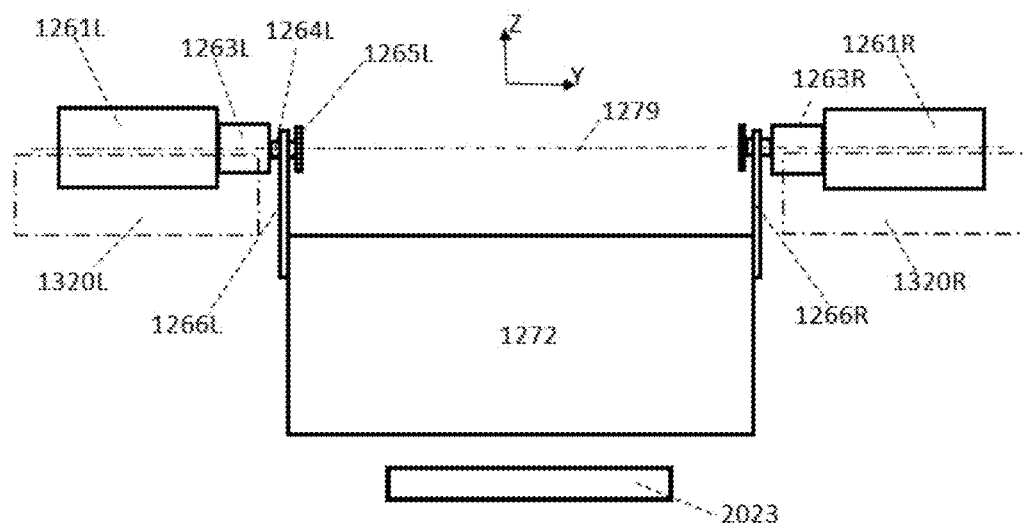

FIG. 42—illustrates Z-Y view of a section of AADVS CONVEYOR (1320), which is configured for QUALITY control ALGORITHM to measure weight of CARRIERS (1272) using AADVS SCALE system (2023). The locations and configurations of the SCALES (2023) within AADVS CONVEYOR SYSTEM are selected to ensure convenient and reliable weight measurements, aimed at supporting AADVS QUALITY control ALGORITHM. Example of the locations include: at the point of incoming QUALITY verification of loading of an ITEM into an empty CARRIER; in-process QUALITY verifications at the upper highest point for a AADVS vertical CONVEYOR; final QUALITY verification at the point just prior to dispensing the MEDICATION. As shown, the SCALE (2023) is retracted from the CARRIER (1272), allowing the CARRIER to pass the SCALES along the X-axis. Remaining elements are labeled same as on FIGS. 11, 12.

Figure 43:
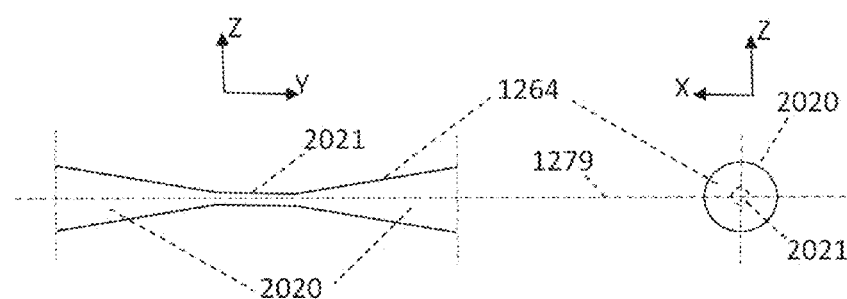

FIG. 43—illustrates Z-Y and Z-X detailed views of the shaft (1264) shown on FIGS. 11, 12, 42. The shaft configurations include configuration shown on FIG. 43, which includes a conical section (2020) on each end, and a round cylindrical section (2021) in the middle. The AADVS CONVEYOR SYSTEM is configured to provide support of each CARRIER from both left and right sides in respect to Y-axis, and is further configured to maintain the respective left and right support brackets (1266) of the CARRIERS within the round cylindrical section (2021) of the respective left and right shafts (1264). The configurations of all parts, including (2021), are aimed to: support reliable transportation of all CARRIERS by the AADVS conveyors with practically no disturbance of the ITEM, such as CONTAINER with MEDICATIONS inside, stored inside the CARRIERS; and support reliable weight measurement of the CARRIER (empty and/or loaded) using SCALE (2023), as shown on FIG. 45, with more details shown on FIG. 44. Remaining elements are labeled same as on FIGS. 11, 12.

Figure 44:
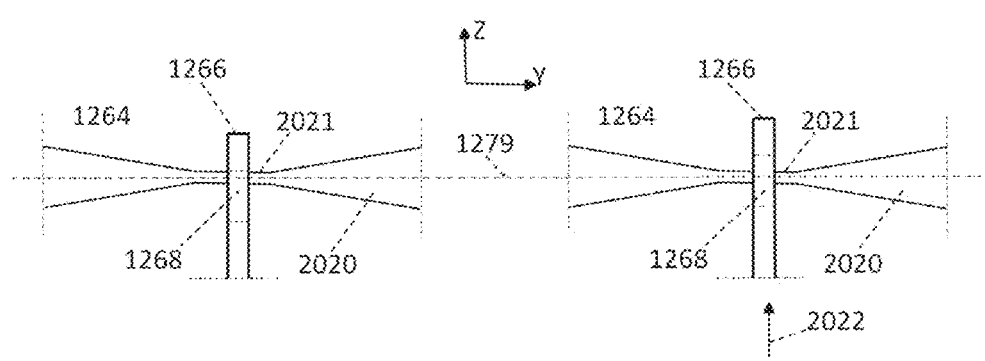

FIG. 44—illustrates Z-Y detailed view of the positions of CARRIER support bracket (1266) in respect to the support shaft (1264). The left view—illustrates the CARRIER support bracket (1266) in its lowered or engaged position in respect to the support shaft (1264), with the bracket (1266) being sustained in its position by the shaft (1264). When the CARRIER support bracket (1266) is engaged with the shaft (1264), the AADVS CONVEYOR with embedded or Insertable bearings will be able to advance the CARRIER along the CONVEYOR path. The right view—illustrates the CARRIER support bracket (1266) slightly elevated up along the Z-axis by the force (2022), and as result being disengaged from the support shaft (1264). The force (2022) is applied by the SCALES (2023), as shown on FIG. 45. During the weight measurements of a CARRIER with or without loaded with ITEM, the respective AADVS CONVEYOR is stopped from advancing. For reference, the AADVS SCALE system described on FIGS. 3-5, 13-15 can be configured to measure the weight of the respective entire section of the AADVS, with AADVS section consisting of: AADVS CONVEYOR with CARRIERS; AADVS Portable Vending Cartridge; AADVS Automatic Vending Module; or any other AADVS section, as needed. The AADVS configurations include configuration allowing weight measurements of the selected sections of AADVS while the CONVEYOR is either moving or not. The remaining elements are labeled same as on FIG. 12

Figure 45:
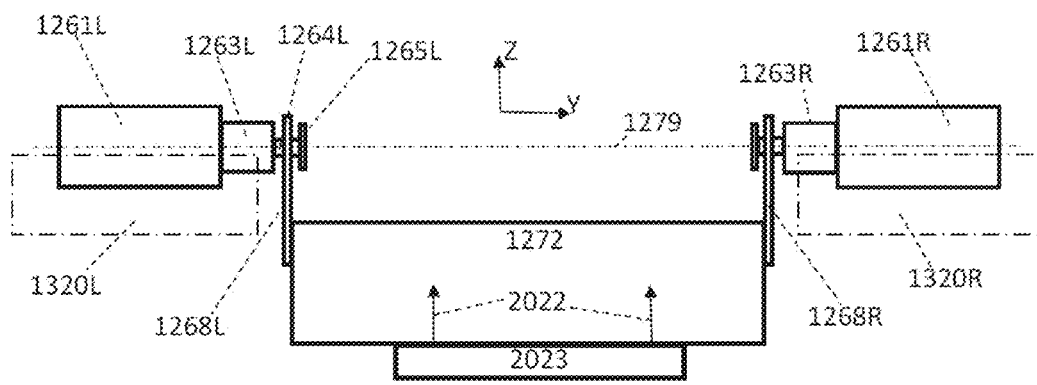

FIG. 45—illustrates Z-Y view of AADVS QUALITY control ALGORITHM using AADVS components and measuring the weight of the empty AADVS CARRIER (1272) by the AADVS SCALE (2023). The configurations of the CARRIER (1272) and the SCALE (2023) include configurations supporting reliable weight measurements of the CARRIER being empty and/or loaded. The configurations include mechanical configurations supporting reliable extension of the SCALE (2023) up along the Z-axis, and engaging with the CARRIER (1272), and by applying the forces (2022), elevating the CARRIER (1272) slightly up along the Z-axis, with details illustrated on FIG. 44, and as result, disengaging the CARRIER (1272) from the CARRIER support components of the AADVS conveyor (1320), allowing the SCALE (2023) to measure the weight of the CARRIER (1272) within AADVS specifications, including specifications in respect to accuracy of measuring weight of the CARRIER (1272) by the SCALE (2023). The AADVS conveyor (1320) is configured as a single track, dual BELT (1320L)—left side, (1320R)—right side, conveyor system, with respectively embedded and/or insertable BEARINGS, (1261L) for the left BELT (1320L) and BEARINGS (1261R) for the right BELT (1320R), with the BEARINGS providing support for the CARRIER (1272). The remaining elements are labeled same as on FIGS. 11, 12.

Figure 46:
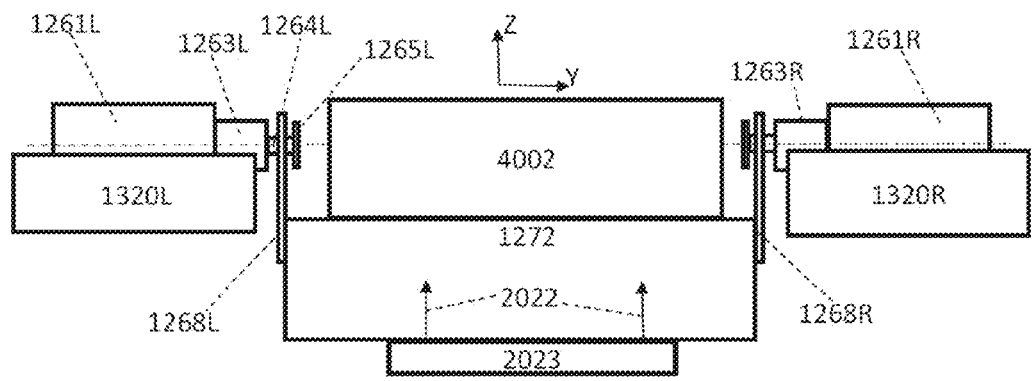

FIG. 46—illustrates Z-Y view of AADVS QUALITY control ALGORITHM using AADVS components and measuring the weight of the AADVS CARRIER (1272) loaded with ITEM (4002) by the AADVS SCALE (2023). Remaining elements are labeled same as on FIG. 44.

Figure 47:
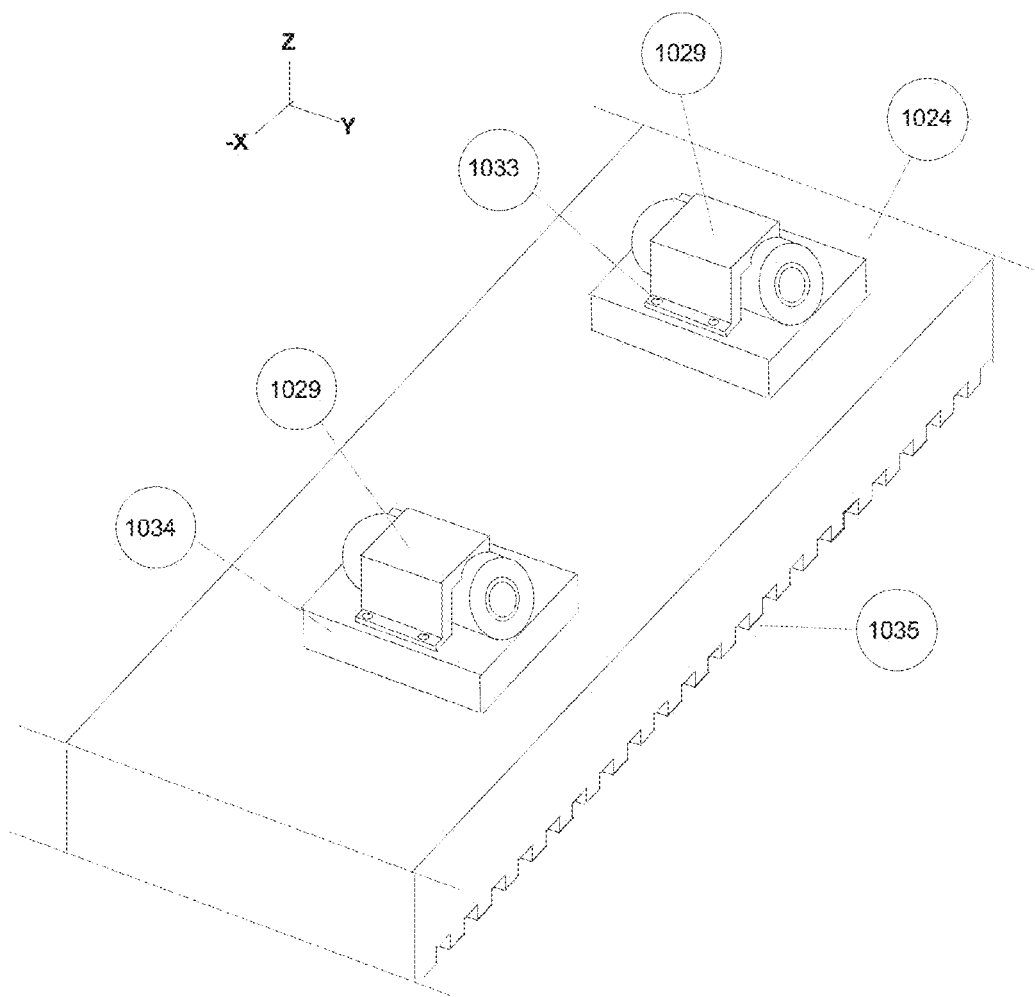

FIG. 47—illustrates 3D view of a section of AADVS BELT (1024) configuration with embedded or insertable BEARINGS (1029), which is copied from FIG. 3 of the document DRAWINGS and described in details in the document SPECIFICATIONS, both documents listed in the U.S. Pat. No. 8,954,190 "Optimization of Pharmacy Operations using Automatic Distributed Vending System".

Figure 48:
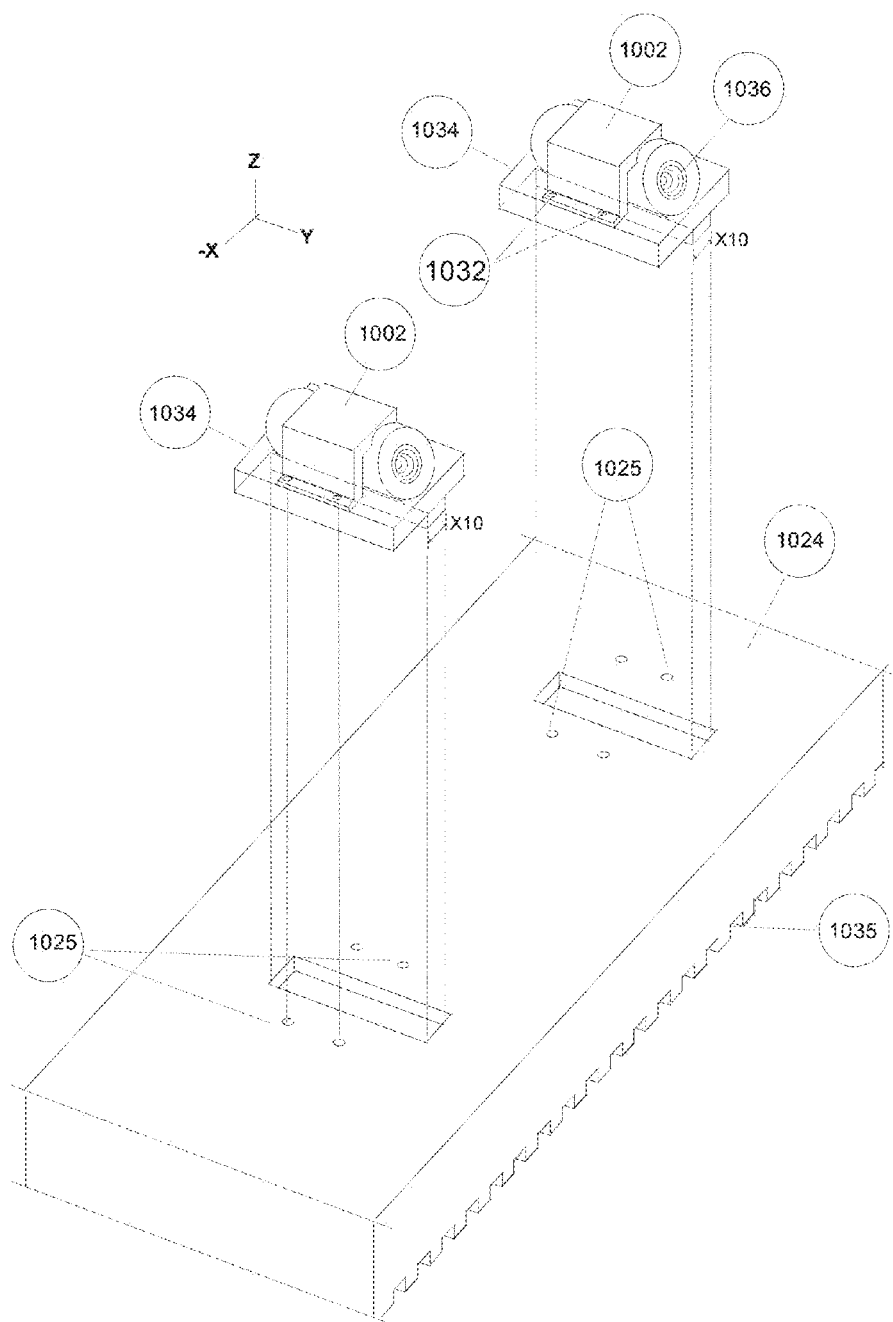

FIG. 48—illustrates 3D view of a construction method of the section of the AADVS BELT (1024) shown on FIG. 47, using insertable type BEARINGS (1002) which is copied from FIG. 5 of the document DRAWINGS and described in details in the document SPECIFICATIONS, both documents listed in the U.S. Pat. No. 8,954,190 "Optimization of Pharmacy Operations using Automatic Distributed Vending System".

Figure 49:
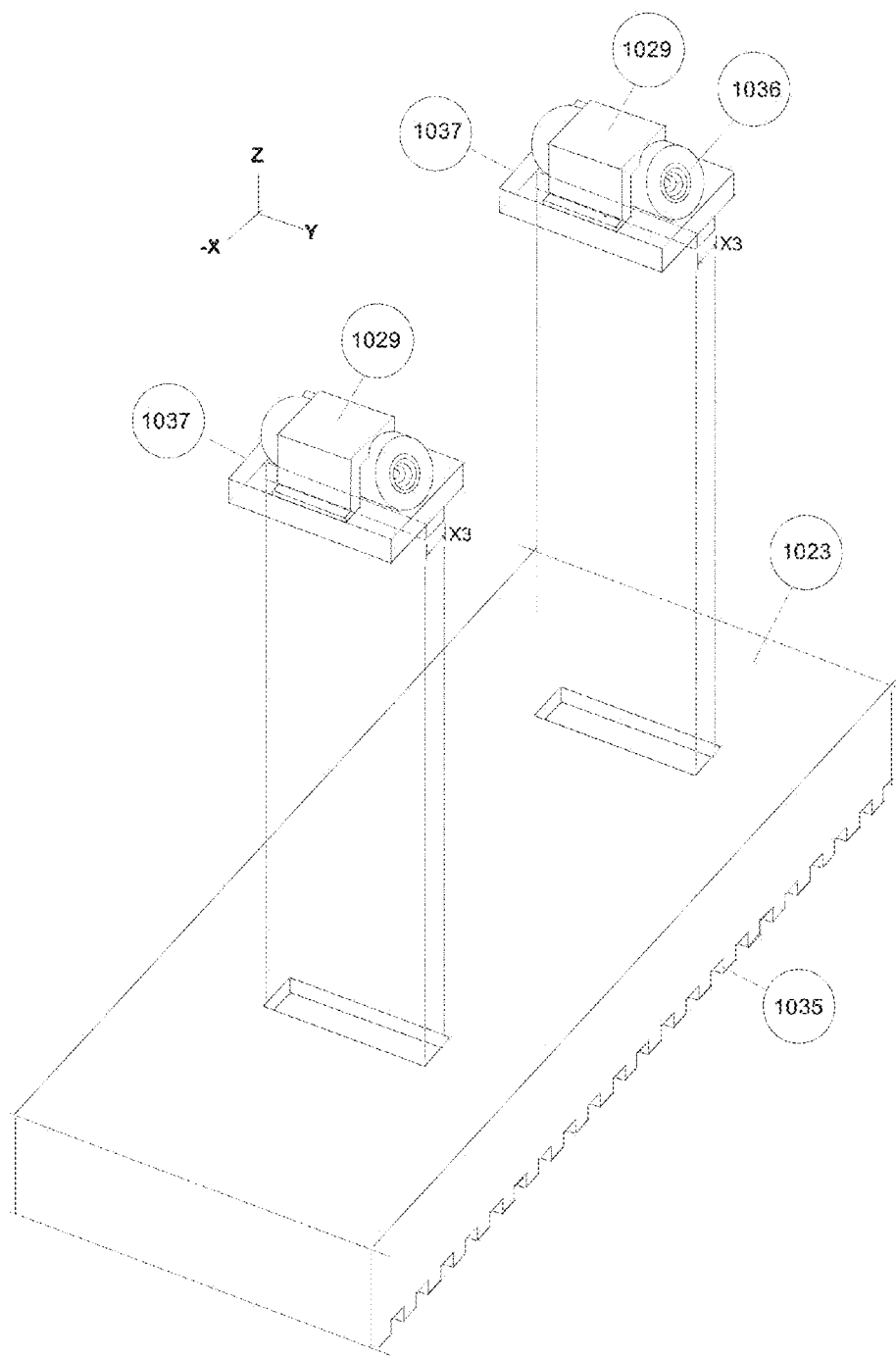

FIG. 49—illustrates 3D view of a construction method of the section of the AADVS BELT (1023), using embedded type BEARINGS (1029) which is copied from FIG. 6 of the document DRAWINGS and described in details in the document SPECIFICATIONS, both documents listed in the U.S. Pat. No. 8,954,190 "Optimization of Pharmacy Operations using Automatic Distributed Vending System".

Figure 50:
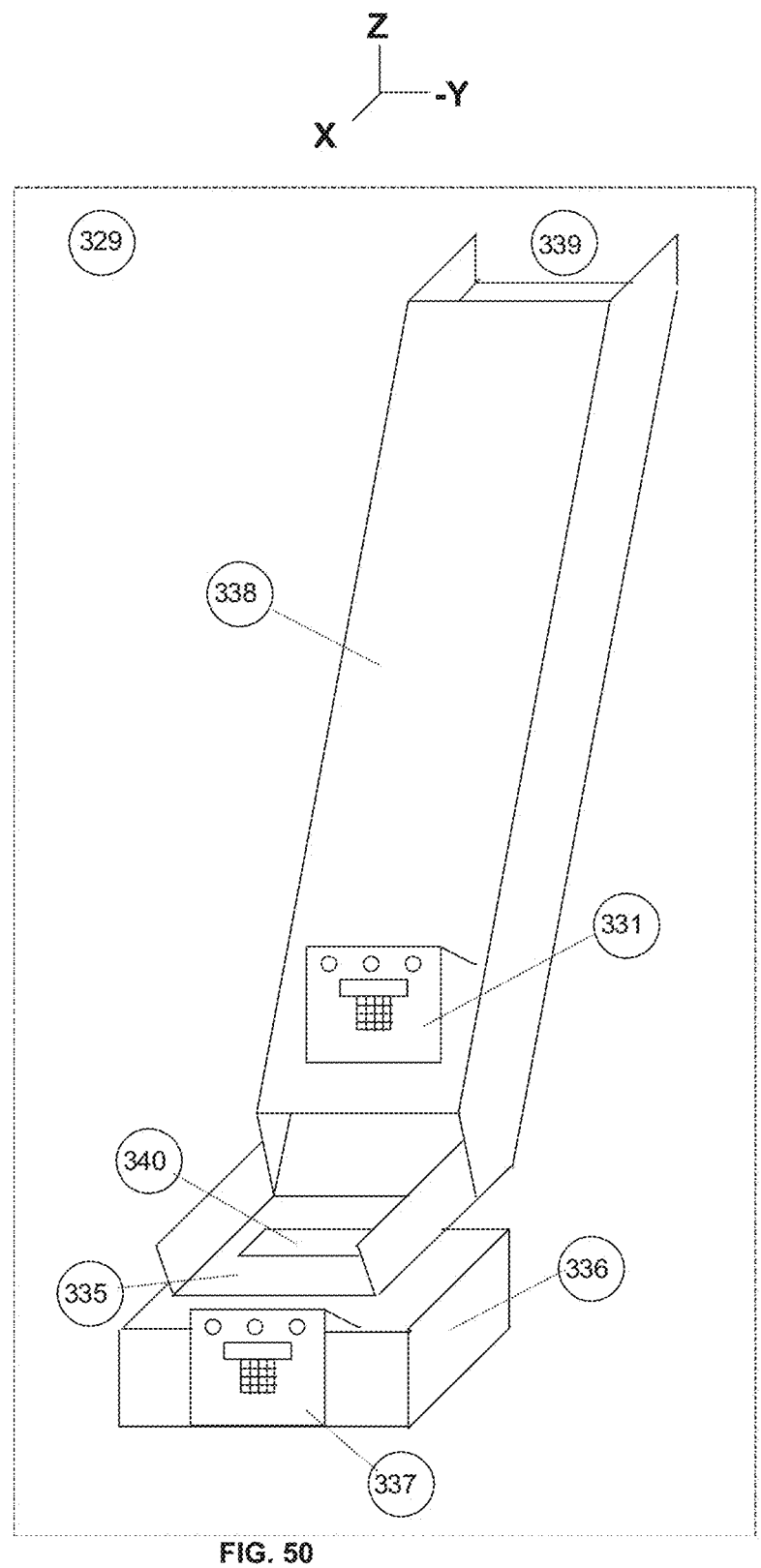

FIG. 50—illustrates 3D view of AADVS Item Feeding Conveyor (338), including AADVS devices (331, 335, 336, 337, 340) supporting AADVS QUALITY control ALGORITHM in performing quality verification steps, including operations in measuring weight and size of the ITEMS prior to acceptance into AADVS (338). The FIG. 50 is copied from FIG. 115 of the document DRAWINGS and described in details in the document SPECIFICATIONS, both documents listed in the U.S. Pat. No. 8,954,190 "Optimization of Pharmacy Operations using Automatic Distributed Vending System".

FIG. 51 through FIG. 60—illustrate a configuration of the AADVS QUALITY control ALGORITHM process STEPS for processing prescription MEDICATIONS by a business, including a pharmacy. The process STEPS are illustrated in flow-chart format. At all process STEPS, the PROVIDER will need to follow the respective business procedures and the AADVS QUALITY controls, and as needed, select the process STEPS in order to achieve QUALITY and operations CRITERIA, including: providing only QUALITY MEDICATIONS to authorized CUSTOMERS, and providing QUALITY services to CUSTOMERS while sustaining operating objectives in terms of business efficiency. The AADVS configurations described, include:

1) AADVS configuration for onsite processing of PRESCRIPTIONS and dispensing of MEDICATIONS
2) AADVS configuration for centralized processing of PRESCRIPTIONS, followed by distribution and dispensing at a remote location. This configuration also supports onsite dispensing of MEDICATIONS.

Figure 51:
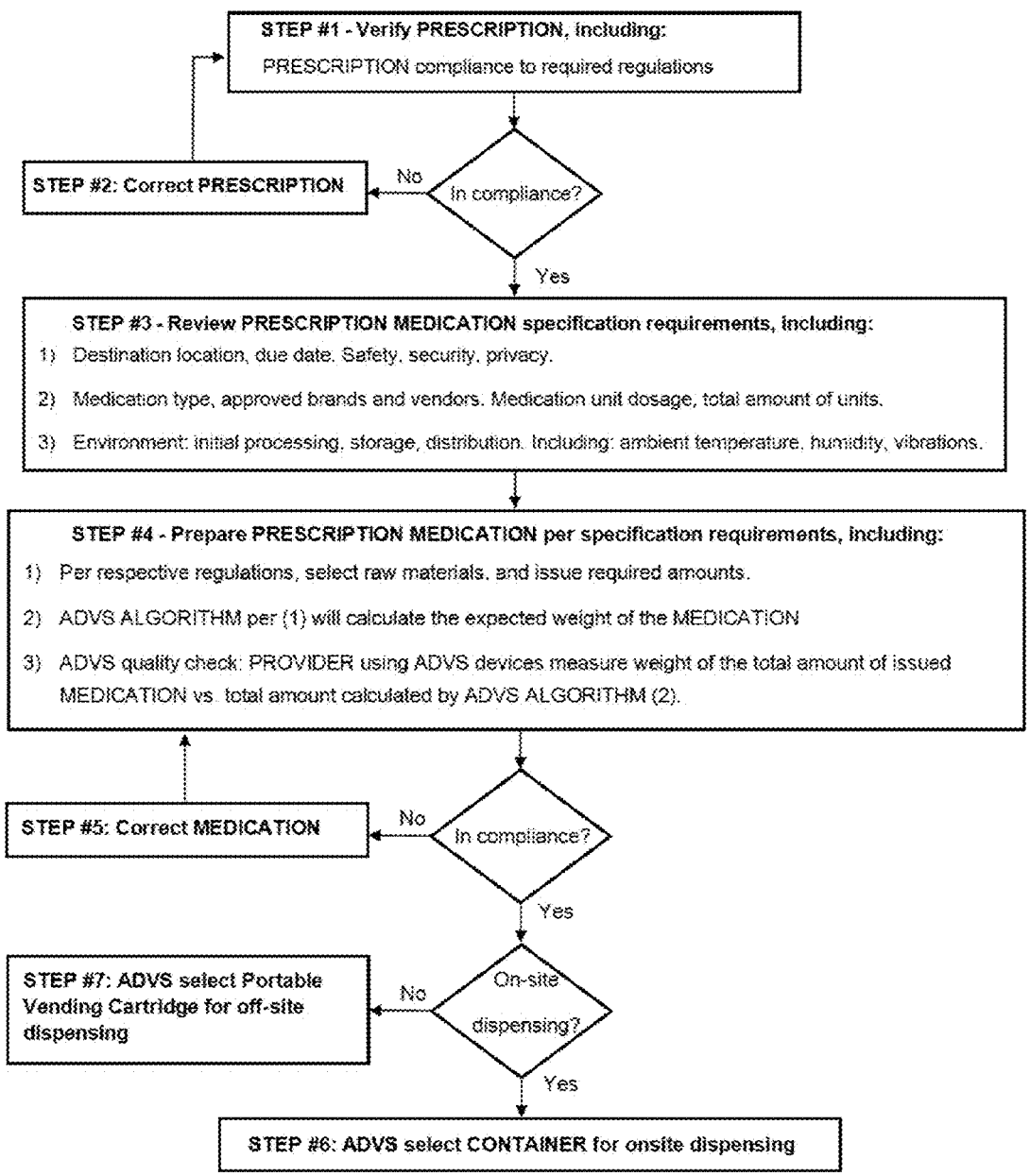
Figure 54:
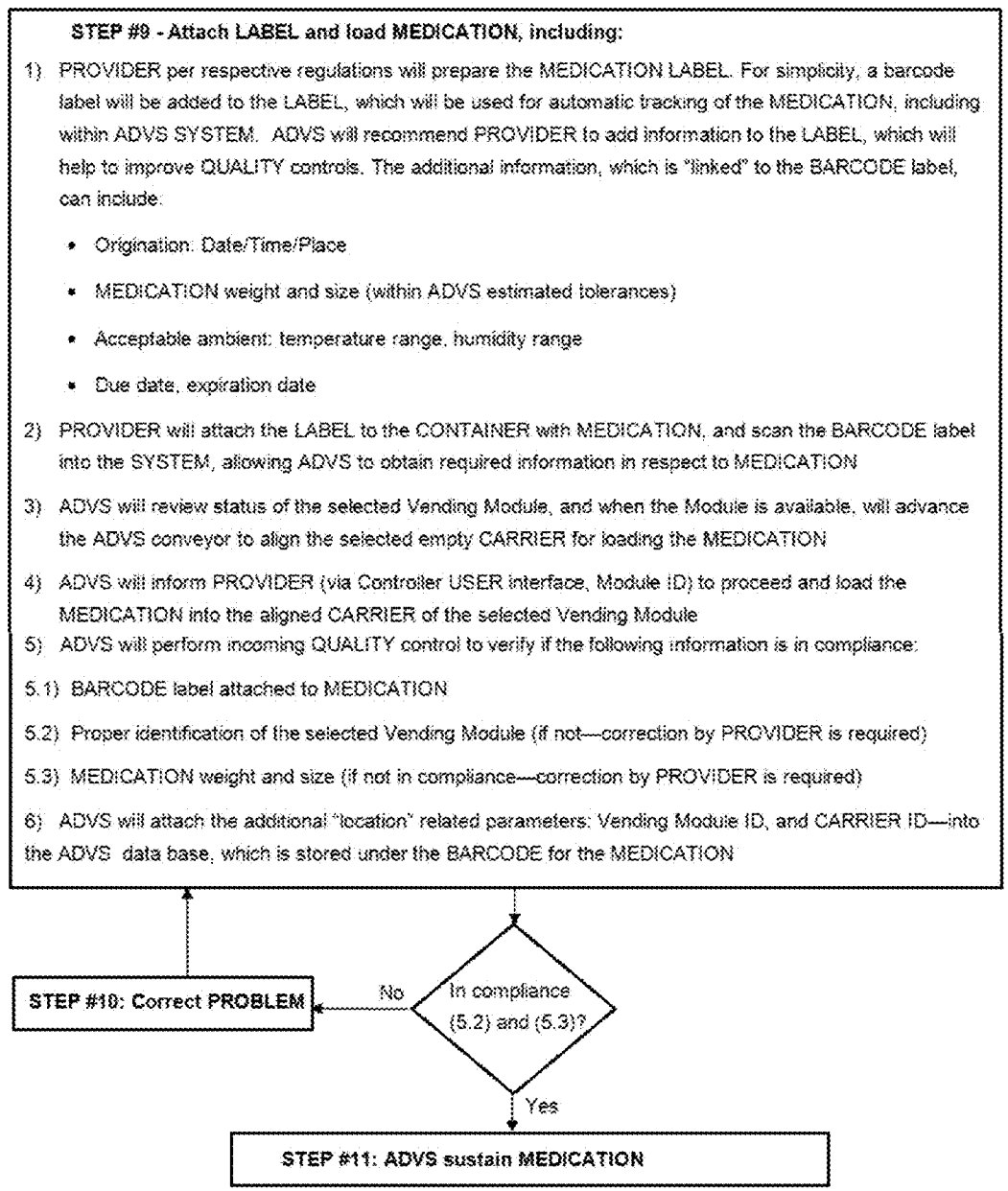
Figure 57:
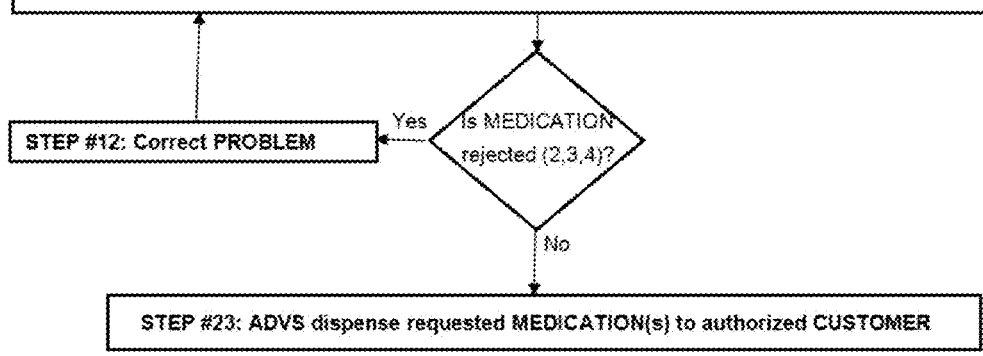

FIG. 51—illustrates the following AADVS QUALITY control ALGORITHM process STEPS, with additional comments and clarifications listed below.

STEP #1—Verification by PROVIDER of the PRESCRIPTION compliance to required regulations, including: verification of prescription issued by an authorized physician of the MEDICATION to a CUSTOMER. If in compliance to regulations, proceed to STEP #3, otherwise—proceed to STEP #2, including PROVIDER to correct the problem per respective procedures, STEP #3: PROVIDER reviewing specifications for MEDICATION listed in the prescription. Within available resources and configurations of the AADVS SYSTEM, PROVIDER to select respective AADVS process STEPS required to provide QUALITY MEDICATIONS and QUALITY SERVICES to respective CUSTOMER, with MEDICATIONS in full compliance to respective specifications, including:
1) Maintaining MEDICATIONS within required safety and security requirements, and making the MEDICATIONS available to authorized CUSTOMER at specified location, within requested due date.
2) Selecting respective MEDICATION type from approved list of brands and vendors, and identifying MEDICATION unit dosage and total amount of units.
3) Maintaining MEDICATIONS within required environment from the point of origination to the point of dispensing to the authorized CUSTOMER.

STEP #4: PROVIDER preparing MEDICATIONS per verified PRESCRIPTION and respective specifications. This STEP includes AADVS quality verification in respect to the weight of the issued MEDICATION in compliance to the weight calculated by the AADVS. Regardless, whether the amount of MEDICATION is issued by a non-AADVS equipment, such as pill counters, the total weight of the MEDICATION must be within the tolerances of the weight calculated by the AADVS. AADVS controllers based on information provided by the PROVIDER, and direct access to the data base of available raw materials, will calculate the expected wait of the total MEDICATION, and based on: accuracy specifications of the AADVS scales and measured ambient environment, will calculate the expected weight range for the MEDICATION. If the measured weight of the MEDICATION is in compliance, proceed to next STEP, otherwise—proceed to STEP #5, including PROVIDER to correct the problem per respective procedures.

STEP #6: Based on available AADVS resources, and CUSTOMER QUALITY service CRITERIA, the PROVIDER will select either the onsite (STEP #6) or offsite (STEP #7) AADVS dispensing of MEDICATIONS to authorized CUSTOMER.

STEP #6: The AADVS QUALITY control ALGORITHM will allow PROVIDER to optimize the use of available resources, including onsite AADVS SYSTEM resources, end achieve the objective of providing only QUALITY MEDICATIONS to authorized CUSTOMERS, and providing onsite QUALITY services to CUSTOMERS while sustaining operating objectives in terms of business efficiency. If any of the AADVS QUALITY verifications failed, the PROVIDER will need to follow STEP #8 and correct the problem, otherwise the PROVIDER will proceed with STEP #9.

STEP #7: The AADVS QUALITY control ALGORITHM will allow PROVIDER to optimize the use of available resources, including offsite AADVS SYSTEM resources, and achieve the objective of providing only QUALITY MEDICATIONS to authorized CUSTOMERS, and providing offsite QUALITY services to CUSTOMERS while sustaining operating objectives in terms of business efficiency. If any of the AADVS QUALITY verifications failed, the PROVIDER will need to follow STEP #8 and correct the problem, otherwise the PROVIDER wilt proceed with STEP #20.

STEP #9: The AADVS QUALITY control ALGORITHM will guide the PROVIDER, and also assist the PROVIDER in performing QUALITY verification steps. If any of the AADVS QUALITY verifications failed, the PROVIDER will need to follow STEP #10 and correct the problem, otherwise the PROVIDER will proceed with STEP #11.

STEP #11: The AADVS configurations include configurations monitoring the environment surrounding the MEDICATION, and configurations also sustaining the environment surrounding the MEDICATION within set specification requirements by the QUALITY control ALGORITHM. If any of the AADVS QUALITY verifications failed, the PROVIDER will need to follow STEP #12 and correct the problem, otherwise the PROVIDER will proceed with STEP #13.

STEP #13: Each MEDICATION prior to dispensing will undergo the final QUALITY verifications, including the final verification of the history of previously performed verifications, and only MEDICATIONS in full compliance will be made available for dispensing to authorized CUSTOMER. If any of the AADVS QUALITY verifications failed, the PROVIDER will need to follow STEP #14 and correct the problem, otherwise the PROVIDER will proceed with STEP #15.

STEP #15: The AADVS configurations include configurations supporting high speed dispensing of requested MEDICATIONS to an authorized CUSTOMER. The CUSTOMERS will have an option to request confirmation report in respect to QUALITY of each MEDICATION they will receive, as well as instructions in respect to each MEDICATION. The format of requests supported, include: onsite printout (hard copy); online (email). The AADVS user interfaces for the CUSTOMER include: touch-screen display with audio headphones, as needed; LED status indicator; credit card reader; control buttons; printer output. The AADVS configurations will include configurations in support of providing respective services to handicapped CUSTOMERS, in compliance to respective regulations.

STEP #20: The AADVS configurations include configurations supporting transportation of MEDICATIONS inside the AADVS Portable Vending Cartridges (PVC), which are stored inside AADVS Vending Modules (AVM) designated for transporting PVC's to their destination. If any of the AADVS QUALITY verifications failed, the PROVIDER will need to follow STEP #10 and correct the problem, otherwise the PROVIDER will proceed with STEP #21.

STEP #21: The AADVS configurations include configurations supporting delivery of MEDICATIONS to designated locations outside the pharmacy business, which is specified by the CUSTOMER, including: AADVS Vending Modules configured as stand-alone kiosks; hospitals; care facilities. For services outside the pharmacy, once at the destination, the authorized PROVIDER will dispense the MEDICATION from respective AVM, and then personally deliver the MEDICATION to authorized CUSTOMER. All transportation methods supported by the AADVS ensure full compliance of the MEDICATIONS to the respective specifications at all times. If any of the AADVS QUALITY verifications failed, the PROVIDER will need to follow STEP #10 and correct the problem, otherwise the PROVIDER will proceed with STEP #22.

STEP #22: All transportation methods supported by the AADVS ensure full compliance of the MEDICATIONS to the respective specifications at all times. If any of the AADVS QUALITY verifications failed, the PROVIDER will need to follow STEP #10 and correct the problem, otherwise the PROVIDER will proceed with STEP #23.

STEP #23: For services at a remote pharmacy, the respective steps are listed under STEP #13. For services at a remote AADVS Vending Module configured as a KIOSK, the respective steps are listed under STEP #13. For services at: residency; hospitals; care facilities, the respective include: at the destination, the authorized PROVIDER will dispense the MEDICATION from the respective PVC stored inside respective AVM, and then personally deliver the MEDICATION to authorized CUSTOMER. All transportation methods supported by the AADVS ensure full compliance of the MEDICATIONS to the respective specifications at all times. If any of the AADVS QUALITY verifications failed, the PROVIDER will need to follow STEP #10 and correct the problem, otherwise the PROVIDER will proceed with STEP #22.

Figure 61:
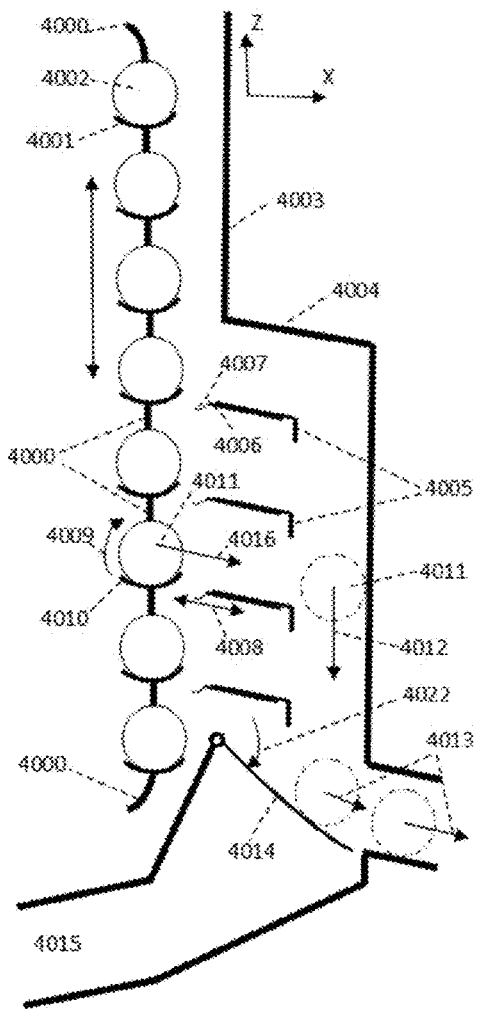

FIG. 61—illustrates Z-X view of a section of AADVS CONVEYOR (4000) configured for VERTICAL indexing along Z-axis in either direction, as indicated by the bi-directional arrow, and for automatic unloading of ITEMS from selected CARRIERS by AADVS Dispensing Tunnel (4004). The CONVEYOR (4000) configurations include configurations illustrated on FIG. 26, which are configured for indexing ITEMS inside the CARRIERS illustrated on FIGS. 6-12, 45, 46. These configurations support automatic unloading, as described below. The CONVEYOR (4000) configurations include indexing configurations and layouts as described for FIGS. 27 through 41. As shown, ITEM (4011) from CARRIER (4010) is selected by AADVS for dispensing along the directions (4012, 4013) toward a pick-up bin (not shown for simplicity), where it will be picked up by an authorized CUSTOMER. The process of authorization of a CUSTOMER via AADVS interface (not shown for simplicity) includes verifications of: ID; appropriate selection of MEDICATIONS within AADVS (4000) allocated to the CUSTOMER; payments made for MEDICATIONS selected. The ITEM (4011) must be in full compliance to AADVS QUALITY control ALGORITHM requirements, with respective AADVS devices (not shown for simplicity) used by AADVS QUALITY control performing QUALITY verifications, including: incoming, prior to accepting the ITEM (4011) into AADVS (4000); in-process while ITEM (4011) is residing within AADVS (4000); and final prior to dispensing the ITEM (4011) to authorized CUSTOMER. The AADVS QUALITY control verifications include: specifications parameters related to the ITEM (4011), such as: weight, size, ID label; due date; and process specifications parameters in respect to the environment verifications surrounding the ITEM (4011); security verifications in respect to ITEM (4011), including: verification of locations within AADVS (4000); system level verifications of AADVS (4000), including: monitored access to enclosing panels—all complied while the ITEM (4011) was residing inside the AADVS (4000). The illustrated process applies to all ITEMS stored inside AADVS (4000). The CONVEYOR (4000) configurations include configurations shown on FIGS. 25 through 49. The CARRIER (4001) configurations include configurations shown on FIGS. 6-12, 16-24, 42-46. The Dispensing Tunnel (4004) configurations include configurations shown on FIGS. 13-15.

NOTE: For AADVS CONVEYOR configurations, including indexing of multi-ITEM POCKET CARRIERS illustrated on FIGS. 16 through 25, the dispensing of respective multi-ITEM POCKETS from the respective CARRIERS will include configurations, not shown for simplicity, which will allow authorized personnel to gain access to the respective CARRIER and then manually remove the multi-ITEM POCKET from the CARRIER. The AADVS CONVEYOR systems for these configurations will include configurations supporting AADVS controllers to align selected CARRIER, primarily changing the angle of the CARRIER position around X-axis, and simplify access by authorized personnel to reach the multi-ITEM POCKET inside the CARRIER, including removal of the multi-ITEM POCKET from the CARRIER. After ITEMS are removed from the multi-item POCKET, the empty POCKET or POCKET reloaded with new ITEMS, will be manually loaded by the authorized personnel into the same CARRIER for further distribution along the CONVEYOR indexing route, including CONVEYOR layout configurations illustrated on FIGS. 27 through 41. The access by authorized personnel to CARRIERS inside the AADVS CONVEYOR includes configurations allowing AADVS controllers to open/close respective access doors, including access control configurations described in my PATENTS. The remaining elements are labeled as follows:

4001—CARRIER loaded with ITEM (4002)

4003—enclosure for AADVS components, including: CONVEYOR (4000). Dispensing Tunnel (4004), unloaded ITEM routing chutes (4013, 4015). The enclosure configurations include requirements in respect to full compliance to security requirements under AADVS QUALITY control ALGORITHM.

4005—stationary guiding PANEL, configured for guiding unloaded ITEMS from respective CARRIERS in direction (4016) toward the vertical chute. For simplicity, the configuration shown allows unloaded ITEMS under their own weight to move down the chute in direction (4012) toward the distribution GATE (4014). Other configurations include: additional AADVS components, such impact absorbing baffle plates along the perimeter of the chute; and a dedicated conveyor system incorporating the GATE (4014), which is synchronized by AADVS Controllers with the ITEM unloading process steps, and transporting each unloaded ITEM down, with the integrated GATE (4014) directing the ITEM at the bottom toward the respective exit chute.

4006—Sliding PANEL with attached flexible GRIP (4007) at the end facing the CONVEYOR (4000). The PANEL (4006) is configured under control from AADVS Controllers to advance forward and beck, as indicated by direction arrows (4006). The unloading process steps, for example of CARRIER (4010), include:

1) CONVEYOR (4000) aligning the CARRIER (4010) in respect to selected Sliding PANEL (4006)
2) Advancing the PANEL (4006) toward the CARRIER (4010), with the flexible GRIP (4007) engaging with the CARRIER, and swinging the CARRIER around Y-axis, as indicated by direction arrow (4009), to an angle at which point the ITEM (4011) inside the CARRIER (4010) under its own weight will slide-out of the CARRIER and move along the PANEL (4006) in the direction (4016)
3) The ITEM (4011) continue sliding downward along the stationary PANEL (4005), and then going down in direction (4012) along the vertical chute of (4004), reaching the GATE (4014).

The AADVS controls of all PROCESS STEPS, including ITEM unloading, include AADVS components (SENSORS, DRIVERS) which are used by AADVS Controllers to precisely execute required motion controls of respective AADVS components in compliance to requirements of the AADVS QUALITY control ALGORITHM.

Figure 62:
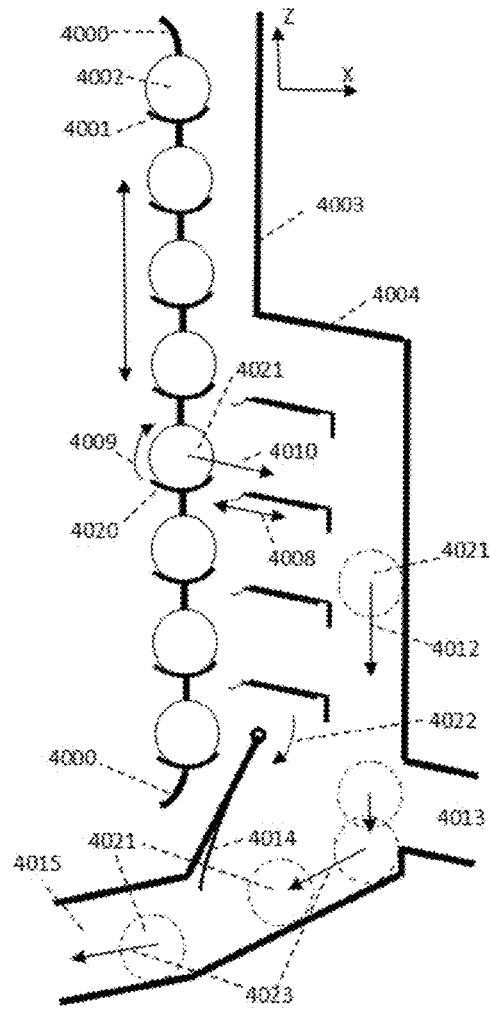

4014—GATE, which is controlled by AADVS Controllers. The GATE configurations include configurations illustrated on FIGS. 61, 62, 64, with the GATE placed by the AADVS Controller in three positions: 1) As shown on FIG. 64, the unloaded ITEM is on the top of the GATE platform, and will remain there for AADVS to perform final QUALITY verifications prior to proceeding with the next PROCESS STEP; 2) As shown on this FIG. 61, directing the unloaded ITEMS in full compliance to AADVS QUALITY verifications in direction (4013), toward a pick-up bin (not shown for simplicity); 3) As shown on this FIG. 62, directing the unloaded ITEMS in direction (4023), toward a pick-up bin (not shown for simplicity) reserved for authorized PROVIDER;

FIG. 62—illustrates Z-X view of a section of AADVS CONVEYOR (4000) illustrated on FIG. 61, with ITEM (4021) from selected CARRIER (4020) aligned for unloading by AADVS Controllers for dispensing along the directions (4012, 4023) toward a pick-up bin (not shown for simplicity), where it will be picked up by an authorized PROVIDER. The routing of the ITEM (4021) to PROVIDER is result of conditions, including:
1) ITEM (4021) failing compliance to AADVS QUALITY control verifications, including the QUALITY verifications listed for FIG. 61, and as result—marked for REJECTION:
2) ITEM (4021) being requested by PROVIDER. The process of authorization of a PROVIDER via AADVS interface (not shown for simplicity) includes verifications of: PROVIDER ID; appropriate selection of MEDICATIONS within AADVS (4000).

Figure 63:
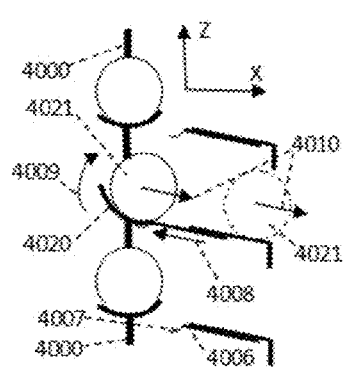

FIG. 63—illustrates Z-X view details in respect to unloading the ITEM (4021) from the CARRIER (4020), shown on FIG. 62. The unloading PROCESS STEPS are same as described for FIG. 61, with application toward CARRIER (4020). The respective slideable PLATE (4006) is advanced toward the CARRIER (4020), engaging the TONGUE (4007) of the PLATE (4006) with the CARRIER (4020), resulting in the TONGUE (4007) tilting the CARRIER (4020) around Y-axis in direction (4009) at an angle (not marked for simplicity), and allowing the ITEM (4021) under its own weight to slide out of the CARRIER (4020) toward the PLATE (4006). Respective AADVS components, including SENSORS, are used by AADVS Controllers for verification of the locations of the CARRIERS and ITEMS within AADVS, including PROCESS STEPS of: ITEM loading into AADVS, ITEM sustaining within AADVS; and ITEM unloading from AADVS, all in compliance to requirements of the AADVS QUALITY control ALGORITHM.

Figure 64:
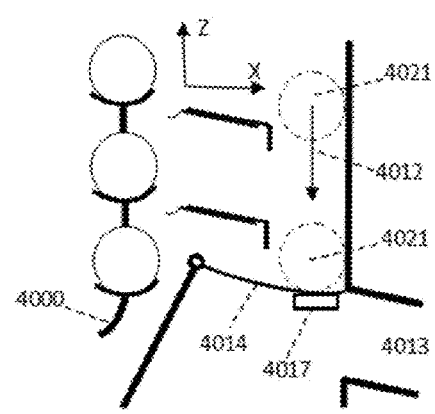

FIG. 64—illustrates Z-X view details in respect to AADVS controls related to final QUALITY verifications of unloaded ITEM (4021) from the CARRIER (4020). The configurations of the final QUALITY verification includes configuration shown on FIG. 64. The GATE platform (4014) is positioned by AADVS Controllers to retain unloaded ITEM (4021) from the CARRIER (4020), and allow AADVS QUALITY verification devices to perform final verifications. For simplicity, the final QUALITY inspection illustrates verification of the weight of the unloaded ITEM (4021). The configurations of the SCALE (4017) include configurations of the SCALE being either integrated into GATE (4014), or advanced by AADVS Controllers to position under the GATE (4014), as shown. The AADVS Controllers and AADVS components, including the pathway of the unloaded ITEMS along the direction (4012), are configured to provide reliable decent of the unloaded ITEMS, one at a time, down toward the GATE (4014), with minimum impact on the ITEM and AADVS. In addition to weight verification, as shown, respective AADVS devices can be configured and positioned accordingly for performing additional QUALITY verifications, including verification of the identity of the unloaded ITEM ID (such as a barcode label), as required by the AADVS QUALITY control ALGORITHM. After final verification, the unloaded ITEMS, including ITEM (4021), will be directed by the GATE (4014) toward either: CHUTE (4013), as shown on FIG. 61; or toward CHUTE (4015), as shown on FIG. 62. The distribution of the unloaded ITEM (4021) will be acknowledged by the AADVS Controllers, including informing respectively the PROVIDER and/or authorized CUSTOMER via respective USER interfaces. Results of QUALITY verifications performed by AADVS QUALITY control ALGORITHM in respect to an ITEM within AADVS, and results of QUALITY verifications of the environment and security while the ITEM is within AADVS, are recorded by AADVS Controllers in non-volatile memory, with respective reports available per requests of authorized PROVIDER and/or authorized CUSTOMER. The AADVS configurations of the unloading TUNNEL (4004), shown on FIG. 61, 62—includes AADVS configurations supporting synchronized, nearly simultaneous, unloading of several ITEMS (BATCH processing) from respective CARRIERS (BATCH of ITEMS), requested by an authorized CUSTOMER or PROVIDER, and then holding the unloaded BATCH of ITEMS on the GATE (4014), while the final QUALITY verifications of weight of the ITEMS loaded on top of GATE (4014), and/or verification of change (reduction) in weight of the CONVEYOR (4000), are compared to the anticipated calculated results, performed by AADVS QUALITY control ALGORITHM. The resulting AADVS distribution PROCESS STEPS will apply to the entire BATCH of ITEMS.

Figure 65:
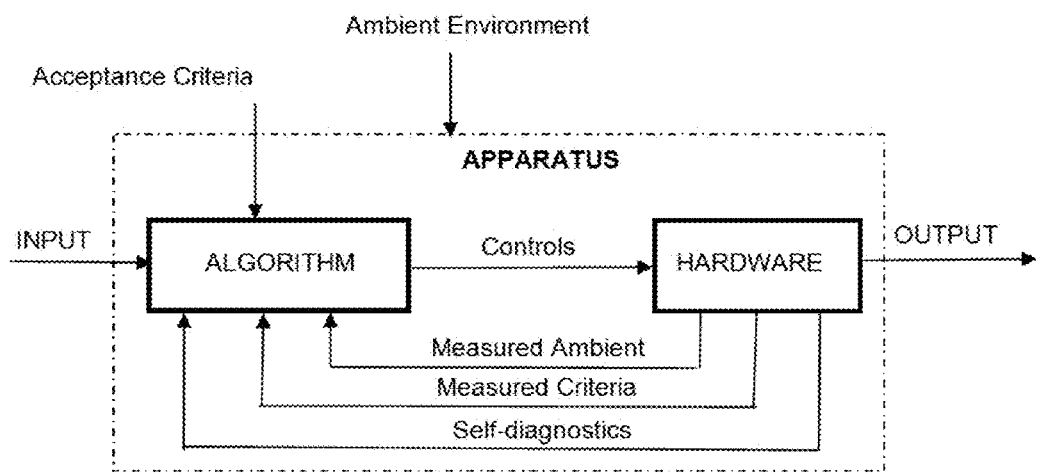

FIG. 65—illustrates a block-diagram of an Apparatus, Adaptable Automatic Distributed Vending System (AADVS). The Apparatus shown on the block-diagram comprising of at least one configurable hardware component and at least one configurable software component operating within an acceptance criteria of distributing of an least one item from a point of origination to a point of destination adaptable to an ambient environment and an internal self-diagnostics; wherein said hardware component including at least one intelligent controller monitoring sensors, including sensors representing said ambient environment and said self-diagnostics; wherein said software component including an algorithm executing a real-time control over said controller; wherein said algorithm sustaining operation of said apparatus within said acceptance criteria; wherein said item originated according to a specification; wherein said specification created by an authorized operator or a computer, and includes at least one or combination of the following specification parameters: authorization for producing said item; materials said item should be produced from; volume, quantity and size of a unit(s) comprising said item; ambient environment for sustaining said item; origination location; destination location; due date of availability at the destination; and authorization parameters for obtaining said item at the destination; wherein said acceptance criteria including one or combination of the following criteria: said apparatus performing verification of said item compliance to at least one parameter of said specification; said apparatus sustaining, distributing and delivering said item in compliance to the at least one parameter of said specification; said apparatus in real-time monitoring of said ambient environment and/or monitoring results of said internal self-diagnostics, and automatically in real-time adapting to sustain said item in compliance to the at least one parameter of said specification at all times; and said apparatus rejecting an item out of specification; wherein said sensors monitoring an internal environment within said apparatus; said internal environment including: temperature, humidity, vibrations within said apparatus; wherein said sensors monitoring motion parameters of a mechanical and electronic components comprising a conveyor, said motion parameters including: accuracy, acceleration, speed, deceleration, vibrations; wherein said sensors monitoring communication interferences within said apparatus and interferences between said apparatus and an external controller or a device; wherein said acceptance criteria including an acceptable range of a status of said sensors; wherein said acceptance range is defined by said acceptance criteria; wherein said controller monitoring said status of said sensors, including said status representing said ambient environment and said self-diagnostics; wherein said controller comparing said status to said acceptable range and executing controls in real-time to sustain said apparatus within said acceptance criteria; wherein said item includes a medication or a medication accessory, said medication including a prescription medication wherein said item includes a medication or a medication accessory; said medication including a prescription medication; wherein said acceptance criteria include said apparatus sustaining said item within said specification; wherein said adaptability of said apparatus to said acceptance criteria includes said apparatus executing a control algorithm; said algorithm monitoring an environment surrounding said apparatus, including one or combination of: temperature, vibration, and/or humidity and monitoring a self-diagnostic results of said apparatus, including one or combination of internal temperature, accuracy of transporting conveyor, stability of transporting conveyor, and said algorithm executing in real-time controls sustaining operation of said apparatus within said acceptance criteria.

The Apparatus shown on the block-diagram supporting a method of configuring the apparatus for providing distribution of items in compliance to a predefined acceptance criteria, and the method adaptable in real-time to ambient environment and adaptable in real-time to internal self-diagnostics of hardware and software of the apparatus, and the apparatus sustaining in real-time all items within the apparatus in compliance to the acceptance criteria; said environment includes external to the apparatus: temperature, vibrations, humidity; said self-diagnostics include internal to the apparatus: temperature, vibrations, humidity, motion accuracy, communication accuracy; and the method consisting of: a) Configuring the acceptance criteria to include a specification for individual item, and a specification for a control algorithm operating said apparatus; b) Configuring the specification for individual item to include a customer specific parameters; c) Configuring the specification for the control algorithm to include real-time adaptability to ambient environment, and real-time adaptability to a self-diagnostics of the apparatus; d) Configuring the hardware for monitoring the ambient environment surrounding the apparatus, and for executing real-time self-diagnostics of the apparatus; e) Configuring the hardware of the apparatus to include at least one intelligent controller executing a control algorithm; f) Programming the control algorithm to execute real-time tasks including: calculating item quality acceptance parameters based on the specification for the item; performing verification of the item quality acceptance parameters prior to accepting the item into the apparatus, and performing rejection of an item failing the quality acceptance; sustaining items within the apparatus in compliance to respective item acceptance parameters, and performing rejection of an item failing the quality acceptance; calculating apparatus quality acceptance parameters for the apparatus; performing self-diagnostics of the apparatus for verification of the apparatus compliance to the apparatus acceptance parameters; monitoring ambient environment, and executing real-time controls of the apparatus, sustaining the apparatus within the apparatus specification parameters; interfacing in real-time with intelligent controllers of the apparatus and intelligent controllers outside the apparatus to support network controls of the acceptance criteria for the apparatus as a part of or comprising of an entire adaptable automatic distributed vending system; said interface including wireless network for mobile devices, LAN and INTERNET; calculating the most optimum configuration and utilization of the apparatus resources for sustaining items within the apparatus in compliance to the respective quality acceptance criteria, and the apparatus adaptable to ambient environment and internal self-diagnostics, and the apparatus operating within respective specification acceptance criteria including on-time delivery of the items for distribution to an authorized operator or customer, directing distribution of items within the apparatus to minimize probability of an error in identification of an item based on the item specification parameters, including but not limited to the weight and the size of the container with medication.

The description of the elements shown on the FIG. 65:

INPUT—is defined as a SPECIFICATION requirement for the APPARATUS of completing a specific PROCESS in order to convert the INPUT into an OUTPUT. The APPARATUS can be configured for executing an entire SPECIFICATION, or a selected section of the SPECIFICATION. The PROCESS includes, but not limited to, a number of logistic and technological steps required to be completed by the APPARATUS in order to achieve SPECIFICATION parameters. The SPECIFICATION includes PROCESSES performed over PHYSICAL matters (technological steps, as an example), and/or VIRTUAL matters (logistic steps, as an example). The initial state of the PHYSICAL matter include: raw material; and/or partially PROCESSED material. The initial state of the VIRTUAL matter include: "ground zero" state, i.e. no presence of a VIRTUAL matter, and/or partially PROCESSED VIRTUAL material.

AMBIENT ENVIRONMENT—is defined as environment surrounding the APPARATUS, including but not limited to the following ambient parameters: temperature, vibrations, humidity, electro-magnetic interferences.

The ENVIRONMENT could impact the HARDWARE components of the APPARATUS; example: rising temperature and/or vibrations may impact the accuracy of indexing a transport conveyor. The ENVIRONMENT could impact the SOFTWARE components of the ALGORITHM; example: electro-magnetic interferences affecting communications. The APPARATUS will monitor AMBIENT environment through respective sensors, and then provide results of the measurements labeled as "Measured Ambient" to the ALGORITHM.

SELF-DIAGNOSTICS—is defined as a number of test conducted by the APPARATUS in real-time in order to establish the state of its components, including hardware and software. The APPARATUS will conduct in real-time internal self-diagnostics using respective sensors, and report results labeled as "Self-Diagnostics" to the ALGORITHM.

ACCEPTANCE CRITERIA—is defined as acceptable parameters of the APPARATUS performance in real-time. The CRITERIA include, but not limited to: the APPARATUS executing in-real time PROCESS controls in order of sustaining compliance of the INPUT transitions to the OUTPUT in accordance to the SPECIFICATIONS, and under varying normal operating ENVIRONMENT, and/or SELF-DIAGNOSTICS; the APPARATUS adapting to ENVIRONMENT by executing in real-time required adjustments of the PROCESS controls in order to compensate for measured ENVIRONMENT being out of the normal range, and/or SELF-DIAGNOSTICS approaching the respective limits set by CRITERIA; and the APPARATUS sustaining required levels of efficiency and reliability, by adapting to the ENVIRONMENT. The APPARATUS will in real-time monitor the actual state of the parameters associated with the ACCEPTANCE CRITERIA, and report the status labeled as "Measured Criteria" to the ALGORITHM. The ACCEPTANCE CRITERIA could be configured to require the APPARATUS adapting to ambient ENVIRONMENT by maintaining specified safety margins for SELF-DIAGNOSTIC parameters. The ACCEPTANCE CRITERIA could include requirements for the APPARATUS to employ respective technologies preventing negative impacts of electro-magnetic interferences on HARDWARE and SOFTWARE.

EXAMPLE 1

SELF-DIAGNOSTIC parameter related to internal temperature of a component within the APPARATUS would have a safety margin of 20 C from the maximum limit of 80 C at ambient TEMPERATURE of 30 C. The ALGORITHM, according to ACCEPTANCE CRITERIA, would be required to monitor ambient TEMPERATURE, and the APPARATUS regulating as a function of the ambient TEMPERATURE the power dissipation of the component in order to maintain the safety margin of 20 C. The component could be: motor driving the conveyor belt; driver circuit controlling the motor; solenoid. The adaptability of the APPARATUS to ambient ENVIRONMENT in respect to the motor, would include controls (per ALGORITHM) lowering the speed and/or acceleration of the motor as function of ambient TEMPERATURE.

EXAMPLE 2

SELF-DIAGNOSTIC parameter related to indexing accuracy of the motor and/or the belt advancing the conveyor. Assuming the index accuracy safety margin of +/−0.125" at ambient TEMPERATURE of 30 C and VIBRATIONS below a specified level. The ALGORITHM, according to ACCEPTANCE CRITERIA, would be required to monitor ambient TEMPERATURE and VIBRATIONS, and the APPARATUS as a function of the ambient TEMPERATURE and VIBRATIONS regulating the motor control parameters to sustain the accuracy within the safety margin. The adaptability to ambient ENVIRONMENT in respect to the accuracy would include controls (per ALGORITHM) lowering the speed and/or acceleration of the motor as a function of ambient TEMPERATURE and VIBRATIONS.

EXAMPLE 3

SELF-DIAGNOSTICS detecting presence of electromagnetic interferences, and the ALGORITHM based on measured data, activating and regulating in real-time respective hardware and/or software filters to sustain operation of the APPARATUS within ACCEPTANCE CRITERIA.

ALGORITHM—is defined as a software component of the APPARATUS responsible for, but not limited to, the following tasks:
a) Analyzing the INPUT SPECIFICATION and defining required PROCESS steps in order for the APPARATUS to remain within compliance to the ACCEPTANCE CRITERIA;
b) Analyzing in real-time the FEEDBACK results of monitoring the AMBIENT ENVIRONMENT ("Measured Ambient"), SELF-DIAGNOSTICS ("Self-Diagnostics"), and actual state of the ACCEPTANCE parameters ("Measured Criteria");
c) Based on the FEEDBACK and the ACCEPTANCE CRITERIA, the ALGORITHM executing real-time "Controls" over the HARDWARE of the APPARATUS, including controls of the PROCESS steps in order for the APPARATUS to remain within the ACCEPTANCE CRITERIA; The controls can include one or combination of: discrete controls (controls based on pre-defined levels); and/or continuous control function (controls as function of changing ENVIRONMENT);
d) Reporting in real-time as required by the ACCEPTANCE CRITERIA when the APPARATUS (including a single PROCESS step) is out of ACCEPTANCE, and executing respective REJECTION PROCESS steps to eliminate a possibility of an OUTPUT being out of SPECIFICATIONS reaching a CUSTOMER.

The internal communications and/or controls within the APPARATUS, and external communications between the APPARATUS and an external HOST or controller, include: wired; wireless; and INTERNET technologies. The method of communications and the format of data being communicated includes a variety of technologies, selected with an objective to achieve the ACCEPTANCE CRITERIA. APPARATUS configuration example: AADVS configured for a single story Pharmacy (as shown on FIG. 1), and consisting of:
a) Six independent vertical Automatic Vending Modules (AVM), labeled 5, 10 (4 units), and 16, as described for FIG. 1
b) Support components, FIG. 1 labeled 2000, 2001, for verification of quality of PRESCRIPTION MEDICATION compliance to SPECIFICATIONS prior to entry into the AADVS, as described for FIGS. 50 through 60.
c) Support components for verification of quality of PRESCRIPTION MEDICATION compliance to SPECIFICATIONS while remaining inside AADVS, as described for FIGS. 51 through 60.
d) Support components for verification of quality of PRESCRIPTION MEDICATION compliance to SPECIFICATIONS just prior to dispensing to an authorized CUSTOMER, as described for FIGS. 51-60.

INPUT—is the SPECIFICATION for a PRESCRIPTION medication issued by an authorized doctor and/or computer. The SPECIFICATION parameters will include: ID of an authorized entity; ID of an authorized customer; a customer specific: medication type, quantity, dosage, instructions, location for delivery or dispensing, required date and time of availability at the location, method of communication with the customer via phone, email and text. The PROCESS steps of the SPECIFICATION will include: AADVS calculating total weight of the MEDICATION to be completed per PRESCRIPTION; AADVS calculating required volume to store and/or package the MEDICATION; AADVS selecting a specific size of a CONTAINER for storing, transporting and delivering the MEDICATION; AADVS calculating total weight of the MEDICATION inside the selected CONTAINER; AADVS selecting the transportation routing to achieve quality parameters listed under ACCEPTANCE CRITERIA; AADVS monitoring location of the PRESCRIPTION inside the APPARATUS; AADVS monitoring ambient ENVIRONMENT inside the APPARATUS surrounding the MEDICATION; the steps are illustrated and described on FIGS. 1, 50, 51.

SELF-DIAGNOSTICS—will include AADVS monitoring: performance parameters of the conveyor transport system (speed, index accuracy, vibrations; temperature of the drive mechanics); orientation of the carriers; availability of the carriers; status of carriers (empty, loaded, in-service), as described for FIGS. 3-5, 8-10, 13-15, 50-64, 67.

ACCEPTANCE CRITERIA—will include acceptable parameters of the AADVS performance in real-time. The CRITERIA will require the AADVS executing in-real time PROCESS controls, as described for FIGS. 51-60, in order of sustaining compliance of the INPUT transitions to the OUTPUT in accordance to the SPECIFICATIONS, and the AADVS adapting to varying normal operating ENVIRONMENT, and/or SELF-DIAGNOSTICS by executing in real-time required adjustments of the PROCESS controls in order to compensate for measured ENVIRONMENT being out of the normal range, and/or SELF-DIAGNOSTICS approaching the respective limits set by CRITERIA; and the AADVS sustaining required levels of efficiency and reliability, by adapting to the ENVIRONMENT.

Example of the AADVS adapting to ENVIRONMENT:
a) The ENVIRONMENT is approaching the LIMITS, while still within the OPERATING specifications.

CASE 1: Ambient temperature at the very low LIMIT. The ACCEPTANCE criteria will require the ALGORITHM to adjust the controls to sustain reliability of the system, which includes: reducing speed of the transport conveyor; lowering acceleration rates; turning ON and regulating the internal heating components (heater, etc.). The controls can include one or combination of: discrete (based on pre-defined levels); and/or continuous function (controls as function of changing ENVIRONMENT). Further adaptability to temperatures below the LIMIT, will include stopping the transport conveyor and informing the OPERATOR.

CASE 2: Ambient temperature at the very high LIMIT. The ACCEPTANCE criteria will require the ALGORITHM to adjust the controls to reduce self-heating, such as: reducing speed of the transport conveyor; taking longer brakes in-between indexing the conveyor, turning ON and regulating the internal cooling components (fan, etc.).

CASE 3: Ambient vibrations approaching the upper LIMIT. The ACCEPTANCE criteria will require the ALGORITHM to adjust the controls to sustain reliability of the system as function of the measured vibrations, which includes: reducing speed of the transport conveyor; stopping lowering acceleration rates: turning ON and regulating the internal heating components (heater, etc.). The AADVS will in real-time monitor the actual state of the parameters associated with the ACCEPTANCE CRITERIA, and report the status labeled as "Measured Criteria" to the ALGORITHM. The ACCEPTANCE CRITERIA are listed under FIGS. 51-60.

ALGORITHM—as described in details for FIGS. 51-60 will be responsible for the following AADVS tasks:
a) Analyzing the INPUT SPECIFICATION and defining required PROCESS steps in order for the AADVS to remain within compliance to the ACCEPTANCE CRITERIA. Example of the PROCESS STEPS are illustrated on FIGS. 51-60;
b) Analyzing in real-time the FEEDBACK results of monitoring the AMBIENT ENVIRONMENT ("Measured Ambient"), SELF-DIAGNOSTICS ("Self-Diagnostics"), and actual state of the ACCEPTANCE parameters ("Measured Criteria");
c) Based on the FEEDBACK and the ACCEPTANCE CRITERIA, the ALGORITHM executing real-time "Controls" over the HARDWARE of the AADVS, including controls of the PROCESS steps in order for the AADVS to remain within the ACCEPTANCE CRITERIA:

Reporting in real-time per the ACCEPTANCE CRITERIA when the AADVS (including a single PROCESS step) is out of ACCEPTANCE, and executing respective REJECTION PROCESS steps to eliminate a possibility of an OUTPUT being out of SPECIFICATIONS reaching a CUSTOMER. Example of the REJECTION PROCESS illustrated on FIGS. 60 through 64. The Internal communications and/or controls within the AADVS, and the external communications between the AADVS and an external HOST or controller, include: wired; wireless; and INTERNET technologies. The method of communications and the format of data being communicated includes a variety of technologies, selected with an objective to achieve the ACCEPTANCE CRITERIA of the INPUT being PROCESSED to an OUTPUT.

Figure 66:
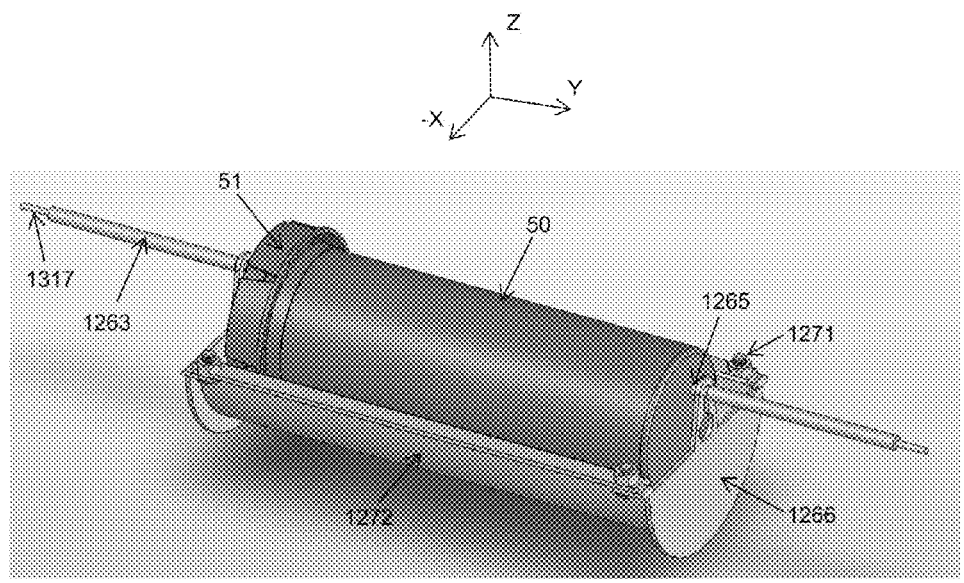

FIG. 66—3D illustration of an ITEM carrier assembly, based on the original sketches shown on FIGS. 11 and 12. The ITEM (not shown) can be stored inside the cylindrical container consisting, which consists of a body (cylinder enclosure—50) and a removable lid/cap (51). As shown, the container (50, 51) is loaded into the carrier pocket (1272). The side support brackets of the carrier pocket (1266L and 1266R) are attached to the pocket (1272) via mounting hardware (1271). The carrier support shafts (1263) on one side are inserted into a support bearing or a plain round cylindrical opening attached or embedded into the drive belt (reference FIGS. 47-49), and on the side facing the carrier—the shafts have a slot, controlled by the barrier (1265) and retaining the carrier side support brackets inside the slot. The entire configuration of the mechanical parts are designed to allow the carrier assembly (1272, 1266) to swing about the center horizontal Y-axis of the support shaft (1263), and the carrier essentially maintaining vertical alignment of the entire assembly in respect to Z-axis based on the weight of the carrier and the container inside applying pressure in the opposite direction (−Z). In addition, the inner surface of the pocket (1272) facing the container can be configured to prevent or minimize the rotation of the container inside the pocket. The vertical self-aligning feature of the carrier and the container inside, combined with restricted motion of the container inside the pocket, will essentially eliminate or minimize any impact on the ITEM inside the container during the motion of the conveyor. This is in particular important when an ITEM includes a number of prescription pills, with each pill, as required by specification, to maintain a specific volume of medication at all times. This applies to all carriers within the AADVS. This is one of the most important features of the AADVS conveyor system, allowing the system sustaining prescription medications volume during numerous indexing motions of the conveyor.

Figure 67:
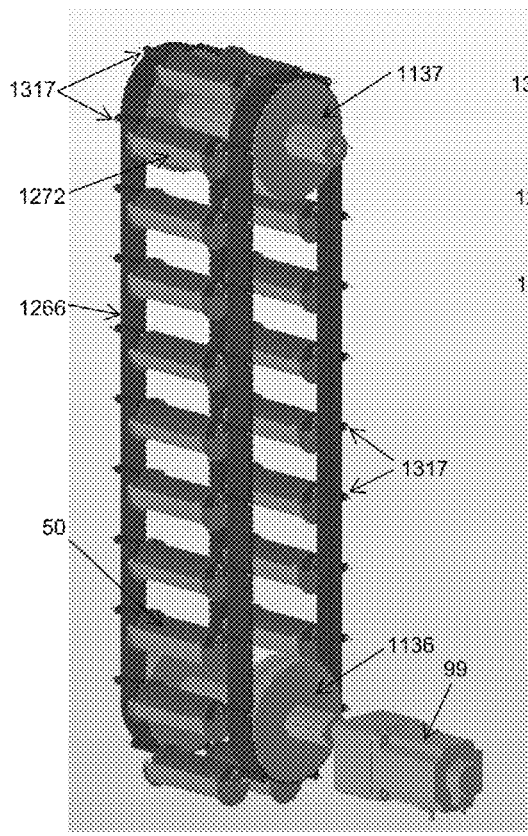

FIG. 67—3D illustration of a configuration of AADVS vertical conveyor transport system, based on a timing belt (1266) with embedded bearings to accept the carrier support shafts. For simplicity, not all components are shown, including supports for the conveyor: motor drive assembly (99), drive timing pulley (1136) and Idle timing pulley (1137)—are not shown. Remaining elements are labeled as on FIG. 66

Figure 68:
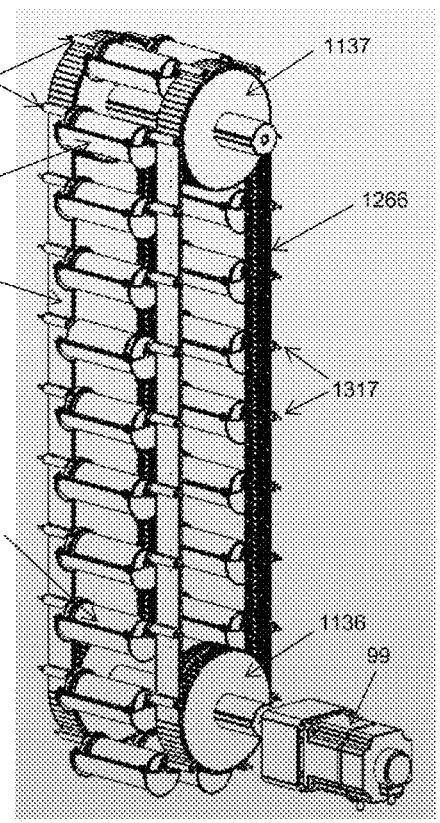

FIG. 68—3D illustration of additional details in respect to the AADVS vertical conveyor transport system shown on FIG. 67. As shown, the configuration of mechanical supports for the carriers ensure a self-vertical alignment of each carrier in respect to Z-axis under its own weight. Each carrier will have a carrier identification barcode label, as described on FIGS. 8-9. In addition, each carrier would have a "length measuring" barcode label as described on FIG. 10. Each container will have a specific barcode label identifying the medication stored inside the container. Verification of these barcode labels, including the length of the container inside a carrier, will be accomplished via respective optical devices, which could be installed at the very top of the conveyor, and reading the respective barcode labels as the carriers with the containers are either stationed under or moving under the barcode reading devices "looking" from the top down toward the barcode labels. The QUALITY verifications of the weight of the carrier with a container inside can be accomplished at the bottom of the conveyor, as described on FIGS. 42-48. The elements are labeled same as on FIG. 67.

What is claimed is:

1. A configurable apparatus adaptable for processing an item in compliance with a specification and in compliance to an acceptance criteria; said adaptability including configurations of said apparatus of a single or a multi-track configurable conveyor for distributing of the item vertically and/or horizontally; said item including a prescription medication; said specification for a prescription medication comprising of a specification parameters originated by an authorized physician (prescription specification) and a specification parameters originated by the apparatus (system specification); said acceptance criteria comprising processing and delivering a prescription medication in compliance to said specifications and to said acceptance criteria; said processing including storing a prescription medication inside a container and identifying said container with a set of specification parameters; said delivering including automatic dispensing to an authorized customer; and the apparatus executing a configurable control algorithm adaptable to said specifications and to said acceptance criteria;

said configurable apparatus comprising of;

a configurable controller; said controller including a configurable specification (SC) comprising of specification parameters (SCP);

a configurable non-volatile memory;

a configurable control algorithm; said algorithm including calculations/estimates of a probability of an error in processing a prescription medication by said apparatus including real-time monitoring and controls; said error including apparatus non-compliance to said acceptance criteria in respect to a prescription medication; said controls including closed-loop controls executed by said controller directly with or without assistance from an operator;

a configurable communication interface; said interface including: communication between said apparatus and a remote controller including a host controller, communication between said apparatus and a device with an embedded controller; said devices including mobile devices; said communication interface including wired, wireless and INTERNET; said interface including a configurable specification (SI) comprising of specification parameters (SIP); said (SI) and (SIP) including an operator interface and security specification approved by a provider;

a configurable sensor; said sensor interfaced to said configurable controller; said sensor including a configurable specification (SS) comprising of specification parameters (SSP); said (SS) including configurations for monitoring and/or measuring a specification parameter of said apparatus, including: ambient environment (including temperature, humidity, emissions, vibrations), shape of an item (including item as an individual pill or a container), dimension of an item (diameter or width, length, height), weight of an item, identification/specification of an item (barcode label and/or electronic identification/tracking device attached to an item) with said items including: a container, a carrier, a device and an assembly of said apparatus; said (SS) including configurations for monitoring self-diagnostics of said apparatus including self-diagnostics of: a device, an assembly, a module and/or a mechanism within said apparatus;

a configurable container; said container including a configurable specification for said container/housing (SH); said specification comprising of specification parameters (SHP) including: shape, size (volume/capacity and dimensions) and weight;

a configurable conveyor; said conveyor including: a transport mechanism and a carrier attached to said transport mechanism; said conveyor including a configurable specification (ST); said (ST) including configurations for: vertical, horizontal and angular direction; said (ST) including an attachment of a carrier; said attachment sustaining said carrier under the weight of said carrier (empty and/or loaded) in essentially vertical alignment, and allowing a weight measuring device (a sensor configured for weight measuring) to engage with said carrier lifting said carrier along a vertical axis and measuring the weight of said carrier (empty and/or loaded); said (ST) including bi-directional transport; said (ST) comprising of specification parameters (STP) including definition for: dimensional parameters, drive mechanism, local controller, communication interface to said controllers and a mechanical interface to a number of carriers;

a configurable dispensing module; said dispensing module including a configurable specification (SDM) comprising a specification parameters (SDMP); said (SDM) including: a mechanical interface with a dispensing conveyor for unloading an item from a carrier of said dispensing conveyor into said dispensing module and configurations for providing un-attended services comprising of a stand-alone vending kiosk in compliance to a quality acceptance criteria;

a configurable reject return module; said reject. module including a configurable specification (SRM) comprising a specification parameters (SRMP); said (SRM) including a mechanical interface with a reject return conveyor for unloading an item from a carrier of said conveyor into said reject return module;

a configurable customer interface; said customer interface including a configurable specification (SCI) comprising a specification parameters (SCIP); said (SCI) and (SCIP) including customer operational and security specifications;

a configurable provider interface; said provider interface including a configurable specification (SPI) comprising a specification parameters (SPIP); said (SPI) and (SPIP) including provider operational and security specifications;

a configurable vending module; said module including: said conveyors and said modules; said vending module including a configurable specification (SVM) comprising of specification parameters (SVMP); said (SVM) including: mechanical and electronic interfaces between said modules and configurations for providing un-attended services comprising the stand-alone vending kiosk; said (SVM) including compliance to: a vending module quality acceptance criteria and to a vending module safety/security acceptance criteria;

a configurable prescription medication; said medication including a configurable specification (SM); said specification comprising of a specification parameters originated by an authorized physician (prescription specification) and a specification parameters originated by the apparatus (system specification); said (SM) comprising of specification parameters (SMP) including parameters for: ambient environment and safety/security for said medication; said safety/security parameters including: operator/customer access authorization and real-time monitoring/verifications of a location of said medication within said apparatus;

a configurable conveyor carrier; said carrier including a configurable specification (SCC); said specification including carrier specification parameters (SCCP): shape, size (volume/capacity and dimensions), weight and identification (barcode label and/or electronic); said (SCC) including said carrier configurations of: a single section/pocket carrier for accepting a single container with prescription medication and a multi-section/pocket carrier with each section/pocket configured for accepting any combination consisting of a container with prescription medication and/or a medication accessory;

wherein (SS) including sensor configurations for monitoring and/or measuring a specification parameter of said apparatus, including: ambient environment (including temperature, humidity, emissions, vibrations), shape of an item (including item as an individual pill or a container) and dimension of an item (diameter or width, length, height);

wherein (SS) including sensor configurations for weight measurements of: an item, a carrier, a module and/or a component of said apparatus;

wherein (SS) including sensor configurations for recognition (reading) of an identification/specification parameter of an item (barcode label and/or electronic identification/tracking device attached to an item) with said items including: a container, a carrier, a device, an assembly;

wherein (SS) including sensor configurations for monitoring self-diagnostics of said apparatus including self-diagnostics of: a device, a mechanism and a module within said apparatus;

wherein (SS) including sensor configurations for monitoring safety and security of a medication within said apparatus;

wherein (SCC) for configurations of a multi-section/pocket carrier comprising of (SCCP) for each section/pocket of said carrier and including: shape, size (volume/capacity and dimensions), weight and identification (barcode label and/or electronic);

wherein (ST) including conveyor configurations for: vertical, horizontal and angular direction; said (ST) comprising attachment of a carrier; said attachment sustaining said carrier under the weight of said carrier (empty and/or loaded) in essentially vertical alignment; said (ST) comprising bi-directional transport; said (STP) defining: dimensional parameters, drive mechanism, local controller, communication interface to said controllers, and mechanical coupling to the carriers;

wherein said configurable apparatus is configured according to:

a configurable process specification for loading a prescription medication into a container (SLH); said (SLH) configurations including: auto-loading and manual loading by an authorized operator/provider; said (SLH) including verification of medication specification parameters listed in the (SM) and verification of other parameters as defined by a container loading quality acceptance criteria;

a configurable process specification for loading said container with prescription medication into a carrier (SLC); said (SLC) configurations including: auto-loading and manual loading by an authorized operator/provider; said (SLC) including verification of: medication specification parameters listed in the (SM), container specification parameters listed in (SH) and verification of other parameters as defined by a carrier loading quality acceptance criteria;

a configurable process specification for storing and for transporting said container with prescription medication within said apparatus (STC); said (STC) including attaching a carrier to a transport mechanism (conveyor) which sustains said carrier under the carrier own weight (empty and/or loaded with a container) essentially in a vertical orientation at all times; said (STC) including said conveyor transporting said medication within (SM), including ambient environment and safety/security; said (STC) including sustaining prescribed/listed by (SM) medication individual dosage (example weight of a pill or volume of a liquid) within respective acceptance criteria listed in the (SM);

a configurable process specification for unloading said container with prescription medication from said carrier to an authorized customer (SUC); said (SUC) including auto-dispensing/unloading of individual prescription medication to an authorized customer;

a configurable process specification for unloading said container with prescription medication from said carrier to an authorized provider (SUP); said (SUP) including auto-dispensing/unloading of individual prescription medication to an authorized customer;

a configurable specification for said apparatus (SA) including specification parameters (SAP); said (SA) including an acceptable criteria/range for said (SAP); said (SA) including said apparatus executing a control algorithm for sustaining said (SAP) within said acceptance criteria and communicating/informing a host controller and/or an authorized operator/provider of results;

a configurable process specification for said apparatus performing real-time inventory tracking within said apparatus (SIT); said (SIT) including tracking of components of said apparatus; said components including: modules and carriers; said (SIT) including tracking of containers with medication and comprising of detecting a transition of said medication based on identification (barcode label and/or electronic) attached to said medication and based on a change in weight with the original location losing weight and the new location gaining weight which is equal to the weight of medication being relocated;

a configurable acceptance criteria for said communication interface (AI); said (AI) including acceptable range for (SIP);

a configurable acceptance criteria for said sensor (AS); said (AS) including acceptable range for each of the specification parameters (SSP) monitored by said sensor;

a configurable acceptance criteria for said conveyor (AC); said (AC) including acceptable range for (STP);

a configurable acceptance criteria for loading a medication into a container (AMC); said (AMC) including a process specification in compliance to (SM); said process specification comprising of: said apparatus performing real-time inventory of empty containers and the containers with medications being present within said apparatus, and said apparatus with or without an operator assistance executing a list of process steps including: (1) selecting an empty container in compliance to the acceptance criteria, (2) loading said medication into selected container, (3) updating specification parameters for said loaded container and (4) creating a new identification for said loaded container as combination of identifications for said medication and of identifications for said container; said new identification comprising set of specification parameters defined by the provider; said new identification including barcode label and/or electronic device, and (5) attaching said identification to said container;

a configurable acceptance criteria for loading a container with medication into a carrier (ACC); said (ACC) including a process specification in compliance to (SM); said process specification comprising of: said apparatus performing real-time inventory and collecting identification data of carriers which are present in said apparatus and said apparatus with or without an operator assistance executing a list of process steps including: (1) selecting an empty carrier, (2) loading said container with medication into selected carrier, and (3) creating a new identification as combination of identifications for said medication and the identification data for said carrier; said new identification comprising of specification parameters defined by the provider; and 4) storing said new identification in the non-volatile memory;

a configurable acceptance criteria said vending module (AVM); said (AVM) including acceptable range for (SVMP);

a configurable acceptance criteria for dispensing module (ADM); said (ADM) including acceptable range for (SDMP) and a specification for said apparatus verification of (QC) specification parameters and (SIT) specification parameters in support of an error-free processing and delivery of a prescription medication to an authorized customer;

a configurable acceptance criteria for reject return module (ARM); said (ARM) including acceptable range for (SRMP);

a configurable acceptance criteria for customer interface (ACI); said (ACI) including acceptable range for (SCIP);

a configurable acceptance for provider interface (API); said (API) including acceptable range for (SPIP);

a configurable acceptance optimization criteria for a project; said project including a new installation of said apparatus; said acceptance optimization criteria comprising of optimization specification parameters defined by a provider for said project; said optimization specification parameters including project specific target/value/range for: reliability, security, safety and efficiency;

wherein said apparatus configured for aid project and operating in compliance to said optimization specification parameters;

wherein the configurable non-volatile memory is used by said apparatus and the provider for storing/retrieval of an information; said information including: specifications, parameters, acceptance criteria and a real-time data; said real-time data comprising of results/status information in respect to said apparatus executing in real-time the control algorithm;

wherein (SS) including sensor configurations for monitoring in real-time an actual value of a specification parameter of said apparatus;

wherein a specification parameter comprising of a range including low and high level of said parameter;

wherein a controller interfacing to a sensor monitors a specification parameter compares the actual value of said specification parameter to a range of values;

wherein said apparatus adaptable to a specification for a provider defined acceptance criteria, including:
  assisting a provider in preparing a prescription medication;
  assigning of a system specification to a prescription medication;
  verifying a medication compliance to said specifications prior to accepting and processing said prescription medication;
  distributing prescription medication in compliance with said specifications and in compliance with said acceptance criteria, including:
    providing/sustaining ambient environment;
    providing/sustaining safety and security;
    conveyor configurations, including: vertical distribution upward and/or downward from a provider location to an authorized location and/or horizontal distribution from a provider location to an authorized location;
    wherein an authorized location including: a specific floor number within a building, a specific location within a floor of a building including a specific service/patient room;
    wherein at an authorized location a prescription medication is delivered to an authorized person including: operator approved by a provider, customer and/or patient listed in a specification for said prescription medication; said delivery including automatic dispensing;

a configurable specification for a control algorithm (SCA); said specification including statistical calculations and real-time controls; said calculations including probability of an error in respect to apparatus non-compliance to an acceptance criteria in respect to processing a prescription medication; said controls sustaining operation of said apparatus according to said specifications and within said acceptance criteria; said real-time controls including real-time verification of an actual value provided by a sensor with a respective acceptable range; said verification including controls of sustaining the actual value of a measured parameter within its respective acceptance range; said algorithm providing real-time controls for sustaining an error-free processing of a prescription medication;

wherein said error-free processing is based on a predefined target set by the provider for a probability of occurrence of an error within said apparatus;

wherein a configuration of said apparatus is performed by an operator and/or a remote host controller over said communication interface including real-time configuration;

wherein a prioritization of said provider defined acceptance criteria for said apparatus is performed by an operator and/or a remote host controller over said communication interface including real-time prioritization;

wherein an authorized customer interfacing via an intelligent device (including mobile phone and/or computer) with said apparatus (in both directions) over said communication interfaces; said customer interfacing including: ordering medication, verifying status of an order, being informed of a location/date/time the order will be and/or is ready, instructions on how to use medication and general help instructions in support of customer services within provider defined acceptance criteria;

a configurable closed-loop control system of said apparatus; said control system monitoring status of said sensors and communicating over said communication interface with a remote host controller and/or an operator via an intelligent device connected to said apparatus; said communicating including said control system real-time self-diagnostics; said self-diagnostics including periodic (heart-beat) status updates; said status including an abbreviated status if said control system is within compliance and a detailed status in the event of an error; said detailed status including an identification of a component/device/process in error and identification of a prescription medication(s) being affected, if any; and said apparatus executing said configurable control algorithm sustaining operation of said apparatus within said prioritization of said provider defined acceptance criteria.

2. The apparatus of claim 1 operating within the acceptance criteria which include the apparatus executing the real-time controls of monitoring and sustaining the specification parameters of a prescription medication being processed by said apparatus.

3. The apparatus of claim 1 operating within the acceptance criteria which include the apparatus monitoring ambient environment, and the apparatus adapting to varying ambient environment, and sustaining a prescription medication within the specifications.

4. The-apparatus of claim 1 operating within the acceptance criteria which include the apparatus monitoring results of self-diagnostics, and adapting to varying results, and sustaining a prescription medication within the specifications.

5. The apparatus of claim 1 configured with the conveyor system for the vertical distribution of prescription medications within the acceptance criteria; said distribution within a building including to a number of floors of said building located above and/or below in respect to an origination/provider location (pharmacy, as example) of said medications; said conveyor system configurable for indoor and/or outdoor operation; said conveyor system configurable as a single or a multi-track conveyor system with each track or a section of a track configurable for compliance to the acceptance criteria including ambient environment and safety/security; said conveyor system configurable for providing single or a multiple access for: loading of said medications into the system, automatic dispensing of said medications from the system and manual unloading of said medications; said system adaptable to the acceptance criteria including: the quality and the security/safety acceptance criteria for providing error-free delivery of said prescription medications to an authorized customer.

6. The apparatus of claim 1 configured with the conveyor system for the horizontal distribution of prescription medications within the acceptance criteria; said distribution within a building including along a floor of said building; said conveyor system configurable for indoor and/or outdoor operation; said conveyor system configurable as a single or a multi-track conveyor system with each track or a section of a track configurable for compliance to the acceptance criteria including ambient environment and safety/security; said conveyor system configurable for providing single or a multiple access for: loading of said medications into the system, automatic dispensing of said medications from the system and manual unloading of said medications; said system adaptable to the acceptance criteria including: the quality and the security/safety acceptance criteria for providing error-free delivery of the prescription medications to an authorized customer.

7. An apparatus of claim 1 configured with the conveyor system for the vertical and the horizontal distribution of prescription medications within the acceptance criteria; said distribution within a building including: to a number of floors of said building above and/or below in respect to an origination location (pharmacy, as example) and along a floor of said building; said conveyor system configurable for indoor and/or outdoor operation; said conveyor system configurable as a single or a multi-track conveyor system with each track or a section of the track configurable for compliance to the acceptance criteria including ambient environment and safety/security; said conveyor system configurable for providing single or a multiple access for; loading of said medications into the system, automatic dispensing of said medications from the system and manual unloading of said medications; said system adaptable to the quality and the security/safety acceptance criteria for providing error-free delivery of the prescription medications to an authorized customer.

8. The apparatus of claim 1 configured as a closed loop system, with the controller configured to execute patient specific control algorithm, which is defined/configured by the provider within the patient specific specification parameters, and as instructed by the algorithm, with or without operator/provider assistance, the controller in real-time executing the controls, including dispensing of specified amount of medication, and informing the operator and/or the patient via the user interface of availability of the dispensed medications and of necessity/instructions for these medications to be administered to the patient, and request the operator and/or the patient to confirm to the controller that the medications were administered to the patient according to said instructions.

9. A method is described of configuring in real-time the apparatus of claim 1 comprising of a provider setting a target/specification of probability of an error-free processing of a prescription medication and defining specifications for: components, modules, processes and acceptance criteria, and-said apparatus executing a control algorithm configured by said provider for sustaining operation of said apparatus in compliance to said specifications including the error-free processing of said prescription medications for an authorized customer; said method providing improvements of:

quality of said prescription medications and quality of customer services from said provider; said improvements including significantly higher productivity and efficiency of servicing customers with the quality prescription medications via an unattended 24 hour auto-dispensing kiosk with an option for the customer of specifying the kiosk location within the provider service area; and said method further comprising of;

configuring the (SM) specification of a prescription medication (medication) according to an authorized provider and according to the acceptance criteria; said specification comprising of specification parameters associated with said medication including parameters defining: origination, storage, transportation and delivery of said medication; said origination parameters including: origination authority (a provider), location, date, name of medication, shape, size, volume and weight (unit and total) of said medication; said storage parameters including: ambient environment and expiration date of said medication; said transportation parameters including: ambient environment, distribution and routing within said apparatus of said medication; said delivery parameters including: method of delivery including auto-dispensing, location of delivery and verification parameters for an authorization of a customer to receive said prescription medication; said specification including an identification of said prescription medication comprising of a label (including human readable and barcode) and/or an electronic device (including RFID); said identification comprising of said specification parameters for said prescription medication;

configuring the (SH) specification for a container; said (SH) in compliance to a (SM) of a prescription medication and for storing said prescription medication;

configuring the (ST) specification of an automatic transport conveyor adaptable to said specification of said medication and comprising of specification parameters associated with said conveyor; said conveyor specification parameters including: a configurable carrier for storing said container; a configurable attachment method of said carriers to said conveyor, and a transporting method of said carriers by said conveyor adaptable to said specifications and said conveyor sustaining said prescription medications inside each carrier within said specifications; said container parameters including: shape, size, volume, weight and a serial number of said container which is unique within said apparatus; said specification including an identification of said container comprising of a label (including human readable and barcode) and/or an electronic device (including RFID); said identification comprising of said specification parameters for said container;

configuring the (SVM) specification of a vending module adaptable to said specification of said medication and comprising of specification parameters associated with said vending module; said vending module specification parameters including: a configurable conveyor for storing and for transporting carriers; a configurable dispensing module delivering a container from said vending module to an authorized customer; a configurable reject return module returning back from said vending module to a provider a container with a prescription medication out of specifications; and said vending module sustaining said prescription medications within said specifications;

configuring the identification of a container with a prescription medication inside wherein said identification is created by containing a list from specification parameters of said prescription medication and from specification parameters of said container housing said prescription medication; said identification attached to said container;

configuring identifications for the apparatus processing said medication; said identifications including: a carrier housing a container with a prescription medication inside, a conveyor transporting said carriers; a vending module housing said conveyor;

configuring a distribution routing for said medication by said apparatus in compliance to an acceptance routing criteria; said acceptance routing criteria applicable for a designated physical location of a provider and/or for a module of said apparatus; said acceptance routing criteria comprising a specification of no duplication of a combination of identifications; said combination is defined by the provider;

configuring the carrier of the apparatus including configurations of: a single pocket carrier for accepting/holding a single container and a multi-pocket carrier with each pocket accepting/holding a single container or a medication accessory;

configuring the acceptance criteria fore said apparatus (AA); said acceptance criteria including a quality criteria (QC) as a function of said specification parameters for a prescription medication; said (QC) including quality specification parameters of said apparatus for providing error-free distribution of prescription medications at a specified level of probability;

wherein the level of probability is defined by the provider or calculated/estimated by the controller executing a configuration of the control algorithm containing statistical analysis of a probability of an error within said apparatus;

configuring the acceptance optimization criteria comprising of optimization specification parameters defined by a provider for a project; said optimization specification parameters including target/value/range for: reliability, security, safety and efficiency;

configuring the controller for executing the configurable control algorithm and sustaining operation of the apparatus in compliance to;

configuring a quality acceptance criteria level 1 (QA-1) for said apparatus which is based on said quality criteria comprising of a specification for a configurable system level identification for a container with a prescription medication inside to remain unique within said apparatus or within a section of said apparatus; said configurable system level identification including a configuration comprising of said specification parameters listed for identification of a prescription medication and of said specification parameters listed for identification of a container which is housing said medication;

wherein said a configurable system level identification including a configuration defined by the provider and comprising of all or any combination from the following list of specification parameters; (1) serial number and (2) expiration date from identification of a prescription medication identification parameters of a container which is housing said medication including for said container: (3) shape, (4) size (volume), (5) diameter, (6) height, (7) weight and (8) serial number; said configuration said configuration of system level identification is unique among other configurable system level identifications residing in real-time inside said apparatus or inside a section of said apparatus;

wherein said system level identification specification parameters are measured by sensors and monitored by controllers connected to said sensors; said configuration of said system level identification comprising a specification for selecting specification parameters from said list in order of retaining its uniqueness among said other configurable system level identifications and retaining its compliance to said quality acceptance criteria level 1 (QA-1) in an event of a failure/malfunction of any one sensor among said sensors;

configuring the acceptance criteria for including a specification for said apparatus of using a sensor for real-time monitoring of a parameter from a control set; said sensor in mal-time reporting to said controller a result of monitoring a respective parameter; said controller rejecting a container with a prescription medication inside said apparatus when any of said respective parameters failed to match said specification;

configuring the control algorithm to be executed by said controller for providing error-free distribution of prescription medications to an authorized customer; said control algorithm comprising a closed-loop control processes of sustaining only prescription medications which (as reported by respective sensors to said controller) maintain a predefined by the provider a set of specification parameters from the point of entry into said apparatus to the point of delivering (dispensing) said prescription medication to an authorized customer; said controller informing an operator in real-time of an event when an actual specification parameter is out of acceptance range (error and/or malfunction) and executing controls for performing an error correction; said algorithm preventing dispensing of any medication to a customer by a vending module experiencing an error; said algorithm including real-time diagnostics performed by said controller and/or an operator;

configuring a quality acceptance criteria level 2 (QA-2) for said apparatus for sustaining a container with a prescription medication within a routing specification; said routing specification including: a serial number of a carrier housing said container, a serial number of a vending module advancing said carrier, and a serial number of a conveyor housing said vending module;

configuring a quality acceptance criteria level 3 (QA-3) for said apparatus for sustaining a container with a prescription medication within a quality specification level 3; said quality specification level 3 including specification parameters for a prescription medication not included in QA-1 and QA-2;

configuring a quality acceptance criteria (QS-1) for said apparatus for providing services to an authorized customer; said QS1 comprising of specifications from provider and specifications obtained from a customer; said QS-1 specifications comprising of specification parameters including: medication identification, location and time for a pick up;

configuring a security/safety acceptance criteria (QS-2) for said apparatus; said QS-2 comprising of specifications; said QS-2 specifications comprising of specification parameters including identification of authorized operator(s) for accessing/servicing said apparatus, for monitoring access to said, apparatus in real-time, and for detecting an un-authorized activity;

configuring the apparatus for distribution of a prescription medication to an authorized operator/customer as a function defined by a provider; said function comprising of: the component specifications, the module specifications, the process specifications, and the acceptance criteria, including: specifications for said medication, quality acceptance criteria's including combination of the QA-1/2/3, security/safety acceptance criteria's including combination of the QS-1/2, and acceptance criteria's for identification of said authorized operator/customer;

wherein sensor configurations including configurations for: monitoring location of the container with prescription medication, reading an identification label and/or electronic device attached to the container with prescription medication and monitoring presence of the container with prescription medication inside a carrier;

wherein sensor configurations including configurations for: optical recognition, optical reading of dimensional and shape specification parameters of an object including a container, electronic interface to identification device including RFID and weight measurements;

configuring the carrier for a mechanical coupling to a conveyor; said coupling including functions of: sustaining the carrier (under the carrier own weight or when loaded with an item) in a vertical alignment at all times, supporting elevation of the carrier from the coupling to allow a sensor to engage along the vertical axis with the currier and measure the carrier weight, and tilting the carrier around horizontal axis by an unloading mechanism to force the container to slide out of the carrier;

configuring the unloading module for: accepting a container with medication from a carrier, routing the container within the module, performing final verification of quality acceptance criteria and dispensing the container with prescription medication to a qualified customer;

configuring said apparatus and/or the vending module of said apparatus for operating as the stand-alone kiosk;

configuring said apparatus for defining/classifying a prescription medication as a reject as result of said medication non-compliance to an acceptance criteria; said acceptance criteria including: medication quality, medication tracking, customer service and medication safety/security;

configuring said apparatus for executing unloading process steps of a prescription medication to an authorized customer/operator in compliance to said unloading acceptance criteria;

configuring said apparatus for executing unloading process steps of a reject medication to an authorized provider in compliance to said reject unloading acceptance criteria;

configuring the acceptance criteria for said apparatus to include a specification for real-time location tracking of a container with prescription medication inside; said tracking comprising of location specification parameters of said medication within said apparatus; said location specification parameters including: serial number of a vending module and serial number of a carrier within said vending module;

configuring the communication interface between the controller of the apparatus and a remote controller including a host controller and/or an embedded controller of a device connected to the apparatus, and the communication interface based on one or combination of: wired, wireless and INTERNET;
configuring rigger points for the specification parameters;
configuring the acceptance criteria for the apparatus including as function of the trigger points;
configuring the control algorithm for operating the apparatus within the acceptance criteria;
configuring the apparatus as a real-time closed, loop control system and the system controller automatically with or without operator assistance executing in real-time the apparatus control algorithm sustaining the operation of the apparatus within the acceptance criteria.

10. The method of claim 9 of a provider defining the acceptance criteria for quality of prescription medication and the acceptance criteria for quality of customer services, and configuring an apparatus for automatic distribution of the prescription medications within said acceptance criteria.

11. The method of claim 9 of a provider defining the acceptance criteria for quality of prescription medication and the acceptance criteria for quality of customer services, and configuring the apparatus for a vertical single or bi-directional automatic distribution of the prescription medications within a building between an origination location (pharmacy) on one floor and other floors above and/or below, including configurations of a single or a multi-track delivery system (conveyor) with each track or a section of a track configurable for compliance to said acceptance criteria including ambient environment and safety/security, and the apparatus executing the control algorithm in compliance to said acceptance criteria.

12. The method of claim 9 of a provider defining the acceptance criteria for quality of prescription medication and the acceptance criteria for quality of customer services, and configuring the apparatus for a horizontal single or bi-directional automatic distribution of prescription medications along a floor of a building, including configurations of a single or a multi-track delivery system (conveyor) with each track or a section of a track configurable for compliance to said acceptance criteria including ambient environment and safety/security, and the apparatus executing the control algorithm in compliance to said acceptance criteria.

13. The method of claim 9 of an apparatus configured with a multi-pocket carrier(s) for automatic distribution of a prescription medication in a designed pocket and other items in the remaining pocket(s).

14. The method of claim 9 of an apparatus configured for a project; said project comprising of project specifications defined by a provider; said provider including: a franchise pharmacy, a stand-alone pharmacy, and a stand-alone kiosk; said pharmacy including configurations for providing pharmacy services within a building consisting of; a single floor and a multi-floor; said project specifications comprising of project acceptance criteria and of project specification parameters which are selected by said provider from: the specifications for the components and the modules of said apparatus, the process specifications for said apparatus, and the acceptance criteria for said apparatus; said project acceptance criteria comprising of optimization specification parameters defined by said provider; said optimization specification parameters include a target/value/range for: reliability, security, safety and efficiency; said apparatus operating in compliance to said project specifications, including said pharmacy services, and providing improved: quality of customer services and quality of prescription medications delivered to authorized customers.

15. The method of claim 9 of an apparatus configured as a closed loop control system, with the controller configured to execute the control algorithm directing the apparatus with or without operator assistance for automatic distribution of patient specific prescription medication directly to an authorized patient including the interface with controller for the patient confirming arrival and acceptance of the prescription medication.

16. The method of claim 9 of an apparatus configured as a closed loop control system executing a control algorithm adaptable to a provider specification(s) and adaptable to an acceptance criteria including configurations of the algorithm which are performed in real-time by an authorized operator and/or a host controller over the system supported interface including: operator computer interface, wireless network and mobile device(s).

17. The method of claim 9 of a provider defining acceptance criteria for a prescription medication identification parameters (label, electronic device) and acceptance criteria for prescription medication routing/distribution/location parameters, and an apparatus configured for real-time monitoring of the identification parameters and the location parameters for the prescription medication within the apparatus, and the apparatus executing a control algorithm of dispensing to an authorized customer only a prescription medication in full compliance to the acceptance criteria in respect to the identification and the location parameters, and the apparatus dispensing rejected prescription medication back to the provider.

18. The method of claim 9 of an apparatus configured for integrating into a new or an existing building (hospital, elderly care, multi-floor pharmacy) including mounting of the enclosed transport system (conveyor) along the exterior wall(s) of, the building and providing respective cut-out in the walls for access to the apparatus operator interface(s) and dispensing bin(s).

19. The method of claim 9 of a provider defining an acceptance criteria including an error-free probability target(s) for the processes of: preparing a prescription medication, storing and transporting a prescription medication and delivering/dispensing a prescription medication; a control algorithm configured for said acceptance criteria including a process of selecting identification parameters for a prescription medication and a process of selecting a number/type of sensors for monitoring said identification parameters; and an apparatus configured for executing said control algorithm for sustaining said processes within said acceptance criteria; said apparatus communicating through an interface and informing periodically (heart-beat) status to said provider; said status in the event of an error including identification of a prescription medication(s) being affected: said apparatus auto-dispensing to an authorized customer only prescription medication(s) within said acceptance criteria.

20. The method of claim 9 of an apparatus configured for improving the quality of prescription medication, and the method comprising of the apparatus performing a real-time auto-verifications of the specification parameters defining the quality of the prescription medication and the specification parameters defining the quality of the container with the prescription medication; said auto-verifications including: (1) said prescription medication serial label/number (barcode, RFID), (2) the information of said prescription medication stored in the non-volatile memory; (3) said container serial label/number, size, weight and environment (ambient/safety/security), (4) the location of said container within the apparatus, and (5) the information of said container stored in the non-volatile memory; and the quality of said prescription medication is significantly less dependent from the provider internal factors including: number of available operators for the provider and number of active prescription medications being processed by the provider, as well as from the provider external factors including: location of customers within the provider service are, and fluctuating demands including peak demands during a flu season for prescription medications; and the apparatus performing final auto-verifications prior to auto-dispensing of only the quality prescription medications to an authorized customer.

21. The method of claim 9 of an apparatus configured for improving the quality of customer services available from a provider, and the method comprising of the apparatus configured per the provider specifications and acceptance criteria: for the most optimum routing/distribution/processing of quality prescription medications from the provider to a customer, and for performing real-time auto-verifications/corrections of the quality of services for each of the customers; and the quality of services are significantly less dependent from the provider internal factors including: (1a) number of available operators for the provider and (2a) number of active prescription medications being processed by the provider, as well as from the provider external factors including (1b) number of customers waiting at the provider to receive prescription medication(s), (2b) location of customers in respect to the provider service area and (3b) fluctuating demands including peak demands during a flu season) for prescription medications; and the apparatus performing final auto-verifications prior to auto-dispensing of only the quality prescription medications to an authorized customer.

\* \* \* \* \*